(12) United States Patent
Tenney et al.

(10) Patent No.: US 9,188,973 B2
(45) Date of Patent: Nov. 17, 2015

(54) CALIBRATION AND TRANSFORMATION OF A CAMERA SYSTEM'S COORDINATE SYSTEM

(75) Inventors: John A. Tenney, Peidmont, CA (US); Erik R. Burd, San Francisco, CA (US); Hui Zhang, San Jose, CA (US); Robert F. Biro, Sunnyvale, CA (US)

(73) Assignee: Restoration Robotics, Inc., San Jose, CA (US)

( * ) Notice: Subject to any disclaimer, the term of this patent is extended or adjusted under 35 U.S.C. 154(b) by 972 days.

(21) Appl. No.: 13/178,867

(22) Filed: Jul. 8, 2011

(65) Prior Publication Data

US 2013/0010081 A1     Jan. 10, 2013

(51) Int. Cl.
*H04N 13/02*     (2006.01)
*G05B 19/408*     (2006.01)
*G06T 7/00*     (2006.01)
*B25J 9/16*     (2006.01)

(52) U.S. Cl.
CPC ........... *G05B 19/4086* (2013.01); *B25J 9/1697* (2013.01); *G06T 7/002* (2013.01); *G06T 7/0042* (2013.01); *G05B 2219/39022* (2013.01); *G05B 2219/39045* (2013.01); *G06T 2207/30004* (2013.01); *G06T 2207/30208* (2013.01); *G06T 2207/30244* (2013.01)

(58) Field of Classification Search
CPC .......... H04N 13/0239; H04N 13/0296; H04N 13/0055; H04N 2013/0081; G06T 7/0022; G06T 2207/30004; G06T 2207/30208; G06T 2207/30244
USPC .......................................................... 348/47
See application file for complete search history.

(56) References Cited

U.S. PATENT DOCUMENTS

| | | | |
|---|---|---|---|
| 5,817,105 A | 10/1998 | Van Der Brug | |
| 6,228,089 B1 * | 5/2001 | Wahrburg | 606/86 R |
| 6,256,099 B1 | 7/2001 | Kaufman et al. | |
| 6,273,858 B1 * | 8/2001 | Fox et al. | 600/466 |

(Continued)

FOREIGN PATENT DOCUMENTS

| EP | 2070664 | 6/2009 |
|---|---|---|
| JP | 2009509671 | 3/2009 |

(Continued)

OTHER PUBLICATIONS

Calibration of Wrist-Mounted Robotic Sensors by Solving Homogenous Transform Equations, Feb. 1989.*

(Continued)

*Primary Examiner* — William Tran
(74) *Attorney, Agent, or Firm* — Sharon Upham; Lena I. Vinitskaya

(57) ABSTRACT

Systems and methods are disclosed that determine a mapping between a first camera system's coordinate system and a second camera system's coordinate system; or determine a transformation between a robot's coordinate system and a camera system's coordinate system, and/or locate, in a robot's coordinate system, a tool extending from an arm of the robot based on the tool location in the camera's coordinate system. The disclosed systems and methods may use transformations derived from coordinates of features found in one or more images. The transformations may be used to interrelate various coordinate systems, facilitating calibration of camera systems, including in robotic systems, such as an image-guided robotic systems for hair harvesting and/or implantation.

26 Claims, 27 Drawing Sheets

(56) References Cited

U.S. PATENT DOCUMENTS

| | | | |
|---|---|---|---|
| 6,585,746 B2 | 7/2003 | Gildenberg | |
| 6,917,702 B2 | 7/2005 | Beardsley | |
| 6,973,202 B2 | 12/2005 | Mostafavi | |
| 7,231,063 B2 | 6/2007 | Naimark et al. | |
| 7,277,120 B2 | 10/2007 | Gere et al. | |
| 7,386,365 B2 | 6/2008 | Nixon | |
| 7,426,318 B2 | 9/2008 | Fu et al. | |
| 7,542,051 B2 | 6/2009 | Matsui et al. | |
| 7,660,623 B2 | 2/2010 | Hunter et al. | |
| 7,962,192 B2 | 6/2011 | Bodduluri et al. | |
| 8,048,090 B2 | 11/2011 | Qureshi et al. | |
| 2003/0120298 A1* | 6/2003 | Gildenberg | 606/187 |
| 2004/0243282 A1* | 12/2004 | Watanabe et al. | 700/259 |
| 2005/0096515 A1 | 5/2005 | Geng | |
| 2005/0159842 A1* | 7/2005 | Ban et al. | 700/245 |
| 2005/0180623 A1* | 8/2005 | Mueller et al. | 382/154 |
| 2007/0078466 A1 | 4/2007 | Bodduluri et al. | |
| 2007/0106306 A1* | 5/2007 | Bodduluri et al. | 606/133 |
| 2007/0127795 A1 | 6/2007 | Lau et al. | |
| 2008/0002809 A1 | 1/2008 | Bodduluri | |
| 2008/0004633 A1 | 1/2008 | Arata et al. | |
| 2008/0091373 A1* | 4/2008 | McGibbon et al. | 702/95 |
| 2008/0202200 A1 | 8/2008 | West | |
| 2009/0003523 A1 | 1/2009 | Raanes et al. | |
| 2009/0096790 A1* | 4/2009 | Wiedemann et al. | 345/427 |
| 2009/0154646 A1* | 6/2009 | Carol et al. | 378/65 |
| 2009/0180678 A1 | 7/2009 | Kuduvalli et al. | |
| 2010/0020201 A1* | 1/2010 | Chao et al. | 348/239 |
| 2010/0080415 A1 | 4/2010 | Qureshi et al. | |
| 2010/0245541 A1 | 9/2010 | Zhao et al. | |
| 2010/0305754 A1* | 12/2010 | Ban et al. | 700/248 |
| 2011/0282473 A1* | 11/2011 | Pavlovskaia et al. | 700/98 |
| 2012/0050493 A1* | 3/2012 | Ernst et al. | 348/47 |

FOREIGN PATENT DOCUMENTS

| | | |
|---|---|---|
| WO | 2007/041267 | 4/2007 |
| WO | 2011/079258 | 6/2011 |
| WO | 2011/143576 | 11/2011 |

OTHER PUBLICATIONS

English Translation of Japanese Office Action mailed Jun. 17, 2014, in connection with commonly assigned Japanese Patent Application No. 2014-519220. Restoration Robotics, Inc. (4 pages).

Yik San Kwoh, Joahin Hou, Edmond A. Jonckheere, Samad Hayati. "A Robot with Improved Absolute Positioning Accuracy for CT guided Stereotactic Brain Surgery". IEEE Transactions of Biomedical Engineering vol. 35. No. 2. Feb. 1988. p. 153-160 (8 pages).

Ramesh Jain, Rangachar Kasturi, Brian G. Schunck. "Machine Vision". McGraw-Hill, Inc. 1995. Cover page, publication page, and Chapter 12, pp. 309-364.

"Multi-Camera Self-Calibration". Printed May 2, 2011, from http://cmp.felk.cvut.czi~svoboda/SelfCal/index.html (2 pages).

"Camera Calibration Toolbox for Matlab". Printed May 2, 2011, from http://www.vision.caltech.edu/bouguetj/calib_doc/htmls/parameters.html (4 pages).

"Camera Calibration Toolbox for Matlab". Printed May 2, 2011, from http://www.vision.caltech.edu/bouguetj/calib_doc/htmls/example5.html (6 pages).

Alexandre Krupa. "Automatic Calibration of a Robotized 3D Ultrasound Imaging System by Visual Servoing". IRISA—INRIA Rennes. Downloaded from http://www.irisa.fr/lagadic/pdf/2006_icra_krupa.pdf (6 pages).

English Translation of Office Action mailed May 27, 2014, in connection with commonly assigned Korean Patent Application No. 10-2014-70000496 (5 pages).

Notification of Transmittal of International Search Report and Written Opinion mailed Jan. 14, 2013, in relation to commonly assigned International Application No. PCT/US2012/045202, Jan. 14, 2013 (10 pages).

Supplementary European Search Report and Written Opinion, mailed Mar. 19, 2014, in connection with commonly assigned European Patent Application No. 12811280.2 (7 pages).

Supplementary European Search Report and Written Opinion, mailed Mar. 19, 2014, in connection with commonly assigned European Patent Application No.12811280.2 (8 pages).

Shiu, Yiu C. et al., "Calibration of Wrist-Mounted Robotics Sensors by Solving Homogeneous Transform Equations of the Form AX=XB", IEEE Transactions on Robotics and Automation, vol. 5, No. 1, Feb. 1989, pp. 16-29.

Zhuang, Hanqi et al., "Comments on "Calibration of Wrist-Mounted Robotic Sensors by Solving Homogeneous Transform Equations of the Form AX=XB"", IEEE Transactions on Robotics and Automation, vol. 7, No. 6, Dec. 1991 (pp. 877-878).

English Language Translation of Office Action mailed Oct. 13, 2014, in connection with commonly assigned Korean Patent Application No. 10-2014-7000496 (5 pages).

English Translation of Chinese First Office Action mailed Jan. 4, 2015, in connection with commonly assigned Chinese Patent Application No. 201280033235.X (2 pages).

Office Action mailed Feb. 26, 2015 in connection with commonly Assigned European Patent Appln. No. 12811280.2, Feb. 26, 2015, (8 pages).

Tsai, et al., "A New Technique for Fully Autonomous and Efficient 3D Robotics Hand/Eye Calibration", IEEE Transactions on Robotics and Automation, IEEE Inc, New York, US, vol. 5, No. 3, Jun. 1, 1989, pp. 345-358.

Zhuang, et al., "A Noise-Tolerant Algorithm for Robotic Hand-Eye", IEEE Trans. Systems, Man, Cybernetics, vol. 23, No. 4, Jul./Aug. 1993, (6 pages).

* cited by examiner

CALIBRATION AND TRANSFORMATION OF A CAMERA SYSTEM'S COORDINATE SYSTEM

TECHNICAL FIELD

The present disclosure generally relates to automated systems, such as robotic systems, and in particular, to systems and methods for calibrating a camera system of an image-guided robotic system.

BACKGROUND INFORMATION

Robotic systems, such as robotic systems that include a movable robotic arm having a tool, inspection unit, or other device mounted thereto, generally include guidance systems to position the robotic arm from one location to another location. Image-guided robotic systems generally position the robotic arm based, at least in part, on processed images, which in certain applications may be acquired by one or more cameras. To help accurately position an image-guided robotic system, it may be desirable to perform calibration. Examples of such calibration procedures are described, for example, with reference to FIG. 4 of U.S. Patent Publication No. 2007/0106306 of Bodduluri et al.

SUMMARY

In one embodiment, a method is provided for determining a mapping between a first camera system's coordinate system and a second camera system's coordinate system, wherein the first and second camera systems have fields of view that at least partially overlap, and wherein the first and second camera systems have a fixed spatial relationship. The method comprises determining, using one or more processors, coordinates in both the first and second camera systems' coordinate systems of a set of features (e.g., one or more features) found in corresponding pairs of images from the first and second camera systems, thereby resulting in a first set of feature coordinates in the first camera system's coordinate system and a corresponding second set of coordinates in the second camera system's coordinate system, and determining by use of one of the same the one or more processors or a different processor, based on the first and second set of feature coordinates, a mapping between the first and second camera system coordinate systems. The method may store the mapping in a memory for later use to convert coordinates between the first and second camera systems' coordinate systems. In some embodiments the method may optionally capture, receive, or accept a number of corresponding images from each of the first and second camera systems.

In another embodiment, a system is provided comprising one or more processors configured to determine coordinates in a coordinate system of a first camera system for a set of features in a first set of images thereby resulting in a first set of feature coordinates in the coordinate system of the first camera system, determine coordinates in a coordinate system of a second camera system for a set of features in a second set of images, wherein the features in the second set of images correspond to the first set of features in the first set of images, thereby resulting in a second set of feature coordinates in the coordinate system of the second camera system, and compute, based on the first and second set of feature coordinates, a transformation between the coordinate systems of the first and second camera systems. The system may store the mapping in a memory for later use to convert coordinates between the first and second camera systems' coordinate systems. A single processor may perform all the operations recited. In some embodiments, the system also includes a first camera system having a first field of view and configured to capture the first set of images and a second camera system having a second field of view and configured to capture the second set of images corresponding to the first set of images, wherein the first and second camera systems are positioned in locations fixed with respect to each other and wherein the first and second fields of view at least partially overlap.

In still another embodiment, each of the first and second camera systems comprises a stereo pair of cameras. In yet another embodiment, the first and second camera systems differ in the sizes of their fields of view. In still another embodiment, the first and second camera systems are mounted to a robotic arm that may be part of a robotic system, for example, a robotic system for hair harvesting and/or implantation. In yet another embodiment, the images may be captured, received, or accepted at approximately the same time. In still another embodiment, the features are calibration features, which may be selected from one or more of a group consisting of checkerboard corners, dot pattern, or centroids.

In yet another embodiment, the number of corresponding images from each of the first and second camera systems is m, the $j^{th}$ image from the first camera system and the $j^{th}$ image from the second camera system correspond to each other for j=1 . . . m, the number of features whose coordinates are determined in each image is n, the first set of coordinates determined in the first camera system's coordinate system is $\{v_{1jk}\}$, and the second set of coordinates determined in the second camera system's coordinate system is $\{v_{2jk}\}$ where j is an index to the $j^{th}$ image among the images 1 . . . m, and k is an index to a $k^{th}$ feature among the features 1 . . . n in the $j^{th}$ image. In some embodiments, m≥1 and n≥2, and mn≥6. According to one embodiment, m=48 and n=6.

Is still another embodiment, the mapping is a transformation matrix Q that transforms coordinates from the second coordinate system to the first coordinate system, and the step of finding the mapping comprises finding a matrix Q that at least approximately minimizes the quantity $\Sigma_{j=1}^{m} \Sigma_{k=1}^{n} d(Qv_{2jk}, v_{1jk})$ wherein d is a distance function, such that $v_1 \approx Qv_2$ where $v_1$ and $v_2$ are vectors of coordinates in the first and second camera system coordinate systems, respectively. Additionally, in some embodiments Q is a 4×4 matrix, and the vectors of coordinates are in a form like the following:

$$\begin{bmatrix} x \\ y \\ z \\ 1 \end{bmatrix}.$$

Furthermore, in some embodiments the distance function d is $d=\|Qv_{2jk} - v_{1jk}\|$. Moreover, finding the transformation matrix Q may comprise using an optimization technique.

In yet another embodiment, an apparatus for determining a mapping between a first camera system's coordinate system and a second camera's coordinate system is provided. The first and second camera systems have fields of view that at least partially overlap and the first and second camera systems have a fixed spatial relationship. The apparatus comprises means for determining coordinates in both the first and second camera systems' coordinate systems of a set of features found in corresponding pairs of images from the first and second camera systems, thereby resulting in a first set of feature coordinates in the first camera system's coordinate system and a corresponding second set of coordinates in the second camera system's coordinate system, and means for determining, based on the first and second set of feature coordinates, a mapping between the first and second camera system coordinate systems. In some embodiments, the apparatus further comprises means for capturing a number of corresponding images from each of the first and second camera systems.

In another embodiment, a method is provided for determining a transformation between a robot's coordinate system and a camera system's coordinate system, wherein the robot includes a movable arm having the camera system mounted thereto, the robot's coordinate system defines a position of the movable arm, and the camera system's coordinate system defines a position of a target within a field of view of the camera system. The method comprises positioning the movable arm about the target to multiple image-capture locations such that the target is within the field of view of the camera system at individual image-capture locations and the movable arm is rotated about and translated relative to the target from one image-capture location to another image-capture location, at the individual image-capture locations, capturing a set of images of the target using the camera system and recording, in the robot's coordinate system, a position of the movable arm, determining, in the camera system's coordinate system, coordinates of a set of calibration features of the target identified in the set of images, and determining, based on the position of the movable arm and the coordinates of the set of calibration features at the individual image-capture locations, the transformation between the robot's coordinate system and the camera system's coordinate system.

In some embodiments of the method for determining a transformation between a robot's coordinate system and a camera system's coordinate system, the steps of positioning the movable arm about the target, capturing the set of images of the target, recording the position of the movable arm, determining the coordinates of the set of calibration features, and determining the transformation between the robot's coordinate system and the camera system's coordinate system are performed automatically. In yet another embodiment, the movable arm has mounted thereto a follicular unit harvesting tool, a follicular unit implantation tool, or both, and the robot is configured to harvest follicular units, implant follicular units, or both.

In still another embodiment of the method further comprises identifying, in the camera system's coordinate system, a location of a follicular unit in an image of the body surface, determining, in the robot's coordinate system, a location of the follicular unit based on the location of the follicular unit in the camera system's coordinate system and the transformation between the robot's coordinate system and the camera system's coordinate system, and positioning the movable arm adjacent the follicular unit based on the location of the follicular unit in the robot's coordinate system so that the follicular unit can be harvested or implanted using the follicular unit harvesting or implantation tool.

In another embodiment, a system is provided. The system comprises a movable arm having a coordinate system defining a position of the movable arm, a camera system mounted on the moveable arm, the camera system configured to capture one or more images, such as a set of images, and having a coordinate system defining a position of a target within a field of view of the camera system, a controller operatively coupled to the moveable arm, the controller configured to position the movable arm about the target to multiple image-capture locations such that the target is within the field of view of the camera system at individual image-capture locations and the movable arm is rotated about and translated relative to the target from one image-capture location to another image-capture location. The system further comprises a memory, and a processor operatively coupled to the camera system, the controller, and the memory. The processor is configured to, at the individual image-capture locations, cause the camera system to capture a set of images of the target using the camera system, determine, in the camera system's coordinate system, coordinates of a set of calibration features of the target identified in the set of images, at the individual image-capture locations. The processor is further configured to store in the memory a position of the movable arm in the movable arm's coordinate system, and determine, based on the position of the movable arm and the coordinates of the set of calibration features at the individual image-capture locations, a transformation between the movable arm's coordinate system and the camera system's coordinate system. In certain embodiments, the processor may interrogate the controller at the individual image-capture locations to determine a position of the movable arm in the movable arm's coordinate system and the processor may query the camera system at the individual image-capture locations to determine, in the camera system's coordinate system, coordinates of the set of calibration features of the target identified in the set of images. Moreover, the controller may position the movable arm about the target and the processor may cause the camera system to capture the set of images of the target, determine the coordinates of the set of calibration features, store the position of the movable arm, and determine the transformation between the movable arm's coordinate system and the camera system's coordinate system automatically without user intervention.

In yet another embodiment of the system, the movable arm has mounted thereto a follicular unit harvesting tool, a follicular unit implantation tool, or both, and the system comprises a robotic system configured to harvest follicular units, implant follicular units, or both. In some embodiments, the processor is further configured to cause the camera system to capture an image of a body surface, identify, in the camera system's coordinate system, a location of a follicular unit in the image of the body surface, determine, in the movable arm's coordinate system, a location of the follicular unit based on the location of the follicular unit in the camera system's coordinate system and the transformation between the movable arm's coordinate system and the camera system's coordinate system, and cause the controller to position the movable arm adjacent the follicular unit based on the location of the follicular unit in the movable arm's coordinate system so that the follicular unit can be harvested or implanted using the follicular unit harvesting or implantation tool.

In still another embodiment, a position of the target is fixed and the transformation between the movable arm's coordinate system and the camera system's coordinate system is determined (e.g., by the processor) by iteratively selecting a value for the transformation between the movable arm's coordinate system and the camera system's coordinate system and comparing (A) a product of the selected value for the transformation, a position of the movable arm, and coordinates of a calibration feature at one image-capture location and (B) a product of the selected value for the transformation, a position of the movable arm, and coordinates of the corresponding calibration feature at another image-capture location to determine a value for the transformation that minimizes a difference between (A) and (B).

In yet another embodiment, the transformation between the movable arm's coordinate system and the camera system's coordinate system comprises a transformation matrix T and the transformation is determined (e.g., by the processor)

by finding a transformation matrix T that at least approximately minimizes the quantity $\Sigma_{i=2}^{m}\Sigma_{j=1}^{(i-1)}\Sigma_{k=1}^{n}\|R_iTv_{ik}-R_jTv_{jk}\|$, wherein i and j correspond to different instances of individual image-capture locations, i has a value ranging from 2 to m, j has a value ranging from 1 to (i−1), k corresponds to an individual calibration feature in the set of calibration features and has a value ranging from 1 to n, $R_i$ is the position of the movable arm at an individual image-capture location i, $v_{ik}$ are the coordinates, determined in the camera system's coordinate system, of the $k^{th}$ calibration feature at the $i^{th}$ image-capture location, $R_j$ is the position of the movable arm at an individual image-capture location j, and $v_{jk}$ are the coordinates, determined in the camera system's coordinate system, of the $k^{th}$ calibration feature at the $j^{th}$ image-capture location.

In certain embodiments, the position of the movable arm may comprise a movable-arm-position transformation matrix R of the form $$R = \begin{bmatrix} r_{00} & r_{01} & r_{02} & x \\ r_{10} & r_{11} & r_{12} & y \\ r_{20} & r_{21} & r_{22} & z \\ 0 & 0 & 0 & 1 \end{bmatrix},$$

wherein the sub-matrix $$\begin{bmatrix} r_{00} & r_{01} & r_{02} \\ r_{10} & r_{11} & r_{12} \\ r_{20} & r_{21} & r_{22} \end{bmatrix}$$

represents an orthonormal rotation relating an orientation of the movable arm to a reference orientation and the sub-matrix $$\begin{bmatrix} x \\ y \\ z \end{bmatrix}$$

represents an offset between the position of the movable arm and a reference position, the coordinates of an individual calibration feature may comprise an array of the form $$v = \begin{bmatrix} x \\ y \\ z \\ 1 \end{bmatrix},$$

and the transformation matrix T may comprise a matrix or the form $$T = \begin{bmatrix} r_{00} & r_{01} & r_{02} & x \\ r_{10} & r_{11} & r_{12} & y \\ r_{20} & r_{21} & r_{22} & z \\ 0 & 0 & 0 & 1 \end{bmatrix},$$

where the sub-matrix $$\begin{bmatrix} r_{00} & r_{01} & r_{02} \\ r_{10} & r_{11} & r_{12} \\ r_{20} & r_{21} & r_{22} \end{bmatrix}$$

represents a rotational relationship between the movable arm's coordinate system and the camera system's coordinate system and is derived from three rotational offsets α, β, and γ and the sub-matrix $$\begin{bmatrix} x \\ y \\ z \end{bmatrix}$$

represents translation offsets x, y, and z between the movable arm's coordinate system and the camera system's coordinate system.

The transformation matrix T may comprise six independent values, three of which are translation offsets x, y, and z and the other three of which are rotational offsets α, β, and γ, and the six independent values are determined using an optimization algorithm. In still another embodiment, the transformation between the robot's coordinate system and the camera system's coordinate system is determined (e.g., by the processor) by using an optimization algorithm including, for example, a steepest descent optimization algorithm, and/or a simulated annealing algorithm, and/or a best fit algorithm. The individual image-capture locations may lie approximately on a surface of a sphere having a center point approximately coincident with the target and the movable arm may be moved radially with respect to the target from one image-capture location to another image-capture location.

In one embodiment the camera system comprises respective first and second stereo camera pairs mounted to the movable arm, the first stereo camera pair is focused and configured to acquire images of a first field of view, the second stereo camera pair is focused and configured to acquired images of a second field of view that is substantially narrower than the first field of view, the first and second fields of view at least partially overlap, and the transformation between the movable arm's coordinate system and the camera system's coordinate system is determined (e.g., by the processor) by determining a first transformation for the first stereo camera pair using an optimization algorithm and determining a second transformation for the second stereo camera pair using an optimization algorithm. Moreover, a transformation matrix Q that maps coordinates in the first stereo camera pair's coordinate system to the second stereo camera pair's coordinate system may be determined (e.g., by the processor).

In another embodiment, a system for determining a transformation between a robot's coordinate system and a camera system's coordinate system is provided, wherein the robot includes a movable arm having the camera system mounted thereto, the robot's coordinate system defines a position of the movable arm, and the camera system's coordinate system defines a position of a target within a field of view of the camera system. The system comprises means for positioning the movable arm about the target to multiple image-capture locations such that the target is within the field of view of the camera system at individual image-capture locations and the movable arm is rotated about and translated relative to the target from one image-capture location to another image-capture location, means for capturing, at the individual image-capture locations, a set of images of the target using the camera system, means for recording, in the robot's coordinate system, a position of the movable arm, means for determining, in the camera system's coordinate system, coordinates of a set of calibration features of the target identified in the set of images, and means for determining, based on the position of the movable arm and the coordinates of the set of calibration features at the individual image-capture locations, the transformation between the robot's coordinate system and the camera system's coordinate system.

In another embodiment, a computer readable medium having instructions stored thereon is provided. The instructions comprise instructions for causing a movable arm of a robot to be positioned about a target to multiple image-capture locations such that the target is within a field of view of a camera system mounted to the movable arm at individual image-capture locations and the movable arm is rotated about and translated relative to the target from one image-capture location to another image-capture location, instructions for causing the camera system to capture a set of images of the target at the individual image-capture locations, instructions for recording, in a robot's coordinate system, a position of the movable arm, instructions for determining, in a camera system's coordinate system, coordinates of a set of calibration features of the target identified in the set of images, and instructions for determining, based on the position of the movable arm and the coordinates of the set of calibration features at the individual image-capture locations, the transformation between the robot's coordinate system and the camera system's coordinate system.

In another embodiment, a method is provided for locating, in a robot's coordinate system, a tool extending from an arm of the robot. The method comprises determining from image data a location in a camera system's coordinate system of the tool, and translating the location of the tool from the camera system's coordinate system into the robot's coordinate system using a predetermined transformation.

In some embodiments, the method includes capturing image data. In still another embodiment, the image data comprises a pair of images, and the determining step comprises detecting from the image data first and second peripheral sidewall edge segments corresponding to sides of the tool within a field of view of the camera system, computing a centerline based on an average between the detected first and second peripheral sidewall edge segments, and locating in the camera system's coordinate system a position of a distal end of the tool along the centerline. In some embodiments, the centerline bisects an angle formed between the first and second peripheral sidewall edge segments. In certain embodiments, the tool may comprise a needle or punch for performing hair follicle harvesting.

In certain embodiments, the detecting step comprises locating first and second data transitions in individual rows of the image data to establish a first and second set of data transitions, calculating the first and second peripheral sidewall edge segments by performing a regression from the respective first and second sets of data transitions, and the locating step comprises locating a distal-end data transition in the image data along the centerline such that the location of the distal-end data transition represents the spatial position of the distal end in the camera system's coordinate system.

Various tools, including a single needle, punch or cannula, or tool assemblies of various configurations may be used in different embodiments. In some embodiments, the first and second data transitions may comprise one or more contrast, intensity, color, or brightness transitions of the image data, and the detecting step may further comprise processing the image data such that the distal end of the tool is represented as a unique value within the image data, e.g., a unique color within the image data. In some embodiments, the detecting step may further comprise binarizing the image data such that the distal end is represented by a first unique color and background features are represented by a second unique color. In some embodiments, the regression comprises a best-fit algorithm or a least-squares fit that approximately connects respective first and second sets of data transitions.

In another embodiment, a system is provided that is configured to locate, in a robot's coordinate system, a tool extending from an arm of the robot. The system may comprise one or more processors configured to determine from the image data a location in the camera system's coordinate system of the tool, and translate the location of the tool from the camera system's coordinate system into the robot's coordinate system using a predetermined transformation.

In some embodiments, the system includes a camera system having a coordinate system, and the camera system is configured to capture image data. In still another embodiment, the image data comprises a pair of images, and the one or more processors are further configured to determine the location by detecting from the image data first and second peripheral sidewall edge segments corresponding to sides of the tool within a field of view of the camera system, computing a centerline based on an average between the detected first and second peripheral sidewall edge segments, and locating, in the camera system's coordinate system, a spatial position of a distal end of the tool along the centerline. In some embodiments, the centerline bisects an angle formed between the first and second peripheral sidewall edge segments.

In some embodiments, the one or more processors are further configured to detect the first and second peripheral sidewall edge segments of the tool by locating first and second data transitions in individual rows of the image data to establish a first and second set of data transitions, calculating the first and second peripheral sidewall edge segments by performing a regression from the respective first and second sets of data transitions, and locate a position of the distal end of the tool by locating a distal-end data transition in the image data along the centerline such that the location of the distal-end data transition represents the spatial position of the distal end in the camera system's coordinate system.

In some embodiments the one or more processors may be further configured to detect the first and second peripheral sidewall edge segments of the tool by excluding from the first and second sets of data transitions, a first or second data transition having a distance from the respective first and second initial peripheral sidewall edge segments that exceeds a predetermined threshold. In certain embodiments, the one or more processors may be further configured to re-calculate the first and second peripheral sidewall edge segments by performing a regression from the respective first and second sets of data transitions, and the distal-end data transition corresponds to the distal end of the tool, such as the harvesting punch, when it is extended or retracted to a different position (e.g. approximately at the predetermined skin-plane distance).

In another embodiment, a system is provided for locating, in a robot's coordinate system, a tool extending from an arm of the robot. The system comprises means for determining from the image data a location in a camera system's coordinate system of the tool, and means for translating the location of the tool from the camera system's coordinate system into the robot's coordinate system using a predetermined transformation. The system may also include means for capturing image data.

In another embodiment, a method is provided for identifying relative positions or magnification of a camera in a camera system. The method comprises placing a placard bearing fiducials in a camera system's field of view such that individual cameras may observe at least one fiducial, receiving image data representing fiducials from individual cameras in the camera system, and characterizing the individual cameras based on the representation of the fiducials in the image data.

DETAILED DESCRIPTION OF EMBODIMENTS

Figure 1:
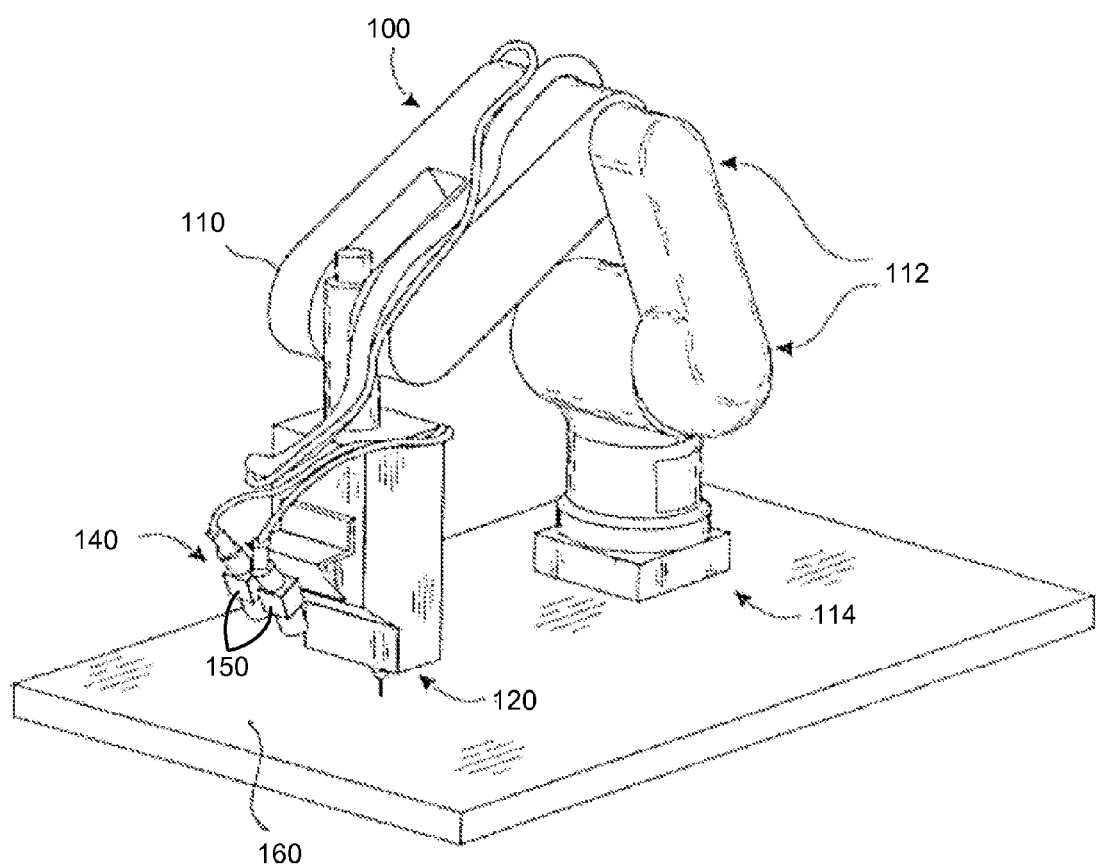
FIG. 1 is a diagram of an image-guided robotic system including a movable arm for positioning and orienting an end-effector tool assembly at targeted locations, according to one embodiment.

With reference to the above-listed drawings, this section describes particular embodiments and their detailed construction and operation. The embodiments described herein are set forth by way of illustration only and not limitation. Those skilled in the art will recognize in light of the teachings herein that, for example, other embodiments are possible, variations can be made to the example embodiments described herein, and there may be equivalents to the components, parts, or steps that make up the described embodiments.

For the sake of clarity and conciseness, certain aspects of components or steps of certain embodiments are presented without undue detail where such detail would be apparent to skilled persons in light of the teachings herein and/or where such detail would obfuscate an understanding of more pertinent aspects of the embodiments.

One or more steps in the methods or procedures described herein may be automated, or autonomous, with some parts requiring manual input. An automated system may include some operator interaction such as activating an ON switch or scheduling an operation, or a system in which hand held tools are used but some mechanism of the system functions autonomously, e.g., without human input, to perform a function. Some of the automated systems described herein may also be robotically assisted or computer/software/machine-instruction controlled.

As one skilled in the art will appreciate in light of this disclosure, certain embodiments may be capable of achieving certain advantages, including some or all of the following: (1) providing a system and method that automatically computes a camera calibration relating a location of multiple camera pairs mounted to a movable arm of a robotic system to a mounting point on the robotic system; (2) providing a system and method that allows a robotic system to accurately position one or more camera pairs above a target location; (3) providing a system and method that automatically moves a position of a robotic arm to calibrate and/or verify the calibration of a camera system relative to the robotic arm; (4) providing a system and method that enables calibration using one button press with no significant user interaction (e.g., if a robotic tool is manufactured/assembled with a reasonable amount of accuracy, a three-dimensional multi-field-of-view vision system can be calibrated using a one button press with no significant user interaction based on predefined coarse robot locations); (5) providing a system and method that saves many hours of process to calibrate and/or teach points in various, including industrial robotic, application; (6) providing a system and method that uses a common coordinate system for multiple camera pairs; (7) providing a system and method that simplifies the use of multiple pairs of stereo cameras; (8) providing a system and method that automatically computes an offset from a robot flange to a tool tip, such as a tip of a punch used to dissect a hair follicle from surrounding tissue; and (9) providing a system and method that allows a robotic system to accurately position and rotate around its tool tip.

FIG. 1 depicts an example image-guided robotic system 100 including a programmable, movable arm 110 for positioning and orienting an end-effector tool assembly 120 at targeted locations on a body surface. The robotic arm facilitates precisely controlled movement of a distal end plate, or "robot flange" (see, e.g., flange 446 in FIG. 4A) in six degrees of freedom (x, y, z, α, β, and γ). Movement of the distal end plate with a high degree of repeatability and accuracy (e.g., to 20 microns) is made possible with pairs of motors and encoders located in respective arm joints 112 of the movable arm 110. A proximal base 114 of the movable arm 110 may be mounted to a table surface 160.

Figure 2:
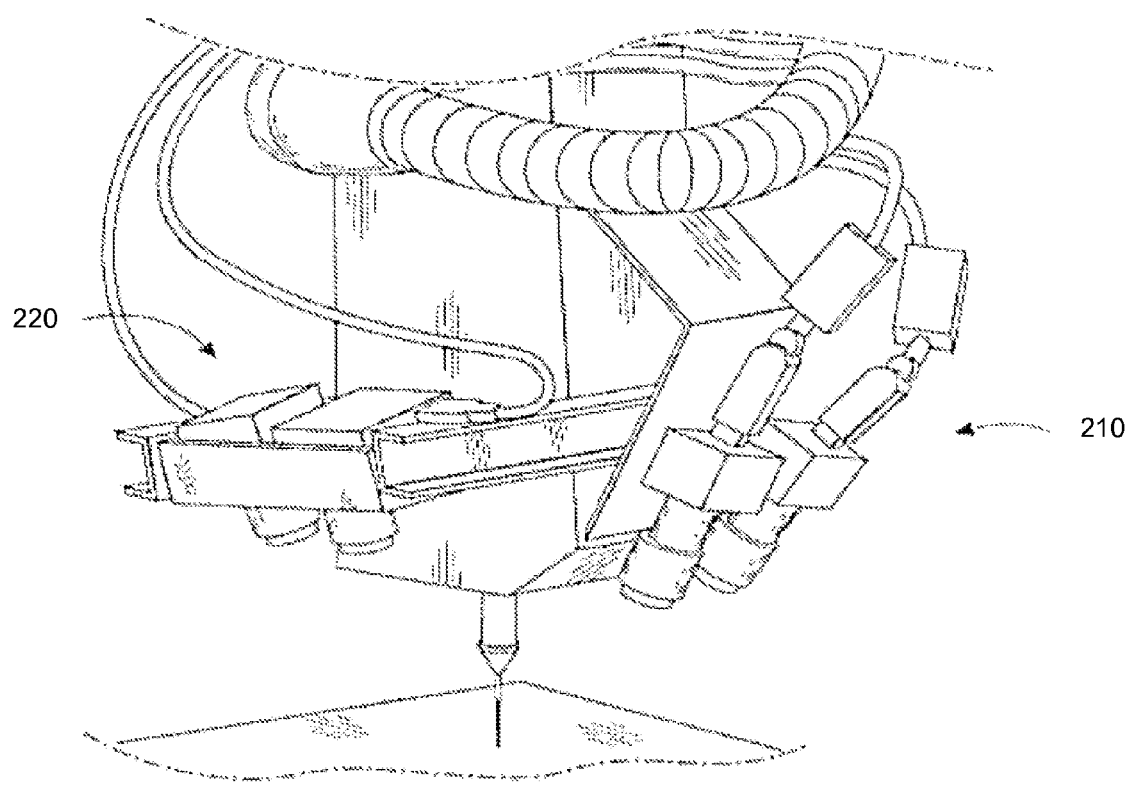
FIG. 2 is an enlarged diagram showing first and second stereo camera pairs secured to the movable arm of FIG. 1, and used to capture image data from multiple fields of view for guiding movement of the arm and the attached end-effector tool assembly.

A variety of end-effector tool assemblies may be attached to the distal end plate for performing various procedures on a human or animal patient. For example, some end-effector embodiments may perform diagnostic or therapeutic medical procedures that take advantage of the ability of a robotic arm to rapidly and precisely position an attached tool (e.g., a needle) or tool-assembly at desired locations of a patient. Additionally, various end-effector assemblies may themselves include moving, controllable parts. In one example (not shown), the end-effector tool assembly includes a reciprocating needle used for delivering precisely targeted, repetitive injections through the dermis. In the example shown in FIGS. 1 and 2, the end-effector tool assembly 120 includes a three-part tool designed for harvesting and implanting hair follicles (or follicular units) on a human scalp. Additional details of an example of the end-effector tool assembly 120 are described with respect to FIG. 3.

Movement of the arm 110 is governed by a system controller (see, e.g., robot controller 430 in FIG. 4A), in response to control signals derived from image data acquired by one or more camera systems 140 that may be mounted to the distal end of the movable arm 110. The one or more camera systems 140 may be directly attached or coupled to the movable arm 110 or may be attached to the end-effector tool assembly, which is directly or indirectly attached to the movable arm 110. The camera system 140 may comprise a single camera, a pair of stereo cameras 150, or more than one pair of stereo cameras. According to a preferred embodiment, two pairs of stereo cameras 210 and 220 (FIG. 2) are used to capture differing (e.g., broader and narrower) fields of view. The description below is made with reference to hair transplantation procedures. It will be understood by skilled persons that the systems and methods described herein are equally applicable to other types of systems and applications, including various medical and industrial applications.

The stereo camera pairs 210 and 220 provide the position and orientation information that allows the robotic system 100 to identify and track hairs for dissection. For example, the stereo camera pair 210 may include relatively high-magnification cameras that provide a detailed view of the hair follicles (e.g., the detailed view may be used, to locate and track individual hair follicles for dissection) whereas the stereo camera pair 220 includes relatively low-magnification cameras that provide an overview of the harvest area that is used for tracking fiducials (see, e.g., fiducials 2622 in FIG. 26) and planning harvest spacing and direction. According to one embodiment, the stereo camera pair 210 comprises left and right high-magnification cameras with a diagonal field of view of approximately 2.5 cm and stereo camera pair 220 comprises left and right low-magnification cameras with a diagonal field of view of approximately 5 cm. Each stereo camera pair 210 and 220 provides a left and right view of the scalp area, which are used to determine a three-dimensional position and orientation of individual hair follicles. In still further embodiments, a single camera may be used to capture a first (e.g., broad) field of view and a second camera may be used to capture a second (e.g., narrow) field of view.

Figure 3:
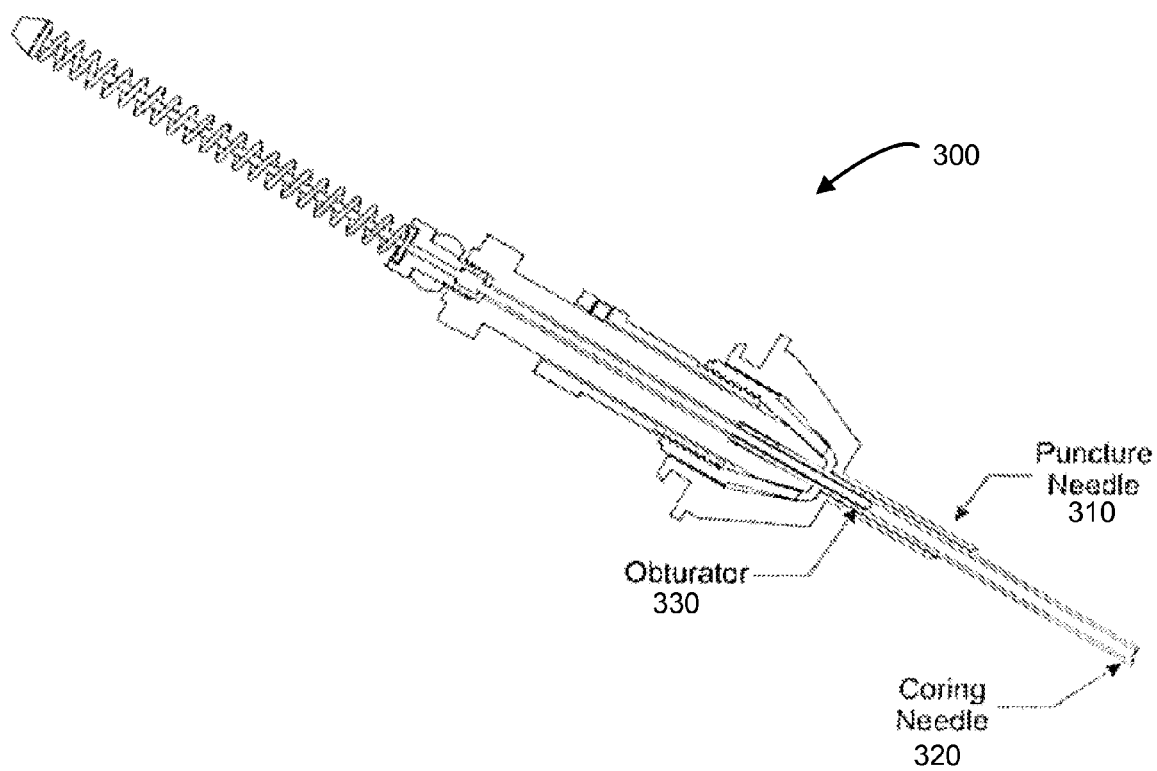
FIG. 3 is a cross-sectional view of an end-effector tool for follicular unit harvesting, recipient site incision, and graft placement, according to one embodiment.

Hair transplantation generally includes three steps: follicular unit harvesting, recipient site incision, and graft placement. In some situations, the efficiency of the surgery can be enhanced if these functions are accomplished with a single tool. FIG. 3 shows an example of a three-part tool 300 for accomplishing the three functions which could be utilized in some embodiments. The three coaxial elements shown in the example of FIG. 3 are an outer cannula ("puncture needle") 310 with a sharp bevel cut that is used for making the recipient-site incision, a second cannula ("coring needle") 320, that may be positioned for movement inside the outer needle and is used for dissecting around the donor graft, and an obturator 330 that may be positioned for movement inside the second cannula 320 and is used for positioning the graft at the appropriate depth in the recipient site. For harvesting, the second cannula 320 may cut the tissue (for example, by rotating or by a quick thrust) while being advanced to the desired depth for separating the follicular unit from the surrounding tissue. The graft is then captured within this cannula 320 and extracted, sometimes with an assistance of a vacuum. For recipient site incision, the outer cannula 310 is advanced into a tissue and is used to make an incision at the desired location with the desired orientation and depth. The obturator 330 may be used to hold the graft at the desired depth while the cannula 310, is retracted. If should be understood that various different tools, including independent harvesting and implanting needles/punches may be used in various embodiments and applying different methods of harvesting and/or implantation.

Figure 4A:
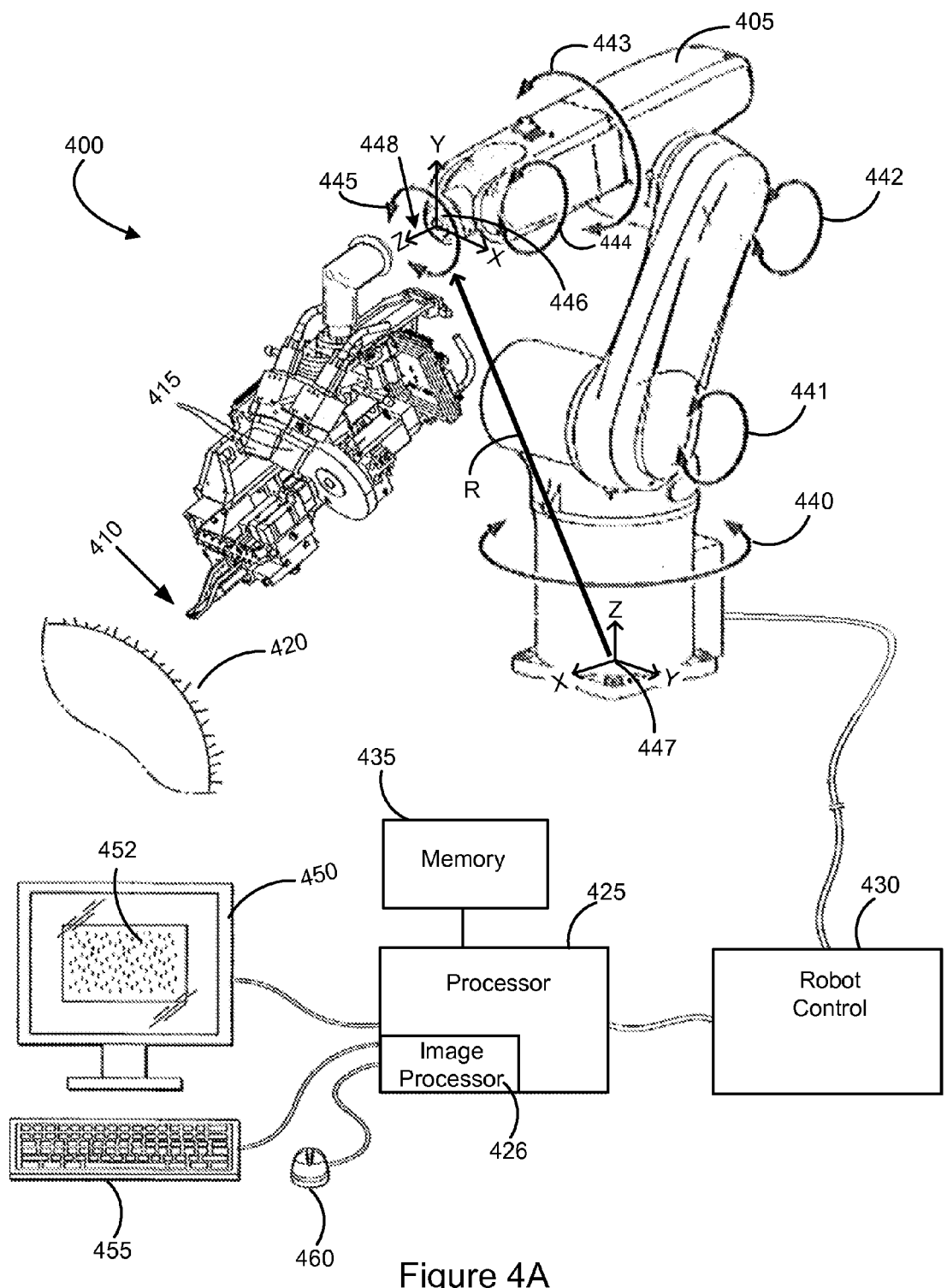
FIG. 4A is a diagram of an image-guided robotic system illustrating operational components of the system and a relationship between a tool frame and a fixed world origin frame.

FIG. 4A illustrates an example of a robotic system 400 for harvesting and/or implanting follicular units into a body surface, such as the scalp. The system 400 includes a movable arm 405 to which is coupled a harvesting or implanting tool 410. The tool 410 may comprise a tool similar or identical to the end-effector tool assembly 120 described with reference to FIGS. 1-3. The tool 410 is preferably mounted to a distal end plate or flange 446 of the movable arm 405, but is illustrated detached from the movable arm 405 in FIG. 4A to illustrate the relative orientation of a robot frame or coordinate system 448. Various motors and other movement devices may be incorporated to enable fine movements of an operating tip of the tool 410 in multiple directions. The robotic system 400 further includes a camera system or image acquisition device 415 (e.g., a camera system similar or identical to the camera systems 140, 210, and 220 described with reference to FIGS. 1 and 2), which may be mounted in a fixed position, or coupled (directly or indirectly) to the movable arm 405 or other controllable motion device. The operating tip of the tool 410 is shown positioned over a body surface 420, in this case a part of a patient's scalp having hair follicles thereon.

The robotic system 400 includes a processor 425 that is configured to be operatively coupled to the camera system 415, a robot controller 430, and a memory 435. The processor 425 comprises an image processor 426 for processing images obtained from the camera system 415. The image processor 426 may be a separate device or it may be incorporated as a part of the processor 425. Image data acquired by the camera system 415 is processed via the image processor 426, the processor 425, or both, and the processor 425 provides control signals to the robot controller 430 for directing movement of the arm 405. In particular, images are acquired from the camera system 415 at a desired magnification (e.g., in a range of 6× to 10× in one embodiment) and duty cycle (e.g., 30 hertz in one embodiment). The acquired images are digitized using image segmentation techniques implemented in software stored in the memory 435 in order to identify the position(s) and orientation(s) of objects of interest. U.S. Patent Publication No. 2007/0106306 of Bodduluri et al., which is hereby incorporated by reference in its entirety, describes additional details of an automated system (e.g., for harvesting or implating follicular units) that positions a movable arm based, at least in part, on processed images acquired by one or more cameras.

The processor 425 instructs the various movement devices of the robotic system, including the movable arm 405 and the tool 410, acting, for example, through the controller 430. The controller 430 may be operatively coupled to the movable arm 405 and configured to control the motion of the arm 405, including the motion based on the images or data acquired by the camera system 415. Alternatively, the controller 430 may be incorporated as a part of the processor 425, so that all processing and controls of all movements of all the various tools, the movable arm 405 and any other moveable parts of the assembly, including those based on the images or data acquired by the camera system 415, are concentrated in one place.

The movable arm 405 includes six rotational axes 440-445 having associated therewith one or more motors (e.g., one motor may cause rotation about one axis or multiple axes or multiple motors may work together to cause rotation about a single axis) and encoders. The movable arm 405 may include fewer or more than six rotational axes. In response to instructions received from the processor 425, the controller 430 generates one or more control signals that cause one or more motors to cooperatively move the tool 410 to a desired position and orientation. In other words, the controller 430 coordinates the rotation of the movable arm 405 about one or more of its rotational axes 440-445 to bring the distal end plate or flange 446 having the tool 410 mounted thereto to a desired position (x, y, z, α, β, and γ) relative to an arbitrary world origin frame or coordinate system 447.

Euler angles α, β, and γ, which are similar in concept to yaw, pitch and roll, facilitate representing a spatial orientation of any frame or coordinate system as a combination of rotations relative to the world origin frame 447. For example, FIG. 4A illustrates a robot frame or coordinate system 448 having an x, y, z coordinate origin at a center point of the flange 446 with the z-axis orthogonal to the flange 446. The world origin frame 447 illustrated in FIG. 4A has an x, y, z coordinate origin at a center point of the base of the movable arm 405 with the z-axis orthogonal to a mounting surface (e.g., the z-axis of the world origin frame 447 points "straight up"). Although the world origin frame 447 is illustrated at a center point of the base of the movable arm 405 in FIG. 4A, the world origin frame 447 may be located at any arbitrary fixed location. To describe the orientation of the robot frame 448 relative to the world origin frame 447, a line of nodes may be defined as the intersection of the x-y coordinate planes of the world origin and robot frames 447 and 448. In other words, the line of nodes is the line perpendicular to the z-axes of the world origin and robot frames 447 and 448. Then, angle α can be defined as the angle between the x-axis of the world origin frame 447 and the line of nodes, angle β can be defined as the angle between the z-axes of the world origin and robot frames 447 and 448, and angle γ can be defined as the angle between the line of nodes and the x-axis of the robot frame 448.

According to one embodiment, the position of the movable arm 405, such as the robot frame 448 illustrated in FIG. 4A, in relation to the world origin frame 447 is given by a robot-position transformation matrix R of the form illustrated in Equation 1. The robot-position transformation matrix R is conceptually illustrated in FIG. 4A by the arrow extending from the world origin frame 447 to the robot frame 448.

$$R = \begin{bmatrix} r_{00} & r_{01} & r_{02} & x \\ r_{10} & r_{11} & r_{12} & y \\ r_{20} & r_{21} & r_{22} & z \\ 0 & 0 & 0 & 1 \end{bmatrix} \quad \text{Equation 1}$$

In Equation 1, the upper-left three-by-three rotation sub-matrix (e.g., sub-matrix $r_{00}$ through $r_{22}$) represents an orthonormal rotation relating an orientation of the movable arm 405 at a given position (e.g., the robot frame 448 illustrated in FIG. 4A) to a reference orientation, such as the world origin frame 447, and the first three elements of the right-most column (e.g., sub-matrix x, y, z) represents a three-dimensional offset between the position of the movable arm 405 and the reference position. The value of each element of the rotation sub-matrix (e.g., elements $r_{00}$ through $r_{22}$) is derived from Euler angles α, β, and γ, such as by a rotation of α, β, and γ about the z-axis, y-axis, and z-axis, respectively. In other words, only three elements of the rotation sub-matrix are independent (e.g., angles α, β, and γ) and the elements $r_{00}$ through $r_{22}$ of the rotation sub-matrix are built up from various sines and cosines of angles α, β, and γ, which is known to those skilled in the art. Additional details regarding generating the rotation sub-matrix from Euler angles α, β, and γ can be found in Chapter 1, "Homogeneous Transformations" from "Robot Manipulators: Mathematics, Programming and Control", by Richard Paul, MIT Press, 1981, which is hereby incorporated by reference in its entirety. The controller 430 preferably stores a current position of the movable arm 405 (e.g., the robot frame 448 illustrated in FIG. 4A) in a controller memory or another memory, such as the memory 435. Thus, the processor 425 may perform a look-up (e.g., interrogate or query the controller 430 or the memory 435) to determine a current position of the movable arm 405 as defined by the robot-position transformation matrix R.

The robotic system 400 may further include any number of input or output devices, such as a monitor 450, keyboard 455, and mouse 460, A magnified image 452 of the body surface 420 is illustrated on the imaging display or monitor 450. In addition, the system 400 may comprise other tools, devices, and components useful in harvesting and/or implantation of the hair follicles, or in hair treatment planning. Various parts of the system allow an operator to monitor conditions and provide instructions, as needed. For example, the system 400 may further comprise an interface (not shown) adapted to receive image data. The processor 425 may interact with the camera system 415 via the interface. The interface may include hardware ports, cables, leads, and other data transmission means, or it may comprise a computer program.

Some non-limiting examples of the camera system 415 illustrated in FIG. 4A include one or more cameras, such as any commercially available cameras. An example image acquisition or imaging device may be held, for example, by the movable arm 405, or by any other mechanism or means. Of course, various image acquisition devices or a combination of several devices could be used with any of the examples described herein. For example, 3D vision can be achieved in multiple ways, including without limitation using multiple cameras, or using a single camera paired with an external sensor, such as a laser range finder. The cameras used may be of various combinations of different sizes, color/grayscale, visible light/IR or UV, etc. While the camera system 415 preferably comprises a device that takes still images, the camera system 415 may also comprise a device capable of real time imaging (e.g., a webcam capable of continuously streaming real time or video information), and/or the camera system 415 may also have a video recording capability (e.g., a camcorder). While stereo or multi-view imaging devices are useful in the present disclosure, it is not necessary to employ such geometries or configurations, and the present disclosure is not so limited. Likewise, the camera system 415 may be digital or analog. For example, the camera system 415 could be an analog TV camera that acquires an initial image, which is then processed into a digital image (for example, via an analog-to-digital device like a commercial-off-the-shelf frame grabber) for further use in the methods of the present disclosure. The camera system 415 may be coupled to the processor 425 to control the imaging operation and to process image data.

The processor 425 preferably operates as a data processing device, which, for example, may be incorporated into a computer. The processor 425 may include a central processing unit or parallel processor, an input/output interface, a memory with a program, wherein all the components may be connected by a bus. Further, the computer may include an input device, a display, and may also include one or more secondary storage devices. The bus may be internal to the computer and may include an adapter for receiving a keyboard or input device or may include external connections.

The processor 425 may execute a program that may be configured to include predetermined operations and methods, such as one or more of the methods 800, 900, 1000, 1100, 1400, 1500, 1600, 1900, and 2000 in FIGS. 8, 9, 10A, 11, 14, 15, 16, 19, and 20. The processor 425 may access the memory 435 in which may be stored at least one sequence of code instructions comprising the program for performing predetermined operations. The memory 435 and the program may be located within the computer or may be located external thereto. By way of example, and not limitation, a suitable image processor 426 may be a digital processing system that includes one or more processors or other type of device. For example, a processor and/or an image processor may be a controller or any type of personal computer (PC). Alternatively, the processor may comprise an Application Specific Integrated Circuit (ASIC) or Field Programmable Gate Array (FPGA). It will be understood by skilled persons that the processor and/or the image processor for use with the present disclosure is programmed and configured to perform various image processing techniques, for example, segmentation, edge detection, object recognition, and selection. These techniques are generally known and therefore are not separately described here.

The methods described herein may be implemented on various general or specific purpose computing systems. In certain embodiments, the methods of the present application may be implemented on a specifically configured personal computer or workstation. In other embodiments, the methods may be implemented on a general-purpose workstation, including one connected to a network. Alternatively or additionally, the methods of the disclosure may be, at least partially, implemented on a card for a network device or a general-purpose computing device. The processor 425 and/or the image processor 426 may also include memory, storage devices, and other components generally known in the art and, therefore, they do not need to be described in detail here. The image processor 426 could be used in conjunction with various manual, partially automated and fully automated (including robotic) hair transplantation systems and devices, including but not limited to systems for hair harvesting, implantation or transplantation.

The imaging display device 450 may comprise a high resolution computer monitor which may optionally be a touch screen. The imaging display may allow images, such as video or still images, to be readable and for follicular units, and parts thereof, to be visualized. Alternatively, the imaging display device 450 can be other touch sensitive devices, including tablet, pocket PC, and other plasma screens. The touch screen may be used to modify the parameters of the hair transplantation procedure, directly through the image display device.

Methods, apparatus and systems consistent with the disclosure may be carried out by providing a modification interface, or user modification interface, including clickable icons, selection buttons in a menu, dialog box, or a roll-down window of an interface that may be provided to feed into the computer. According to another embodiment, the imaging display device 450 may display the selection window and a stylus or keyboard for entering a selection, for example, directly on the display itself. According to one embodiment, commands may be input via the modification interface through a programmable stylus, keyboard, mouse, speech processing system, laser pointer, touch screen, remote control device, or other input mechanism. Alternatively, the modification interface may comprise a dedicated piece of hardware. In some embodiments, the selections or adjustment made through the modification interface may be executed by code instructions that may be executed on a processor, for example, the computer processor.

Figure 4B:
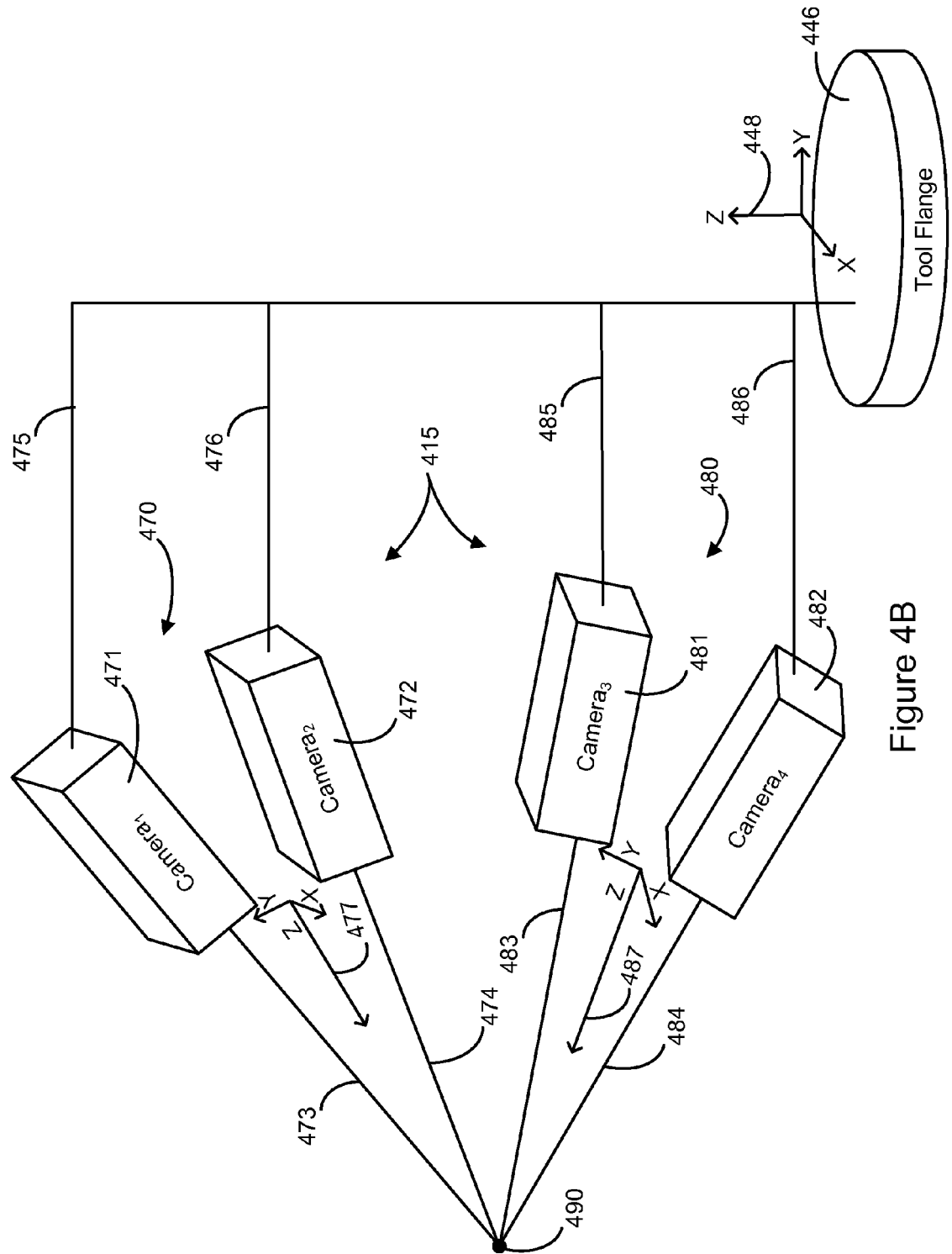
FIG. 4B is a block diagram illustrating a relationship between a first and second camera system's coordinate system and a robot's coordinate system.

FIG. 4B is a block diagram illustrating a relationship between a first and second camera system's coordinate system and a robot's coordinate system. In FIG. 4B, the camera system 415 comprises two pairs of stereo cameras 470 and 480, which may be used to capture differing (e.g., broader and narrower) fields of view. For example, the stereo camera pair 470 may include first and second cameras 471 and 472 having a relatively high-magnification and the stereo camera pair 480 may include first and second cameras 481 and 482 having a relatively low-magnification. The optical axes 473 and 474 of the first and second cameras 471 and 472 and the optical axes 483 and 484 of the first and second cameras 481 and 482 are preferably not installed or maintained in parallel, but are slightly verged or angled toward each other (e.g., by about 10 degrees). The first and second cameras 471 and 472 are preferably aligned to have a common axis (e.g., horizontal x-axis or vertical axis y-axis) to facilitate determining a three-dimensional position of objects within a field of view of the stereo camera pair 470. Likewise, the first and second cameras 481 and 482 are preferably aligned to have a common x-axis or y-axis.

A three-dimensional position of an object within a field of view of the stereo camera pair is determined, for example, by comparing the differences between the x,y position offsets of the object in the respective camera frames (e.g., left and right images). For example, after a stereo camera pair (e.g., one of the stereo camera pairs 470 or 480) takes a picture of a point 490, a three-dimensional location of the point 490 in a coordinate system of the camera pair is computed from the two-dimensional locations of the point 490 in the images captured by the first and second cameras in the camera pair (e.g., "left hand" and "right hand" cameras). In other words, because the respective camera images are aligned horizontally (or vertically), the same objects should appear in the same horizontal scan lines (or vertical scan lines) of the two images. Moreover, because a depth of an object being imaged relative to the camera lenses is within a known range (e.g., established by the focal lengths of the respective cameras), a selected object in a first image (e.g., a hair follicle) can be matched to itself in the second image (to thereby align the images with each other) by calculating an effective depth of the object when paired with the possible candidate objects in the second image (e.g., in the same scan line) to determine which "pair" has a calculated depth in the possible range. Additional details regarding determining a three-dimensional location of an object captured by a stereo camera pair can be found in Chapter 12, "Learning OpenCV: Computer Vision with the OpenCV Library", by Grary Bradski and Adrian Kaehler, published by O'Reilly, 2008, which is hereby incorporated by reference in its entirety.

The stereo camera pairs 470 or 480 are preferably rigidly mounted or attached, for example, to the robot tool flange 446 (as conceptually illustrated by physical mounts 475, 476, 485, and 486) so that their relationship with respect to one another is fixed. In other embodiments, the cameras may be attached at other locations, for example, somewhere else on the robotic arm, or they may be fixed in 3D space external to the system. Coordinates of objects within the field of view of the camera pair 470 are determined (e.g., via one or more of processors 425 or 426 in FIG. 4A or processors 550, 610, 620, and 650 in FIGS. 5 and 6) and reported in a camera frame or coordinate system 477 associated with the camera pair 470. Similarly, coordinates of objects within the field of view of the camera pair 480 are determined and reported in a camera frame or coordinate system 487 associated with the camera pair 480. According to one embodiment, the z-axis of the coordinate system 477 bisects the angle between optical axes 473 and 474, and the y-axis of the coordinate system 477 extends between centers of the lenses of the cameras 471 and 472. Likewise, the z-axes of the coordinate system 487 bisects the angle between optical axes 483 and 484, and the y-axis of the coordinate system 487 extends between centers of the lenses of the cameras 481 and 482.

According to one embodiment, the coordinates of the point 490 are reported by a camera pair in an array v of the form illustrated in Equation 2. The camera pair or a processor associated with the camera pair preferably stores the coordinates of the point 490 in a memory, such as the memory 435. Thus, the processor 425 may perform a look-up (e.g., interrogate or query the camera pair 470 or 480 or the memory 435) to determine the coordinates of the point 490 (or another object). The point 490 may represent an individual calibration feature, such as one of the calibration features illustrated with respect to FIGS. 7A-7C.

$$v = \begin{bmatrix} x \\ y \\ z \\ 1 \end{bmatrix} \quad \text{Equation 2}$$

Figure 8:
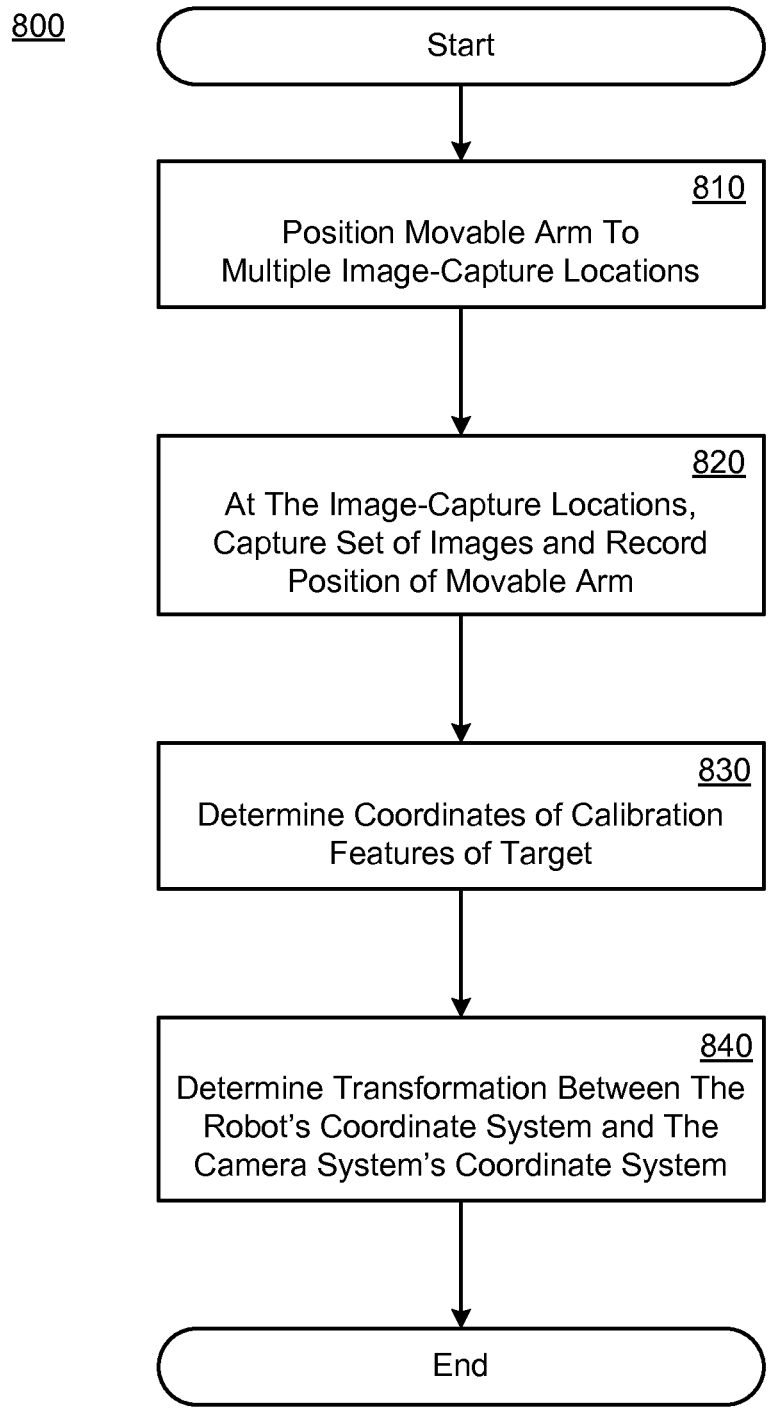
FIG. 8 is a flow diagram of a method for determining a transformation between a robot's coordinate system and a camera's coordinate system, according to one embodiment.

To help precisely position and orient an object secured to the tool flange 446 (e.g., a needle) relative to another object, such as a hair follicle extending out of a patient's skin surface, it may be desirable to calibrate or determine a transformation between the camera coordinate system 477 of the camera pair 470 and the robot coordinate system 448 and the camera coordinate system 487 of the camera pair 480 and the robot coordinate system 448, which is described in greater detail with respect to FIG. 8. Determining a transformation between a robot's coordinate system and a camera system's coordinate system may be useful in a wide variety of applications, including mobile robotics, medical robotics, and industrial robotics. In addition, it may be desirable to calibrate or determine a mapping between the camera coordinate systems 477 and 487, which is described in greater detail with respect to FIG. 10A. Determining a mapping that allows multiple camera systems to report common coordinates may be useful in any environment where multiple camera systems are used, such as mobile robotics and surveillance. Moreover, it may be desirable to calibrate or determine an offset between the tool flange 446 and a tool tip, which is described in greater detail with respect to FIGS. 14-16 and 19-20. Automatically computing a tool tip location in three-dimensions may be useful in any environment where precise position and rotation of a tool tip is desired.

After determining the transformation between the robot coordinate system 448 and the camera coordinate systems 477 and 487, it is possible to precisely position the movable arm 405 relative to an object within the field of view of the camera pair 470, 480, or both, based on the coordinates of the object as determined in the camera coordinate system 477 or 487. In other words, after capturing an image of a hair follicle using the camera pair 470 or 480, the processor 425 can determine a position of the hair follicle relative to the movable arm 405 and generate instructions that cause the controller 430 to move the arm 405 to a desired position and orientation (e.g., rotate the needle tip and align the needle with a hair follicle so the needle can travel down the shaft to harvest the hair follicle).

After determining a mapping between the camera coordinate systems 477 and 487, it is possible to determine a position of a first object within the field of view of the camera pair 470 relative to a position of a second object within the field of view of the camera pair 480. For example, if the stereo camera pair 480 (having a relatively low-magnification) captures an image of a fiducial or other target surrounding a work area and the stereo camera pair 470 (having a relatively high-magnification) captures an image of a hair follicle itself, it is possible to determine a position of the hair follicle relative to the fiducial (e.g., to help plan a path across a patients scalp). While the fiducial may be located on a skin tensioner device that is placed on the patient's skin (see, e.g., fiducials 2622 in FIG. 26), the fiducal may comprise another hair follicle, a scar, an artificial marking (e.g., a dot) placed on the skin, or another natural or artificial landmark.

Figure 5:
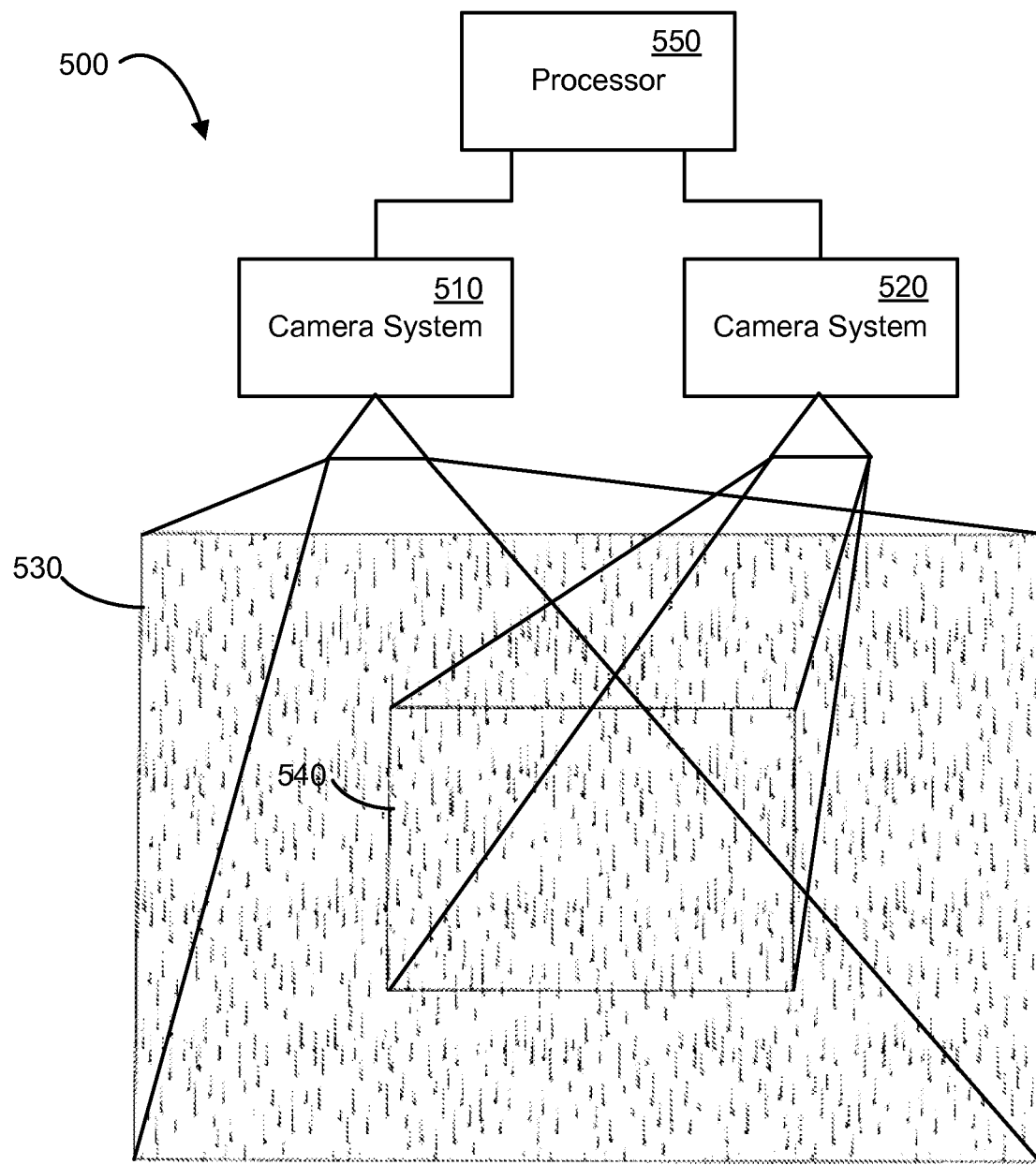
FIG. 5 is a block diagram of a machine vision subsystem, which may be implemented as part of a robotic hair transplantation machine, according to one embodiment.

FIG. 5 is a block diagram of a machine vision subsystem 500, according to one embodiment. The machine vision subsystem 500 may be part of a larger system, such as a robotic hair transplantation machine, such as the robotic system 400 (FIGS. 4A and 4B). The machine vision subsystem 500 comprises multiple camera systems. Two such camera systems 510 and 520 are illustrated in FIG. 5. Each camera system 510 and 520 is preferably a stereo pair of cameras, although that need not be the case. The camera systems 510 and 520 may be on a robotic arm, such as the robotic arm 110 illustrated in FIG. 1 or the movable arm 405 for hair transplantation shown in FIG. 4A. However, the machine vision subsystem 500 may be part another system used for a different application. The machine vision subsystem 500 may comprise additional camera systems not shown.

The camera systems 510 and 520 have fixed locations relative to each other, so that a transformation relating one camera system to the other is fixed. Such is the case in the robotic arm 110 and 405 illustrated in FIGS. 1 and 4A. Such is generally the case for robotic arms utilized for hair transplantation. As the robotic arm moves, the camera systems 510 and 520 move together, essentially maintaining their fixed positional relationship. The term "fixed" as used herein to modify the positional relationship of the camera systems 510 and 520 permits some minor relative movement, such as random vibration and minor slippages of the camera systems. So long as the minor relative movements are small enough that a useful camera-system-to-camera-system transformation can be determined and utilized, the camera systems are sufficiently "fixed." Generally speaking, variations less than some small measurement, such as a pixel size of a camera, are insignificant, as are larger random variations that can be averaged out when the transformation is determined.

The camera systems 510 and 520 have respective fields of view 530 and 540. One camera may have a larger field of view than the other, such as illustrated in FIG. 5, where the field of view 530 of the camera system 510 is wider than the field of view 540 of the camera system 520. The fields of view 530 and 540 overlap fully or partially, such that there are locations "seen" by both camera systems. The camera systems 510 and 520 may have different resolutions. For example, the camera system 510 may have a lower resolution than the camera system 520. In hair transplantation applications, the camera system 510 with a lower resolution and wider field of view can be used to guide the robotic tool to general areas of the scalp, while the camera system 520 with a higher resolution and narrower field of view can be used to guide the robotic tool to specific follicles for hair extraction and to precise locations for implantation.

The machine vision subsystem 500 also comprises a processor 550 that receives image data from the camera systems 510 and 520 and processes that data. The processing performed by the processor 500 may include converting coordinates in the coordinate system of one camera system into that of the other, determining what that conversion should be, or any other image processing. The processor 550 may be any type of processor, such as, for example, a general-purpose microprocessor or digital signal processor (DSP). The machine vision subsystem 500 may also comprise one or more memories (not shown) for storing programs executed by the processor 550 and/or data processed or generated by the processor 550.

Because the fields of view 530 and 540 overlap at least partially, objects and locations in the overlapping volume can be imaged by both camera systems. When the camera systems 510 and 520 generate respective images containing a common feature (e.g., seeing the same thing, even if from different perspectives, scales, resolutions, etc.) and the camera systems 510 and 520 have not moved appreciably with respect to the feature between the times at which those respective images were captured, then the respective images are said to be "corresponding." Appreciable movement in this context is both more than some small measurement, such as a pixel size, and large enough that the positional difference is not averaged out by the plurality of image data that are used in the computations. Corresponding images from the first and second camera systems 510 and 520 may be taken simultaneously or nearly simultaneously, but that need not be the case. As used here, "corresponding features" refers to the same feature in corresponding images. Corresponding features from different camera systems will generally have different local coordinates in each camera system because of each camera systems own unique position, pointing direction, scale, zoom, and/or resolution.

Figure 6:
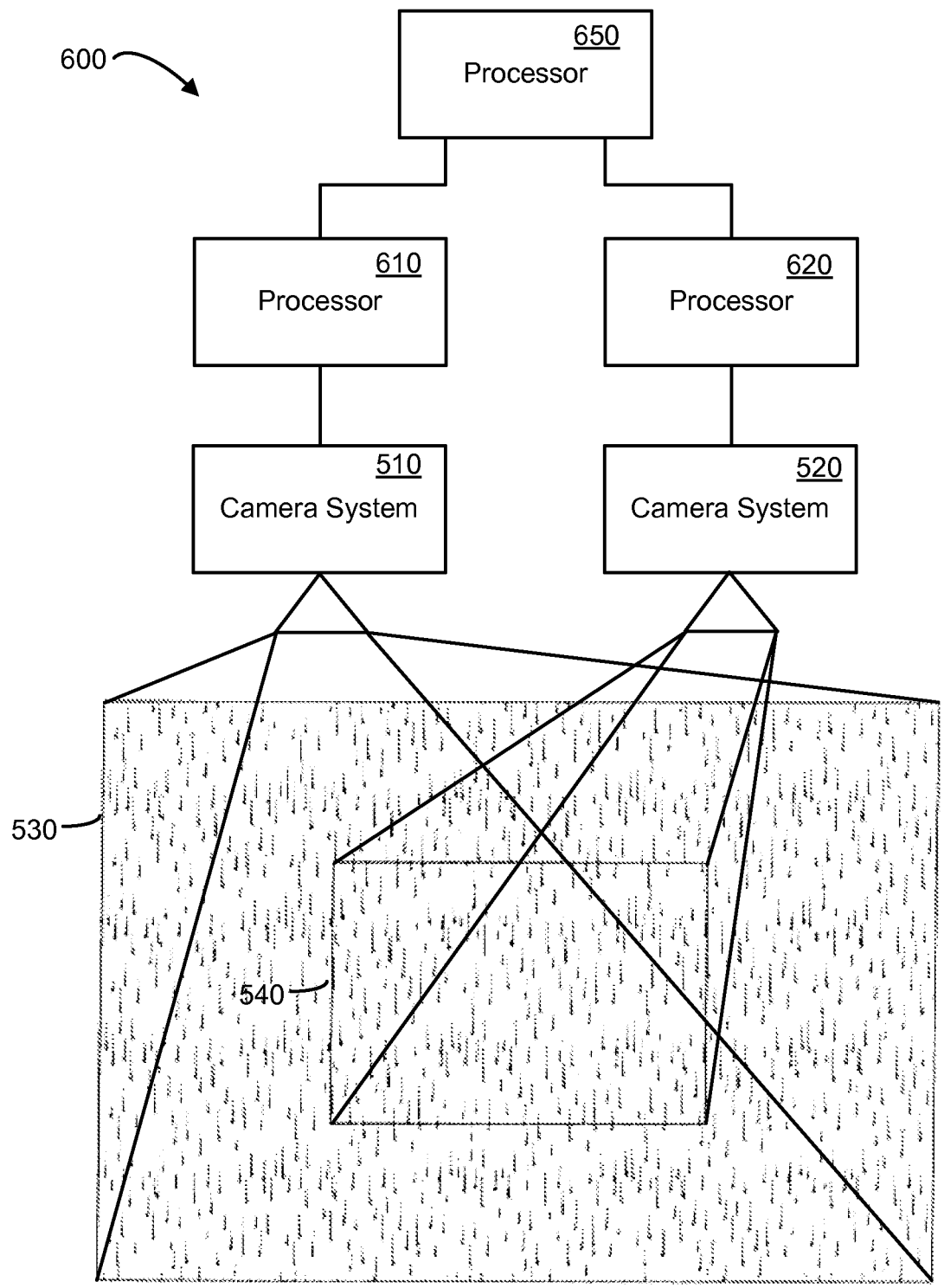
FIG. 6 is a block diagram of a machine vision subsystem, which may be implemented as part of a robotic hair transplantation machine, according to another embodiment.

FIG. 6 is a block diagram of a machine vision subsystem 600, according to another embodiment. The machine vision subsystem 600 may be part of a larger system, such as a robotic hair transplantation machine, such as the robotic system 400 (FIGS. 4A and 4B). The machine vision subsystem 600 in FIG. 6 is like the machine vision subsystem 500 in FIG. 5 except that the machine vision subsystem 600 additionally includes a processor 610 associated with the camera system 510 and a processor 620 associated with the camera system 520. The processors 610 and 620 may be integrated into the camera systems 510 and 520, respectively, or they may be separate. The processors 610 and 620 may perform some of the processing that the single processor 550 performs in the machine vision subsystem 500 in FIG. 5. A processor 650 is a central processor in the machine vision subsystem 600 and may perform other processing not performed by the camera-specific processors 610 and 620. For example, each of the processors 610 and 620 may generate local coordinates of features in its associated camera system's local coordinate system, while the central processor 650 converts between those two local coordinate systems or between a local camera system's coordinate system and another coordinate system such as a robot's coordinate system.

Figure 7A:
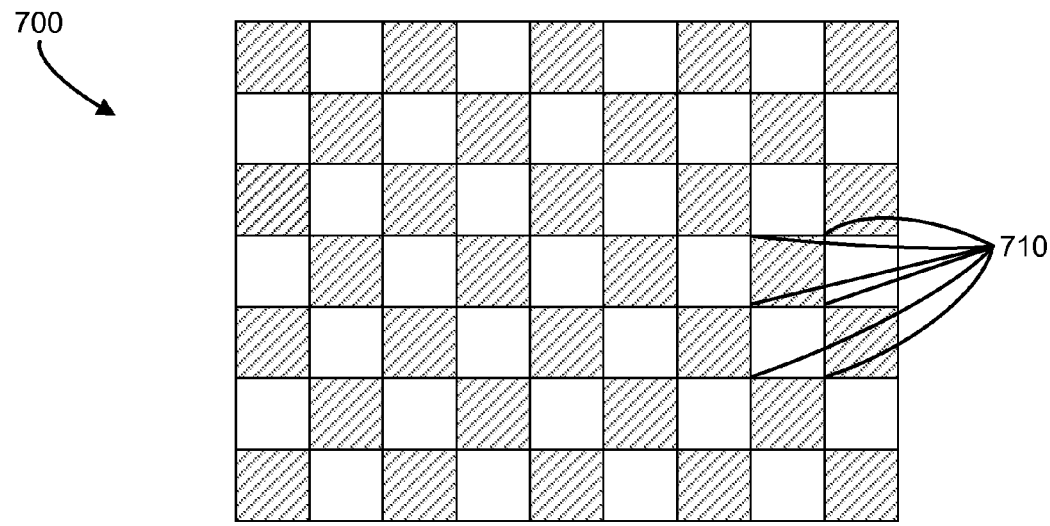
FIGS. 7A-7C are diagrams illustrating various example calibration features.
Figure 7B:
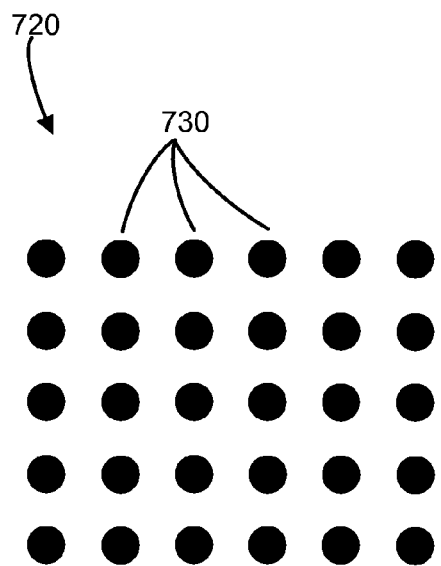
Figure 7C:
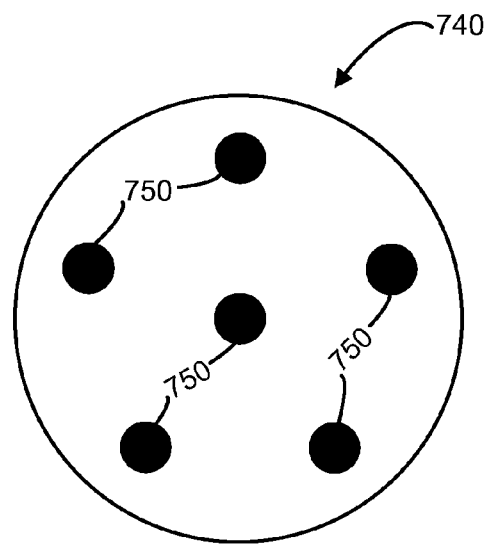

FIGS. 7A-7C are diagrams illustrating various example calibration features that may be used when calibrating a camera coordinate system to a robot coordinate system and one camera coordinate system to another camera coordinate system. FIG. 7A illustrates a checkerboard calibration target 700 including a 7×9 pattern having 48 internal corners 710. The internal corners 710 define individual calibration features (e.g., one of the internal corners 710 may represent the point 490 illustrated in FIG. 4B) and are preferably spaced a predetermined distance from one another. According to one embodiment, the checkerboard calibration target 700 comprises a chrome-on-glass target. Checkerboard calibration targets according to other embodiments may include additional or fewer internal corners. FIGS. 7B and 7C illustrate dot-centroid calibration targets 720 and 740. The dot-centroid calibration target 720 includes 30 dot-centroids 730, which define individual calibration features and are preferably spaced a predetermined distance from one another. Likewise, the dot-centroid calibration target 740 includes 6 dot-centroids 750, which define individual calibration features and are preferably spaced a predetermined distance from one another. Dot-centroid calibration targets according to other embodiments may include additional or fewer dot-centroids.

FIG. 8 is a flow diagram of a method 800 for determining a transformation between a robot's coordinate system and a camera's coordinate system, according to one embodiment. To help precisely position and orient an object, such as the harvesting or implanting tool 410 (FIG. 4A), secured to the tool flange 446 relative to another object, such as a hair follicle extending out of a patient's skin surface, the method 800 may be used to calibrate, and thereby generate the information to compensate for, the positional and rotational offsets between the robot coordinate system 448 (FIG. 4B) and one or more of the camera coordinate systems 477 and 487. As an initial matter, a target, such as one of the calibration targets 700, 720, and 740 (FIGS. 7A-7C), is positioned within the field of view of a camera system, such as the camera system 415 (FIG. 4B), such that the calibration features are within focus. This may be accomplished by placing the target within the field of view or by moving the camera system until the target is within the field of view. The camera system may comprise a single camera, a pair of stereo cameras, or more than one pair of stereo cameras (e.g., one or more of the camera pairs 470 and 480 illustrated in FIG. 4B).

At step 810, a movable arm of the robot (e.g., the movable arms 110 or 405 in FIG. 1 or 4A) is positioned about the target to multiple image-capture locations such that the target is within the field of view of the camera system (and preferably in focus) at individual image-capture locations. The movable arm is preferably rotated about and translated relative to the target from one image-capture location to another image-capture location. For example, the individual image-capture locations may lie approximately on a surface of a sphere having a center point approximately coincident with the target. In other words, the movable arm rotates along the surface of a sphere while looking at the target, which is positioned at the center of the sphere. Rotating the movable arm around the target in addition to translating the movable arm relative to the target allows the system to determine a transformation that converts a small motion in a camera system's coordinate system to a small motion in a robot's coordinate system. While the individual image-capture locations may lie on random points of a sphere or hemisphere, the image-capture locations may be confined to a sector of the sphere. For example, assuming an axis of the camera system starts at a position that is orthogonal to the target (e.g., the checkerboard calibration target 700), the movable arm may rotate up to approximately 45 degrees in each direction. In certain embodiments, the movable arm is moved radially with respect to the target from one image-capture location to another image-capture location (e.g., closer to or further away from the target). The movable arm may be positioned to any number of image-capture locations at step 810, but the method 800 is preferably implemented using three to six image-capture locations. According to one embodiment, the image-capture locations are predetermined and stored in a memory (e.g., memory 435 in FIG. 4A).

At the individual image-capture locations, the method 800 captures a set of images of the target (e.g., one or more images) using the camera system and records, in the robot's coordinate system (e.g., the coordinate system 448 in FIGS. 4A and 4B), a position of the movable arm (step 820). For example, at the individual image-capture locations, a processor, such as the processor 425 (FIG. 4A), may instruct the camera system to capture one or more images of the target and perform a look-up (e.g., interrogate or query the controller 430 or the memory 435) to determine a current position of the movable arm 405. In certain embodiments, multiple images at multiple positions of the robotic arm, multiple locations of the target, or both multiple positions of the robotic arm and multiple locations of the target are recorded. For example, calibrations may be performed by keeping the movable arm of the robot stationary and rotating, moving, and/or tilting a calibration plate, keeping the calibration plate stationary and re-positioning/orienting the movable arm of the robot, or rotating, moving, and/or tilting the calibration plate and re-positioning/orienting the movable arm of the robot. The position of the movable arm (and/or the position of the calibration plate/target) at an individual image-capture location may be associated with the image(s) captured at that image-capture location in a suitable data structure and stored in a memory, such as the memory 435, so that the image(s) and movable arm position (and/or the position of the calibration plate) at the individual image-capture location can later be accessed and processed.

At step 830, coordinates of a set of calibration features of the target are determined in the camera system's coordinate system (e.g., coordinate system 477 or 487 in FIG. 4B). The set of calibration features that are utilized by the method 800 may be calibration features, such as the internal checkerboard corners 710 or dot-centroids 730 and 750 described with reference to FIGS. 7A and 7B. According to one embodiment, step 830 includes identifying the set of calibration features of the target in the set of images and calculating a three-dimensional location of the calibration features in the set. The three-dimensional location of the calibration features may be computed from the two-dimensional locations of the calibration features in the images captured by first and second cameras in a stereo camera pair as described with reference to FIG. 4B. According to another embodiment, coordinates of the set of calibration features are determined at step 830 by executing a look-up function. For example, after capturing an image, the camera system or a processor associated with the camera system may automatically calculate and store the coordinates of the calibration features in a memory, such as the memory 435. Thus, the processor 425 may perform a look-up (e.g., interrogate or query the camera system 415 or the memory 435) to determine the coordinates of the calibration features. Any number of calibration features may be included with the target, but in the provided example the method 800 is preferably implemented using 2 to 48 calibration features.

After the coordinates of the calibration features are determined at step 830, a transformation or relationship between the robot's coordinate system (e.g., the coordinate system 448 in FIGS. 4A and 4B) and the camera's coordinate system (e.g., coordinate system 477 or 487 in FIG. 4B) is determined at step 840 based on the position of the movable arm (and/or position of the target) and the coordinates of the set of calibration features at the individual image-capture locations. For example, the transformation may be determined by comparing the position of the movable arm and coordinates of the set of calibration features at each image-capture location to the position of the movable arm and coordinates of the set of calibration features at each of the other image-capture locations.

According to one embodiment, a position of the target is fixed and step 840 comprises iteratively selecting a value for the transformation between the robot's coordinate system and the camera system's coordinate system and comparing (A) a product of the selected value for the transformation, a position of the movable arm, and coordinates of a calibration feature at one image-capture location and (B) a product of the selected value for the transformation, a position of the movable arm, and coordinates of the corresponding calibration feature at another image-capture location, to determine a value for the transformation that minimizes a difference between (A) and (B).

The transformation between the robot's coordinate system and the camera's coordinate system may take the form of a transformation matrix, which can be denoted T, that transforms coordinates from the robot's coordinate system to the camera's coordinate system, and vice versa, according to Equation 3.

$$T := \min(\Sigma_{i=2}^{m} \Sigma_{j=1}^{(i-1)} \Sigma_{k=1}^{n} \|R_i T v_{ik} - R_j T v_{jk}\|)$$ Equation 3

One technique for finding T is to minimize the quantity $\Sigma_{i=2}^{m} \Sigma_{j=1}^{(i-1)} \Sigma_{k=1}^{n} \|R_i T v_{ik} - R_j T v_{jk}\|$, wherein i and j correspond to different instances of individual image-capture locations, i has a value ranging from 2 to m, j has a value ranging from 1 to (i−1), k corresponds to an individual calibration feature in the set of calibration features and has a value ranging from 1 to n, $R_i$ is the position of the movable arm at an individual image-capture location i, $v_{ik}$ are the coordinates, determined in the camera system's coordinate system, of the $k^{th}$ calibration feature at the $i^{th}$ image-capture location, $R_j$ is the position of the movable arm at an individual image-capture location j, and $v_{jk}$ are the coordinates, determined in the camera system's coordinate system, of the $k^{th}$ calibration feature at the $j^{th}$ image-capture location. As previously discussed, the method 800 may be implemented using any number m of image-capture locations and any number n of calibration features. According to one embodiment, the method 800 is implemented using three to six image-capture locations and 2 to 48 calibration features.

Because the target is fixed (e.g., the target does not move appreciably from one image-capture location to another image-capture location), when a calibration feature location is compared from one image-capture location to a different image-capture location and the arm has moved, the quantity $R_i T v_{ik} - R_j T v_{jk}$ should be zero or as close to zero as possible. In other words, T is selected to minimize the quantities $R_i T v_{ik} - R_j T v_{jk}$.

Equation 3 may also be expressed as $T := \min(\Sigma_{i=1}^{m} \Sigma_{j=1}^{m} \Sigma_{k=1}^{n} \|R_i T v_{ik} - R_j T v_{jk}\|)$, where j≠i. In certain embodiments j can be equal to 1, in which case the same image is effectively being compared to itself and the quantity $R_i T v_{ik} - R_j T v_{jk}$ should be zero. Comparing the image to itself will not help drive the optimization algorithm described below, so it may be desirable to skip calculations in which j=i to help conserve computational resources. Moreover, the function $\|R_i T v_{ik} - R_j T v_{jk}\|$ may comprise any distance function or measure.

According to one embodiment, the position of the movable arm comprises a robot-position transformation matrix R of the form expressed in Equation 1, above, where the upper-left three-by-three rotation sub-matrix (e.g., sub-matrix $r_{00}$ through $r_{22}$) represents an orthonormal rotation relating an orientation of the movable arm at an individual image-capture location to a reference orientation, such as the world origin frame 447 (FIG. 4A), and the sub-matrix x, y, z represents a three-dimensional offset between the position of the movable arm and the reference position. The coordinates of an individual calibration feature may comprise an array v of the form illustrated in Equation 2, above.

The transformation matrix T may comprise, for example, a 4×4 matrix, such as a matrix of the form illustrated in Equation 4, where the upper-left three-by-three rotation sub-matrix (e.g., sub-matrix $r_{00}$ through $r_{22}$) represents a rotational relationship between the robot's coordinate system and the camera system's coordinate system and is derived from three rotational offsets α, β, and γ as described above with reference to Equation 1, above, and the sub-matrix x, y, z represents translation offsets x, y, and z between the robot's coordinate system and the camera system's coordinate system. In other words, the transformation matrix T specifies the rotational and translation relationship between the robot's coordinate system and the camera system's coordinate system (e.g., how a motion in the camera system's field of view relates to a motion in the robot's coordinate system).

$$T = \begin{bmatrix} r_{00} & r_{01} & r_{02} & x \\ r_{10} & r_{11} & r_{12} & y \\ r_{20} & r_{21} & r_{22} & z \\ 0 & 0 & 0 & 1 \end{bmatrix}$$ Equation 4

The transformation matrix T illustrated in Equation 4 includes six independent values, three of which are translation offsets x, y, and z and the other three of which are rotational offsets α, β, and γ. Values for rotational offsets α, β, and γ and translation offsets x, y, and z of transformation matrix T are preferably determined using a suitable minimization procedure or optimization algorithm, such as a steepest descent optimization algorithm, a simulated annealing algorithm, or a best fit algorithm. The optimization algorithm helps determine a suitable value for each of the six independent values from a set of available alternatives. Steps 810-830 of method 800 generate the data to drive the optimization algorithm to calculate the transformation matrix T. Rotating the movable arm around the target in addition to translating the movable arm relative to the target at step 810 helps provide a rich set of data that allows Equation 3 to be solved and a relationship between a camera system's coordinate system and robot's coordinate system to be defined.

The method 800 may be used to determine transformations between multiple camera system coordinate systems and the robot's coordinate system. For example, the method 800 may determine a first transformation $T_1$ that specifies the rotational and translation relationship between the robot's coordinate system 448 (FIG. 4B) and the camera coordinate system 477 of the camera pair 470 and a second transformation $T_2$ that specifies the rotational and translation relationship between the robot's coordinate system 448 and the camera coordinate system 487 of the camera pair 480. The transformation matrix $T_1$ is conceptually illustrated in FIG. 10B by the arrow extending from the robot's coordinate system 448 to the camera coordinate system 477. Similarly, the transformation matrix $T_2$ is conceptually illustrated in FIG. 10B by the arrow extending from the robot's coordinate system 448 to the camera coordinate system 487. One or more of the steps 810-840 may be repeated to determine the first and second transformation $T_1$ and $T_2$. For example, steps 810, 820, and 830 may be performed at the same time to generate the data to drive the optimization algorithm and step 840 may be repeated twice to calculate the transformation matrices $T_1$ and $T_2$. As yet another alternative, step 840 can loop back to steps 810 and 820 to collect additional data to further refine the transformation by using an iterative algorithm, one iteration of which is completed during each pass through the step 840, such that each iteration successively approximates more closely the solution. Examples of iterative algorithms that can be used in this way include recursive least squares (RLS), least mean square (LMS), and gradient descent.

After the transformation is determined, in whatever form, at step 840, the method 800 may optionally store that transformation in a memory, such as the memory 435, for later use. Alternatively, or in addition, the method 800 may transmit the transformation to a desired location or display it on a suitable display device, such as display 450. Moreover, if the system includes multiple camera systems, the method 800 may additionally determine a mapping between the camera coordinate systems, which is described in greater detail with respect to FIG. 10A. According to one embodiment, the method 800 is performed independently of having a tool or tool tip contact a calibration point (e.g., without moving the robotic arm from a home position and orientation to a position in which the tool or tool tip contacts the calibration point).

One or more of steps 810-840 may be performed automatically without user intervention. Moreover, the method 800 and its steps may be implemented using various structures. For example, the positioning step 810 may be performed using one or more of the processor 425 (FIG. 4A), the controller 430, and the motors and encoders located in respective arm joints of the movable arm 405. Capturing the set of images at step 820 can be performed using a camera system, such as the camera system 415, and recording the position of the movable arm at step 820 may be performed using one or more of the processor 425, the controller 430, and the memory 435. The coordinate determination step 830 and the transformation determination step 840 may be performed using one or more processors, such as the processor 425 or the image processor 426. The steps 810-840 may be performed in any order or in parallel (e.g., at the same time). Moreover, one or more of the steps 810-840 may be omitted and/or replaced with other steps. For example, steps 810 and 820 may be performed independently and separately such that the method 800 may start with "determining coordinates . . . " (e.g., step 830) from the already existing captured set of images and recorded locations. In some embodiments, the position of the calibration plate/target (and/or the position of the movable arm) at individual image-capture locations and the image(s) captured at the image-capture locations may be received, accepted, or accessed (e.g., accessed from a memory, such as the memory 435). After the position of the movable arm (and/or the position of the calibration plate/target) and the image(s) captured at the image-capture locations are received, accepted, or accessed, the method 800 may perform the coordinate determination step 830 and the transformation determination step 840.

Figure 9:
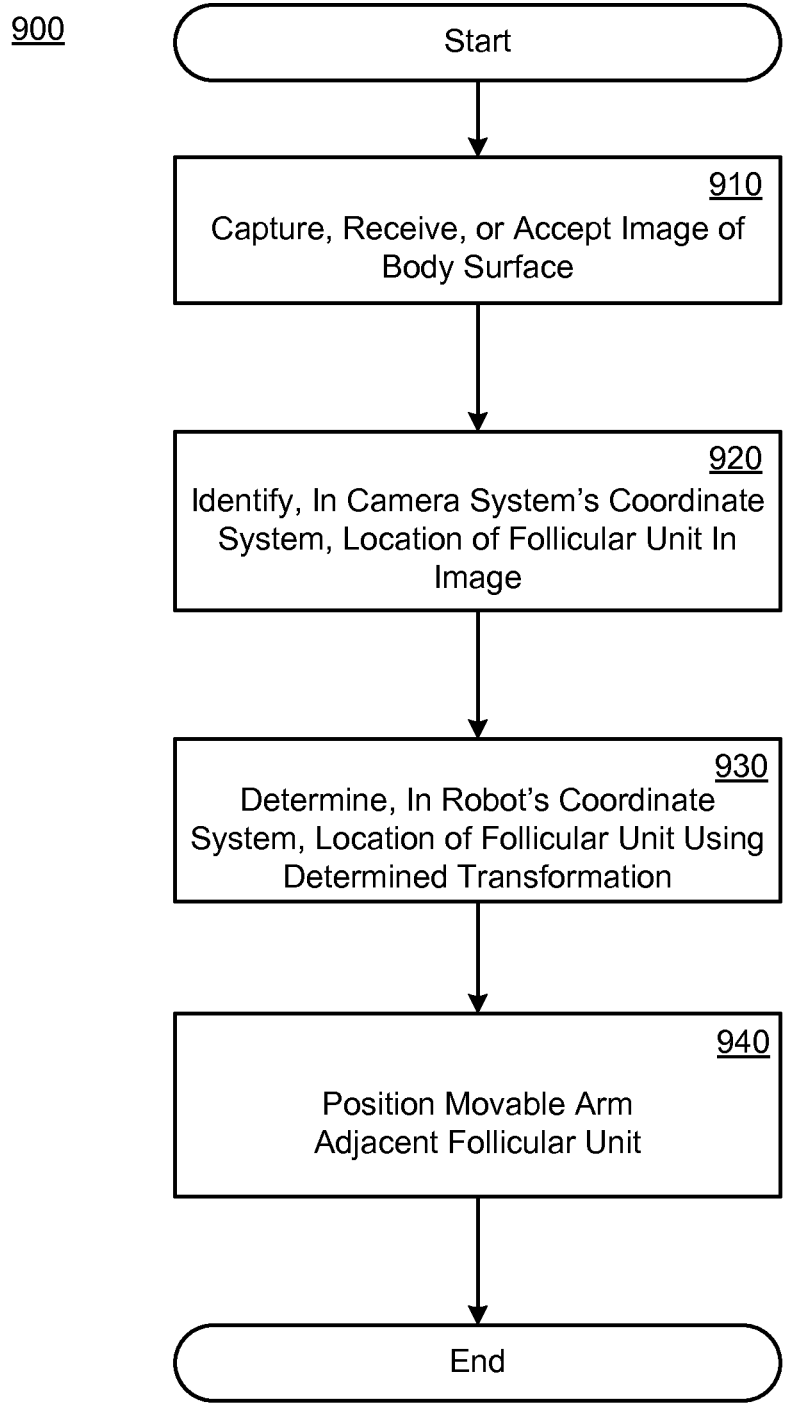
FIG. 9 is a flow diagram of an example of a method for using the transformation determined by the method illustrated in FIG. 8 to position an end-effector tool assembly during hair extraction/implantation procedures.

After one or more transformations (e.g., transformation matrices $T_1$ and $T_2$) are determined by the method 800 or another suitable method, the transformations can be utilized to readily convert coordinates between the robot's coordinate system and the camera system's coordinate system. One such conversion is illustrated in FIG. 9, which is a flow diagram of a method 900 for using the transformation determined by the method illustrated in FIG. 8 to position an end-effector tool assembly during hair extraction/implantation procedures. At an optional step 910, the method 900 may capture one or more images of a body surface using a camera system having a coordinate system. In certain embodiments, the method 900 may start, for example, with step 920 by identifying in images of a body surface (already captured by a camera system) coordinates of one or more features of interest in the camera system's coordinate system. Such captured images may be, for example, previously or contemporaneously received, or accepted or accessed from a memory. The feature of interest may be, for example, a hair follicle or an implantation site for a hair graft. According to one embodiment, step 920 includes identifying the feature of interest in the image and calculating a three-dimensional location of the feature of interest. The three-dimensional location of the feature of interest may be computed from the two-dimensional locations of the feature of interest in the images captured by first and second cameras in a stereo camera pair as described with reference to FIG. 4B. According to another embodiment, coordinates of the feature of interest are determined at step 920 by executing a look-up function (e.g., interrogating or querying the camera system 415 or the memory 435 in FIG. 4A) to determine the coordinates of the feature of interest.

The method 900 may also retrieve the transformation (e.g., one of the transformation matrices $T_1$ and $T_2$) determined by the method 800 (e.g., by performing a look-up in the memory 435) and transform the coordinates of the feature of interest from the camera system's coordinate system to the robot's coordinate system at step 930. Transforming the coordinates of the feature of interest from the camera system's coordinate system to the robot's coordinate system may be determined from Equation 5, where T is the transformation matrix (e.g., determined by the method 800), $v_C$ are the coordinates, determined in the camera system's coordinate system, of the feature of interest, and $v_R$ are the coordinates of the feature of interest in the robot's coordinate system relative to the robot flange 446.

$$v_R = T^* v_C \qquad \text{Equation 5}$$

At step 940, the movable arm is positioned adjacent the feature of interest. For example, based on the coordinates of the feature of interest in the robot's coordinate system, the processor 425 can generate instructions that cause the controller 430 to move the arm 405 to a desired position and orientation relative to the feature of interest. If the feature of interest is a hair follicle, the processor 425 can generate instructions that cause the controller 430 to rotate and position a harvesting tool mounted to the movable arm relative to the follicular unit so the harvesting tool can harvest such follicular unit. It should be noted that the steps of the method 900 may be performed in an order different than shown or simultaneously rather than sequentially.

Figure 10A:
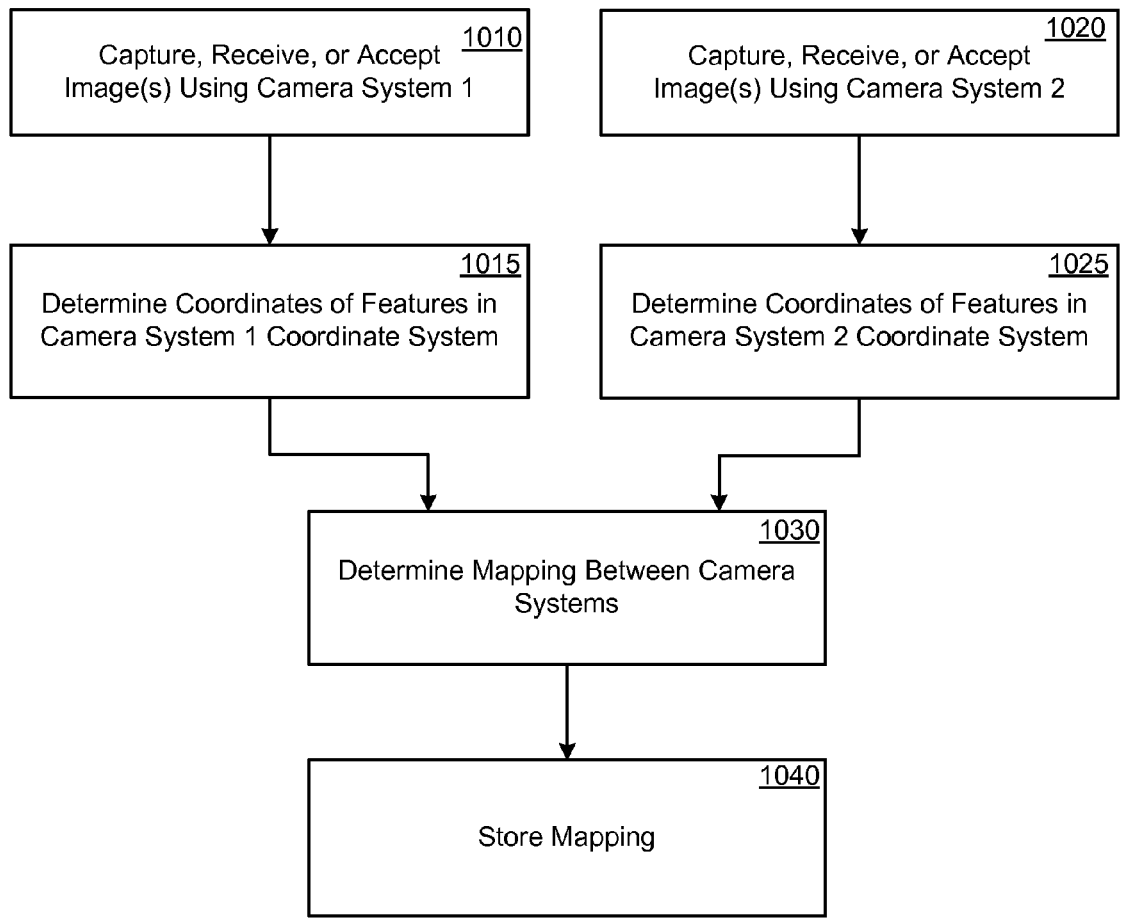
FIG. 10A is flowchart of a method for determining a coordinate transformation between camera systems, according to one embodiment.

FIG. 10A is flowchart of a method 1000 for determining a coordinate transformation or mapping between two camera systems, according to one embodiment. The resulting coordinate transformation can be used to transform coordinates in the coordinate system of a first camera system to the coordinate system of a second camera system, or vice versa, as explained below with reference to FIG. 11. The method 1000 is a process for determining that transformation. The first and second camera systems may be, for example, the camera systems 510 and 520 illustrated in FIG. 5 or 6. The first and second camera systems have fields of view that at least partially overlap so that they can generate corresponding images of corresponding features. The first and second camera systems may each be stereo pairs of cameras; they may differ in the sizes of their fields of view; and/or they may be mounted to a robotic arm, such as one used for hair harvesting and/or implantation.

At optional steps 1010 and 1020, the method 1000 may capture images from each of the camera systems. In certain embodiments, the images may be received, accessed, or accepted, for example, as mentioned in reference to FIGS. 8 and 9 above. At steps 1015 and 1025, the method 1000 determines local coordinates of corresponding features in the images. Using those different coordinates of corresponding features, the method 1000 determines a mapping between the camera system's coordinate systems (step 1030) and stores that mapping in a memory (1040). The steps 1015, 1025 and 1030 are performed by one or more processors, such as the processors illustrated in FIG. 5 or 6. The features that are utilized by the method 1000 may be calibration features, such as checkerboard corners or dot centroids, as explained elsewhere in this document, such as above with reference to FIGS. 7A-7C.

Each step of the method 1000 will now be described in more detail. At optional step 1010, the method 1000 may capture one or more images using the first camera system. In certain embodiments, the one or more images may be received, accessed, or accepted as described above so that the method 1000 may determine coordinates of features in the coordinate system of the first camera system (step 1015) from the images captured by the first camera system. At optional step 1020, the method 1000 may also capture one or more images using the second camera system. In certain embodiments, the one or more images may be received, accessed, or accepted so that the method 1000 may determine coordinates of features in the coordinate system of the second camera system (step 1025) from the images captured by the second camera system. The steps 1010, 1015, 1020 and 1025 may be performed in parallel, as shown. In fact, the steps 1010 and 1020 may be performed simultaneously or nearly simultaneously so as to result in corresponding images. Alternatively, the steps 1010, 1015, 1020 and 1025 may be performed sequentially in any feasible order that results in corresponding images having corresponding features. The goal of those steps is to generate sets of coordinates of corresponding features found in corresponding pairs of images from the first and second camera systems. In other words, those steps result in a first set of feature coordinates in the first camera system's coordinate system and a corresponding second set of coordinates in the second camera system's coordinate system.

It is possible, as well as insightful, to utilize a mathematical notation to refer to the images, features in those images, and coordinates of those features in each coordinate system. The symbols $v_1$ and $v_2$ can be used to represent coordinates in the first and second camera system's coordinate systems, respectively. Each of $v_1$ and $v_2$ may be, for example, a vector of coordinates in a form like that specified in Equation 2, which is a useful form for representing three-dimensional coordinates, as would be produced by a camera system that is a stereo pair of cameras. Other forms of the coordinates for $v_1$ and $v_2$ can also be used, including forms having fewer dimensions.

Additional indices can be used to specify images and features. For example, a next index, j, can be used to specify the image, wherein the number of corresponding images from each of the first and second camera systems is m, the $j^{th}$ image from the first camera system and the $j^{th}$ image from the second camera system correspond to each other for j=1 . . . m. Furthermore, a next index, k, can be used to specify features in an image, wherein the number of features whose coordinates are determined in each image is n. According to this notation, the first set of feature coordinates determined in the first camera system's coordinate system is $\{v_{1jk}\}$, and the second set of feature coordinates determined in the second camera system's coordinate system is $\{v_{2jk}\}$ where j is an index to the $j^{th}$ image among the images 1 . . . m, and k is an index to a $k^{th}$ feature among the features 1 . . . n in the $j^{th}$ image.

The method 1000 is operable for any values of m≤1 and n≤2, and mn≤6. In other words, the method 1000 works with as few as a single image from each camera system and a minimum of two different features so long as the product of images times features per image is at least six. Additional features and/or images generates additional data that makes the method 1000 more accurate. In one embodiment, m=48 and n=6, resulting in 288 pairs of feature coordinates.

Step 1030 of the method 1000 determines, based on the first and second set of feature coordinates (e.g., $\{v_{1jk}\}$ and $\{v_{2jk}\}$), a mapping or transformation from one camera system's coordinate system to another. The mapping or transformation may take the form of a transformation matrix, which can be denoted Q, that transforms coordinates from the second coordinate system (e.g., the coordinate system 487 illustrated in FIGS. 4B and 10B) to the first coordinate system (e.g., the coordinate system 477 illustrated in FIGS. 4B and 10B) as follows:

$$v_1 = Q^* v_2. \quad \text{Equation 6}$$

One technique for finding Q is to minimize the quantity $\Sigma_{j=1}^{m} \Sigma_{k=1}^{n} d(Qv_{2kj}, v_{1kj})$ wherein d is a distance function, such as, for example, the $L^2$ norm distance function $d = \|Qv_{2jk} - v_{1jk}\|$ or $d = \|Qv_{2jk} - v_{1jk}\|^2$. Any optimization technique could alternatively be used to find Q. As yet another alternative, step 1030 can loop back to steps 1010 and 1020 to collect additional data to further refine the mapping by using an iterative algorithm, one iteration of which is completed during each pass through the step 1030, such that each iteration successively approximates more closely the solution. Examples of iterative algorithms that can be used in this way include recursive least squares (RLS), least mean square (LMS), and gradient descent.

Once the mapping or transformation is determined, in whatever form, by step 1030, the method 1000 can optionally store that mapping in a memory (step 1040) for later use. Alternatively, the method 1000 may, for example, instead transmit the mapping to a desired location, or display it on a suitable display device.

The method 1000 and its steps can be implemented using various structures. For example, the image capturing steps 1010 and 1020 can be performed using camera systems, such as the camera systems 510 and 520 shown in FIG. 5 or 6; the coordinate determination steps 1015 and 1025 can be performed using one or more processors, such as the processor 550 in FIG. 5 or the processors 610 and 620 in FIG. 6; and the mapping determination step 1030 can be performed using a processor, such as the processor 550 in FIG. 5 or the processor 650 in FIG. 6.

Figure 10B:
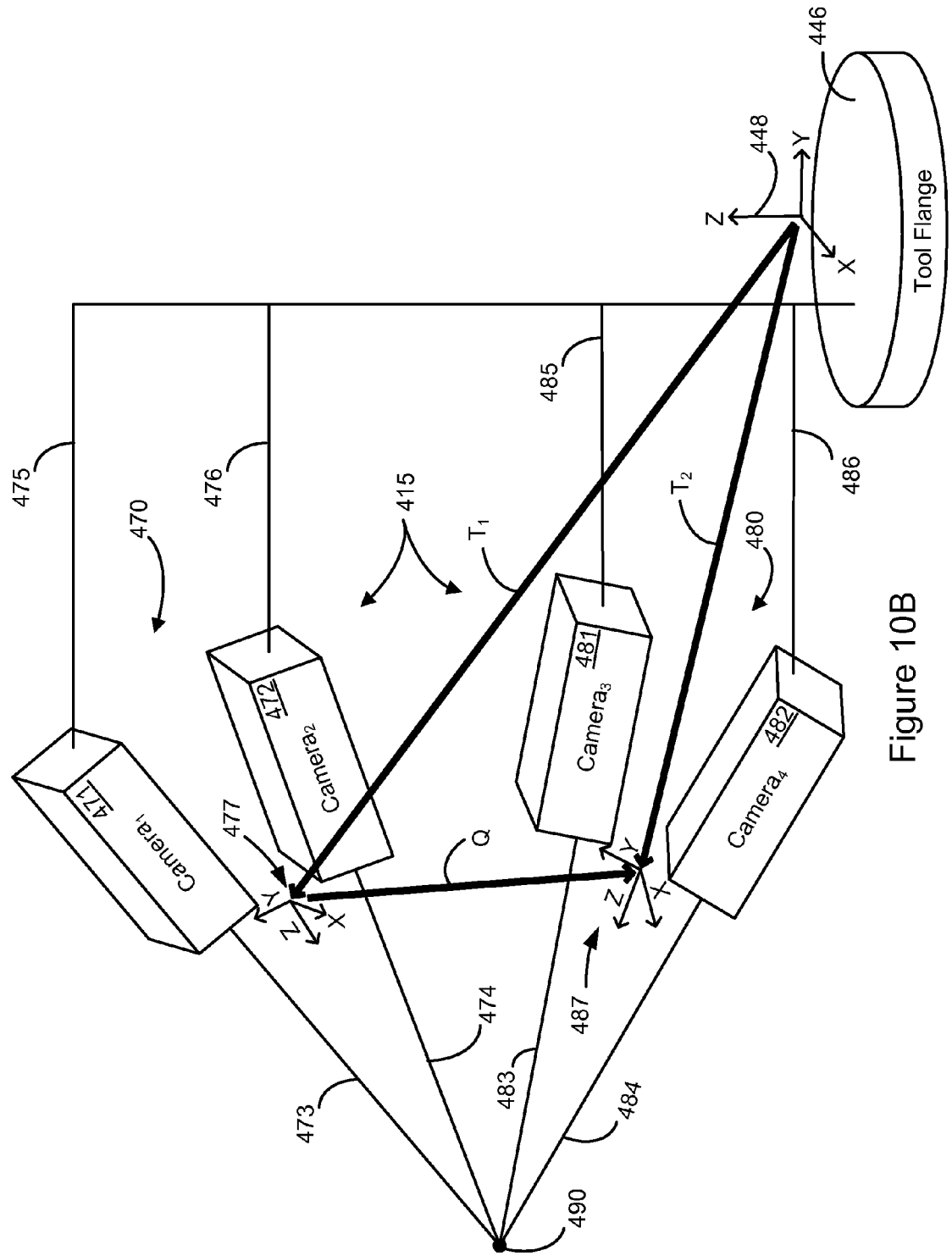
FIG. 10B is a block diagram illustrating a coordinate transformation between first and second camera systems, a coordinate transformation between the first camera system and a robot's coordinate system, and a coordinate transformation between the second camera system and the robot's coordinate system.

The coordinate transformation matrix Q mapping coordinates from the second coordinate system (e.g., the coordinate system 487) to the first coordinate system (e.g., the coordinate system 477) is conceptually illustrated in FIG. 10B by the arrow extending from the coordinate system 477 to the coordinate system 487. FIG. 10B is substantially similar to FIG. 4B, except that FIG. 10B conceptually illustrates coordinate transformation matrices Q, $T_1$, and $T_2$. In FIG. 10B, the stereo camera pair 470 is an example of the first camera system described with reference to FIG. 10A. Similarly, the stereo camera pair 480 illustrated in FIG. 10B is an example of the second camera system described with reference to FIG. 10A. The arrow extending from the robot's coordinate system 448 to the camera coordinate system 477 in FIG. 10B conceptually illustrates the transformation matrix $T_1$, which specifies the rotational and translation relationship between the camera coordinate system 477 of the camera pair 470 and the robot's coordinate system 448. Similarly, the arrow extending from the robot's coordinate system 448 to the camera coordinate system 487 in FIG. 10B conceptually illustrates the transformation matrix $T_2$, which specifies the rotational and translation relationship between the camera coordinate system 487 of the camera pair 480 and the robot's coordinate system 448.

Because the camera coordinate systems 477 and 487 are not coincident, a feature viewed and reported by the stereo camera pairs 470 and 480 will have coordinates $v_1$ and $v_2$ that differ from each other. It may be desirable to have the coordinates returned by both camera pairs 470 and 480 to be identical within operational tolerances (e.g., to have the coordinates of the point 490 returned by the camera pair 470 to be the same or approximately the same as the coordinates of the point 490 returned by the camera pair 480). This can be achieved by replacing the equation for the location of a vision feature $R*T_2*v_2$ with a modified equation $R*(T_2*Q^{-1})*(Q*v_2)$, where Q is the transformation that maps vision coordinates returned by the stereo camera pair 480 into the same coordinates returned by the stereo camera pair 470. For example, an automation algorithm that plans which hair follicles to harvest may keep track of all of the hair follicles in a grid using a global coordinate system (e.g., a global coordinate system relative to a position and orientation of a skin tensioner device). Each hair follicle may be found, tracked, and added to the global coordinate system using a higher magnification camera coordinate system. After the coordinate transformation matrix Q is computed (e.g., using the method 1000), the robot-to-camera transformation between the camera coordinate system 487 of the camera pair 480 and the robot's coordinate system 448 may be computed as $T'_2=T_2*Q^{-1}$ and the coordinates returned by the second camera pair 480 may be reported as $v'_2=Q*v_2$. By using the transformation matrix Q to adjust the vision feature coordinates reported by the camera pair 480, the coordinates of a feature of interest reported by the camera pairs 470 and 480 should be the same or approximately the same. For example, the location of a target may be found using camera pair 2 (e.g., a low-magnification camera pair) and converted into the coordinate system of camera pair 1 (e.g., a high-magnification camera pair) using $v_1=Q*v_2$, which may, for example, allow camera pair 1 to locate a hair follicle in order to orient the robotic arm relative to the hair follicle for harvest. By way of another example, if camera pair 1 (e.g., a high-magnification camera pair) reports a harvested site location, camera pair 2 (e.g., a low-magnification camera pair) may find that harvested site using $v_2=Q^{-1}*v_1$.

If two of the three coordinate transformation matrices Q, $T_1$, and $T_2$ are known (e.g., computed using the method 800, 1000, or both), it may be possible to determine the third transformation from the two known transformations. For example, if the transformation matrix Q is computed using the method 1000 and the transformation matrix $T_2$ is computed using the method 800, the transformation matrix $T_1$ (or an approximation of $T_1$) can be computed as $T_1=T_2*Q^{-1}$. Determining the third transformation from the two known transformations may help conserve computational resources. For example, deriving $T_1$ from $Q^{-1}$ and $T_2$ may help avoid having to use an optimization algorithm to compute the transformation matrix $T_1$.

Figure 11:
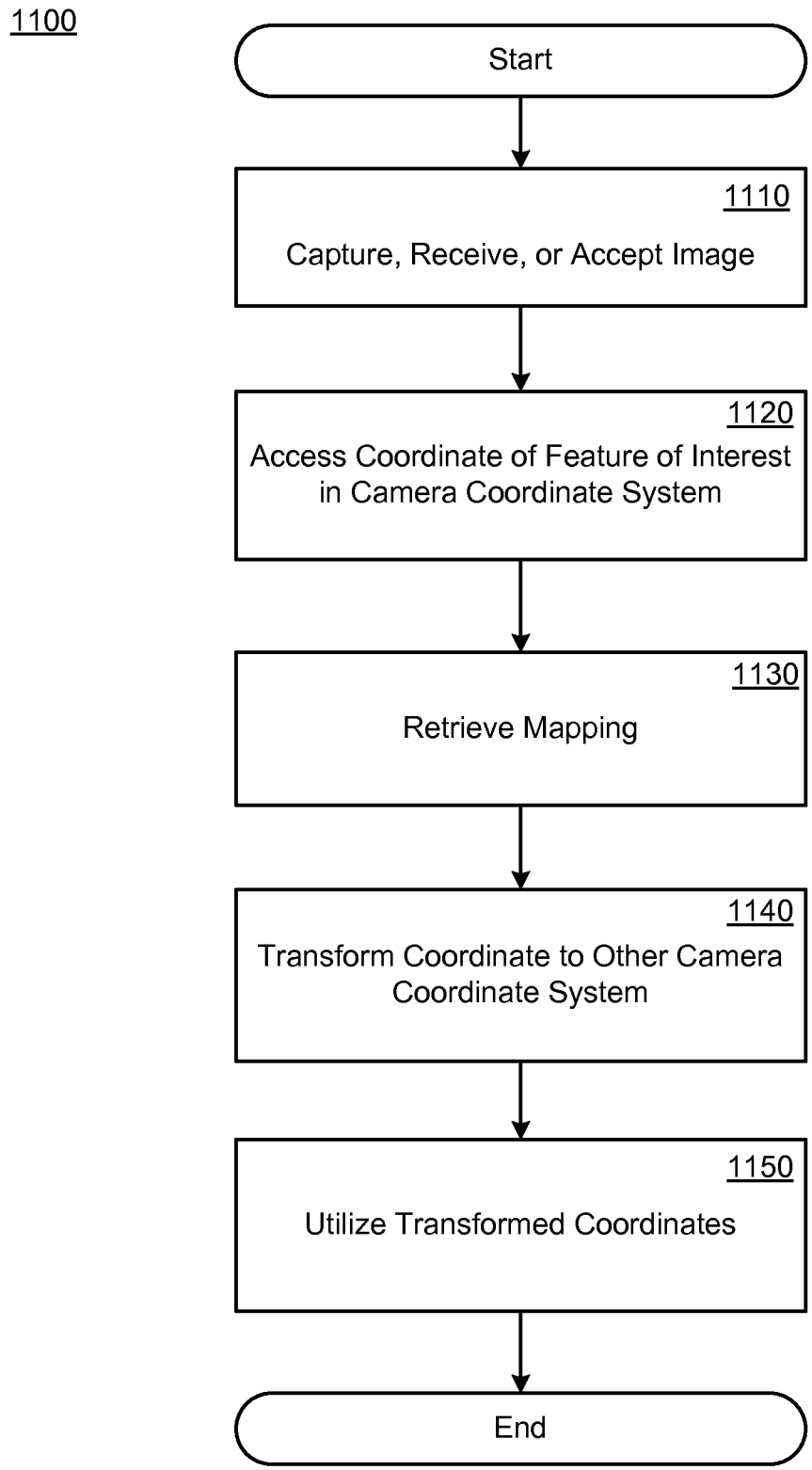
FIG. 11 is flowchart of a method for transforming coordinates between camera systems, according to one embodiment.

After a mapping (e.g., the transformation matrix Q) is determined by the method 1000 or another suitable method, then that mapping can be utilized to readily convert between the coordinate systems of the first and second camera systems. One such conversion is illustrated in FIG. 11, which is a flowchart of a method 1100 for transforming coordinates between two different camera systems, according to one embodiment. At an optional step 1110, the method 1100 may capture one or more images using a camera system having one coordinate system. In certain embodiments, the one or more images may be received, accessed, or accepted in a manner similar to one described in reference to FIGS. 8, 9 and 10 so that the method 1100 accesses coordinates of a feature of interest from the image in that coordinate system (step 1120) (e.g., $v_2$). The feature of interest may be a hair follicle or an implantation site for a hair graft. In the case of a two-dimensional camera system, determining coordinates may be as simple as determining X and Y offsets from a reference based on pixel counts. In the case of a stereo pair of cameras, techniques for determining a three-dimensional coordinate are well known in the art. The method 1100 also retrieves the mapping (e.g., Q) (step 1130), such as determined by the method 1000, and transforms the coordinates from the local camera system's coordinate system to another camera system's coordinate system (step 1140) (e.g., $v_1=Q*v_2$). The method 1100 proceeds to utilize the transformed coordinates (e.g., $v_2$) as desired. It should be noted that the steps of the method 1100 may be performed in an order different than shown or simultaneously rather than sequentially. For example, the mapping retrieval step 1130 may be performed at any time earlier than is shown in FIG. 11.

Figure 12:
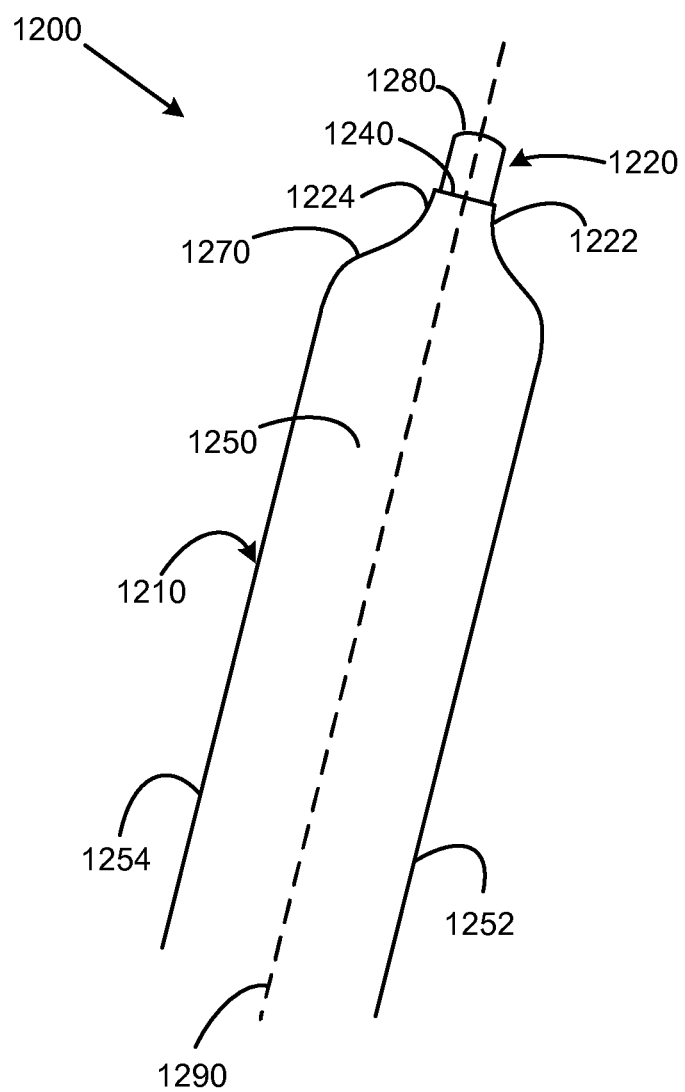
FIG. 12 is an example of an end-effector tool assembly illustrating features that may be located using, for example, an image-guided robotics system having multiple camera systems and using machine vision operations.
Figure 13:
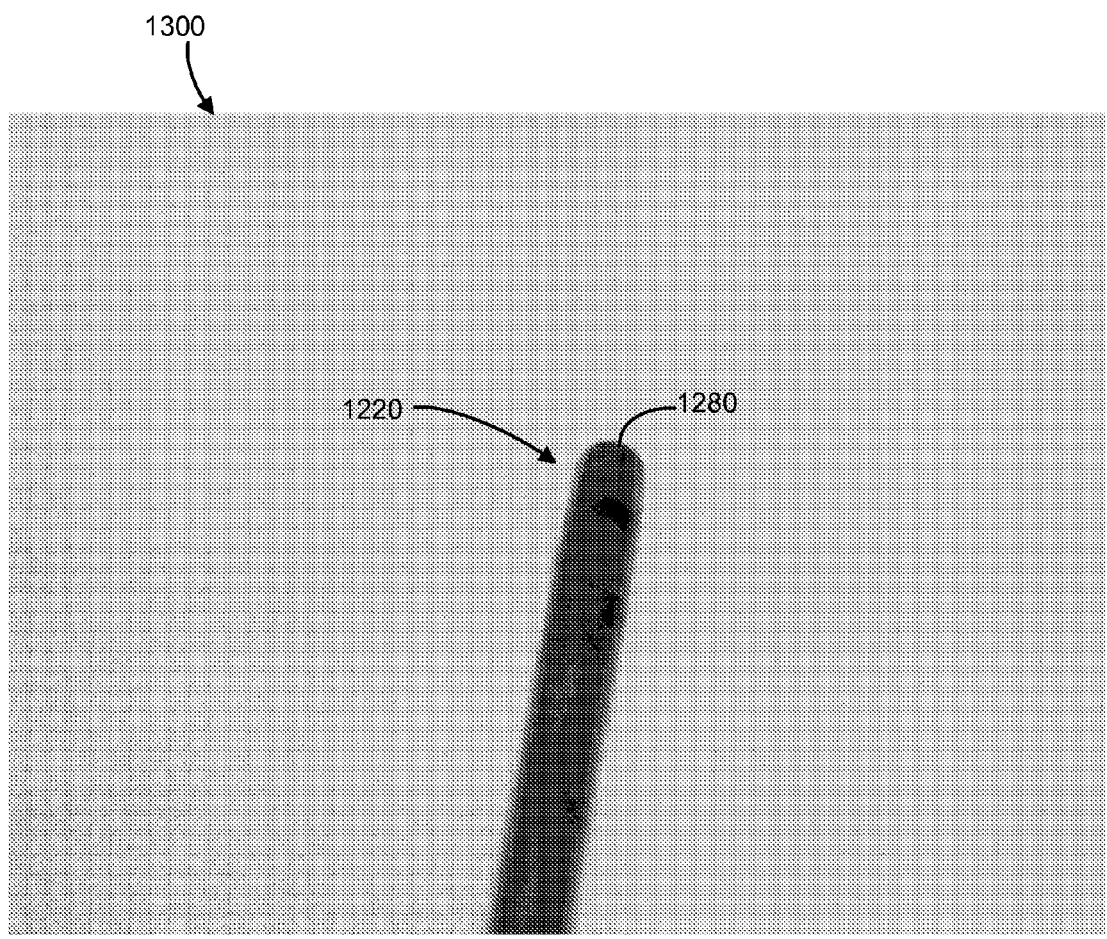
FIG. 13 is an image of a needle tip of an end-effector, extended for location using machine vision operations.

FIG. 12 is a diagram of an example needle assembly 1200 that may be attached to a robotic arm (see, e.g., the robotic arms 110 or 405 described with reference to FIGS. 1 and 4A, respectively) as part of an end-effector assembly (see, e.g., the tool 410 described with reference to FIG. 4A) for use, for example, in hair harvesting procedures. As shown in FIG. 12 and described below, various features on the needle assembly 1200 may be located with machine vision operations as part of a tool-location calibration routine. In certain configurations, the needle assembly 1200 may include an outer needle ("punch") 1210, and a co-axial inner needle 1220. The needle 1220 is typically cylindrical with a relatively sharp distal tip 1280. This needle is sized to fit within a lumen of the punch 1210. The punch 1210 may include a main cylindrical portion 1250 with sides 1252 and 1254 that transition through a curved shoulder 1270 to a narrower cylindrical distal portion with side walls 1222 and 1224. The punch 1210 also includes a distal tip 1240. The needle assembly 1200 may be extended or retracted along a translational axis of motion, represented by a centerline 1290. Additionally, the needle 1220 may be extended and retracted inside the punch 1210 along the centerline 1290. For example, FIG. 13 shows an example image 1300 from a camera system (see, e.g., the camera system 415 described with reference to FIG. 4A) depicting the needle 1220 extended to a position corresponding, for example, to a skin plane, while the punch 1210 is not within the camera's field of view.

Figure 14:
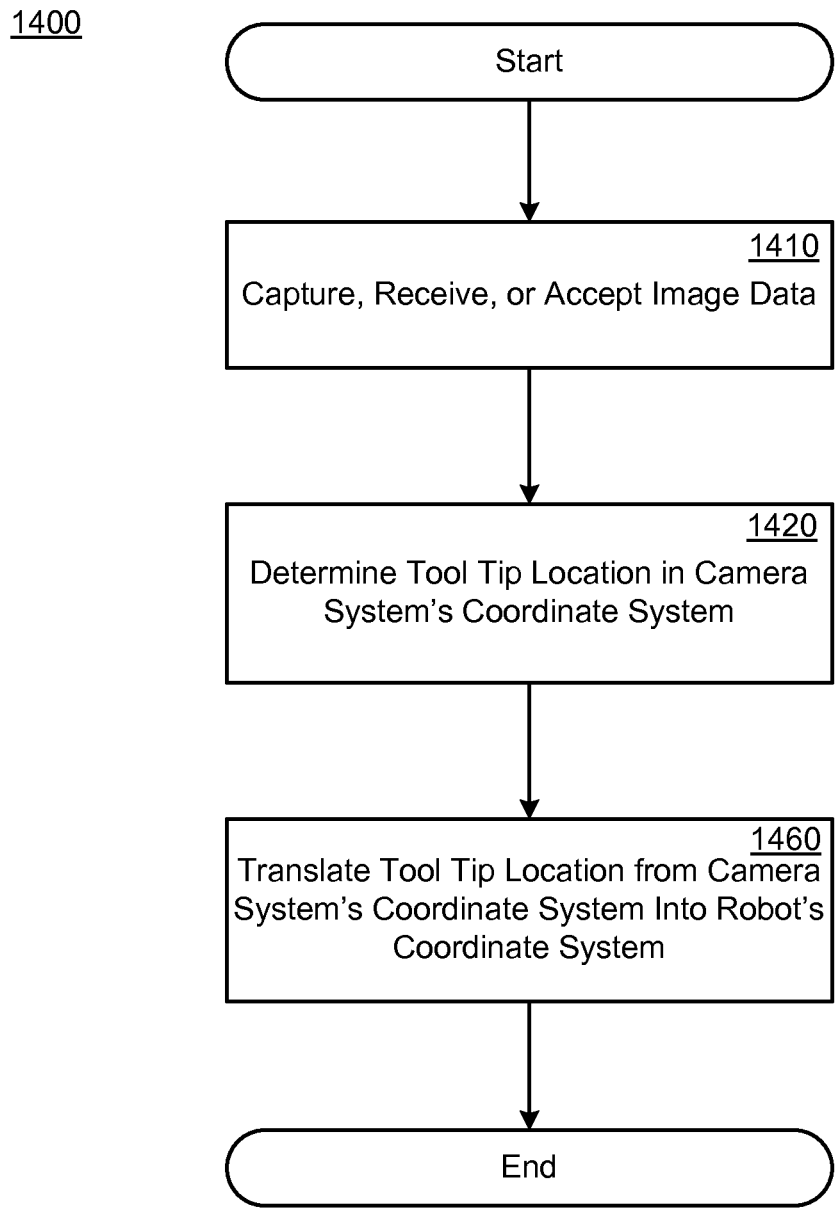
FIG. 14 is a flow diagram of a method for locating an end-effector tool in a robot coordinate system, according to one embodiment.

FIG. 14 shows a flow diagram depicting an example of a tool-location calibration method 1400. Similar to the description of FIGS. 8-11, step 1410 is optional. The method 1400 may include a step of capturing image data with a camera system, such as the camera system 415, or the method may comprise determining tool tip location, for example, from an existing image data. In certain embodiments, the image data may be received, accessed, or accepted as previously described. The image data may represent an end-effector tool and the data may include a pair of images from the stereo camera pair 470 or 480, discussed previously. According to one embodiment, the image data may represent at least some portion of the needle assembly 1200, or a single needle or punch if a single punch configuration of the tool assembly is used.

The method 1400 continues to a step 1420 that includes determining a location of the tool tip in the camera system's coordinate system. In the example stereo camera pair 470, the location of the tool tip 1280 (e.g., the tip 1280 of the needle 1220, or the tip 1240 of the punch 1210) is determined within the coordinate system 477. As noted above with respect to FIG. 12, the camera systems may locate other visible features and the tool tip, such as the tip 1280, is just one example of a tool feature that may be located using machine vision method. The determined location may include three-dimensional coordinates obtained, according to a standard (previously described) process, from a pair of two-dimensional locations of a point (see, e.g., the point 490) located within stereo camera images.

Once the tool location has been determined in the camera system's coordinate system, the method 1400 continues to a step 1460 that includes translating the tool location from the camera system's coordinate system into a robot's coordinate system (e.g., the coordinate system 448 in FIGS. 4A and 4B). With an accurate tool-location calibration, the translated location may be used to determine an offset from the robot flange 446, used by the processor 425 to instruct the robot arm 405 to move the end-effector tool assembly 410 so that the tool, e.g., the needle assembly 1200, may perform a harvest operation. According to one embodiment, the translation can be calculated as follows:

$$t_{rob} = T^* t_{cam} \quad \text{Equation 7}$$

where $t_{cam}$ is the determined tool location, T is a transformation matrix for a camera (e.g., a transformation between the robot's coordinate system and the camera's coordinate system determined according to Equation 3), and $t_{rob}$ is a tool-location in terms of the robot tool flange 446.

The method 1400 and its steps may be implemented using various structures. For example, image capture step 1410 can be performed using a camera system, such as the camera system 415 and the location determining and translation steps 1420 and 1460 may be performed using one or more processors, such as the processor 425 or the image processor 426. The steps 1410, 1420, and 1460 may be performed in any order or in parallel (e.g., at the same time).

Figure 15:
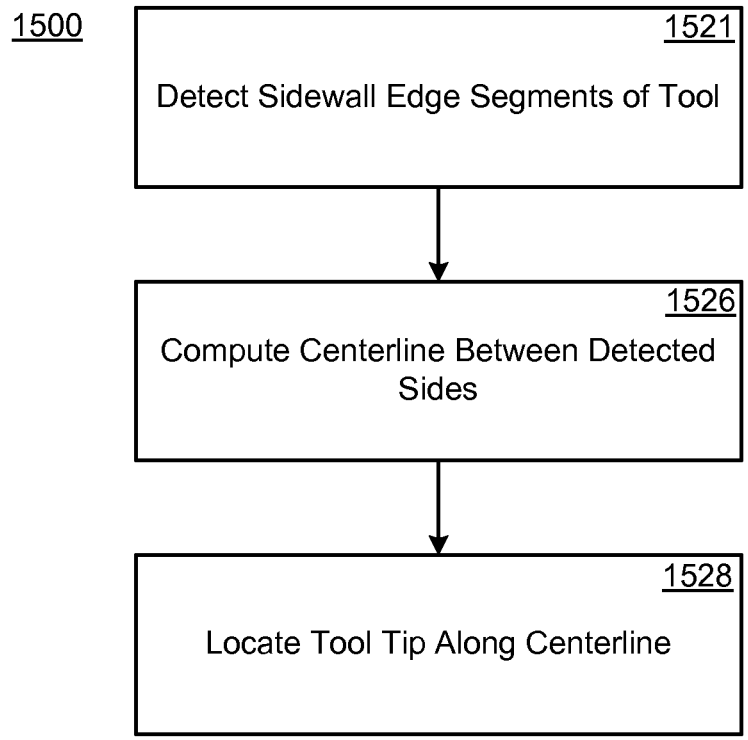
FIG. 15 is a flow diagram of a method for determining a location of an end-effector tool in a camera's coordinate system by detecting and locating the features of the tool, for example, the tool shown in FIG. 12, according to one embodiment.

FIG. 15 shows a flow diagram depicting an example method 1500 for carrying out the step 1420 of the method 1400 (FIG. 14). A step 1521 includes detecting from the image data first and second peripheral sidewall edge segments corresponding to sides of the tool within a field of view of the camera system. In the example needle assembly 1200 (FIG. 12), for example, the sides 1252 and 1254 may be detected and represented by line segments, and/or the sides 1222 and 1224 may be detected and represented as line segments.

Next, a step 1526 includes computing a centerline based on an average between the detected first and second peripheral sidewall edge segments. In the example needle assembly 1200, the centerline 1290 may be computed as the average distances between the sides 1252 and 1254.

A step 1528 includes locating in the camera system's coordinate system, a spatial position of a distal end of the tool along the centerline. In the example needle assembly 1200, the needle 1220 and the punch 1210 are generally straight. Thus, when the centerline 1290 is accurately computed, the tip 1280 of the needle 1220 or the tip 1240 of the punch 1210 will generally be located along the centerline 1290, e.g., between the sides 1222, 1224 or 1252, 1254. For example, a tool tip, such as the tip 1240, may be located by a change in image data along the centerline 1290, e.g., a data transition point as discussed below with respect to FIG. 16. In an alternative method (not shown), a center of mass or centroid may be determined for the data representing the needle assembly 1200, and a point located farthest from the center of mass may correspond to the tool tip.

The method 1500 and its steps may be implemented using various structures. For example, the steps 1521, 1526, and 1528 may be performed using one or more processors, such as the processor 425 or the image processor 426. The steps 1521, 1526, and 1528 may be performed in any order or in parallel (e.g., at the same time).

Figure 16:
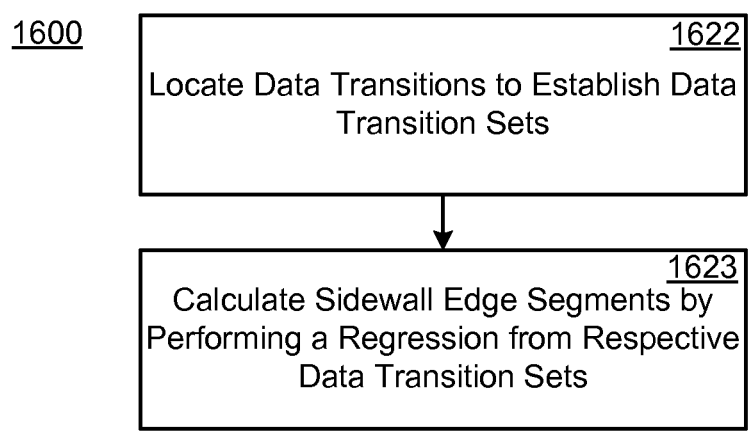
FIG. 16 is a flow diagram of a method for detecting sidewall edge segments of an end-effector tool in a camera's coordinate system by locating data transitions and calculating a regression, according to one embodiment.

FIG. 16 shows a flow diagram depicting an example method 1600 for carrying out the step 1521 of the method 1500 (FIG. 15). A step 1622 includes locating first and second data transitions in individual rows of the image data to establish a first and second set of data transitions. For example, FIGS. 17A and 17B show an image 1700 of the punch 1210 in grayscale 1710 and binarized 1720 formats, respectively.

Figure 17A:
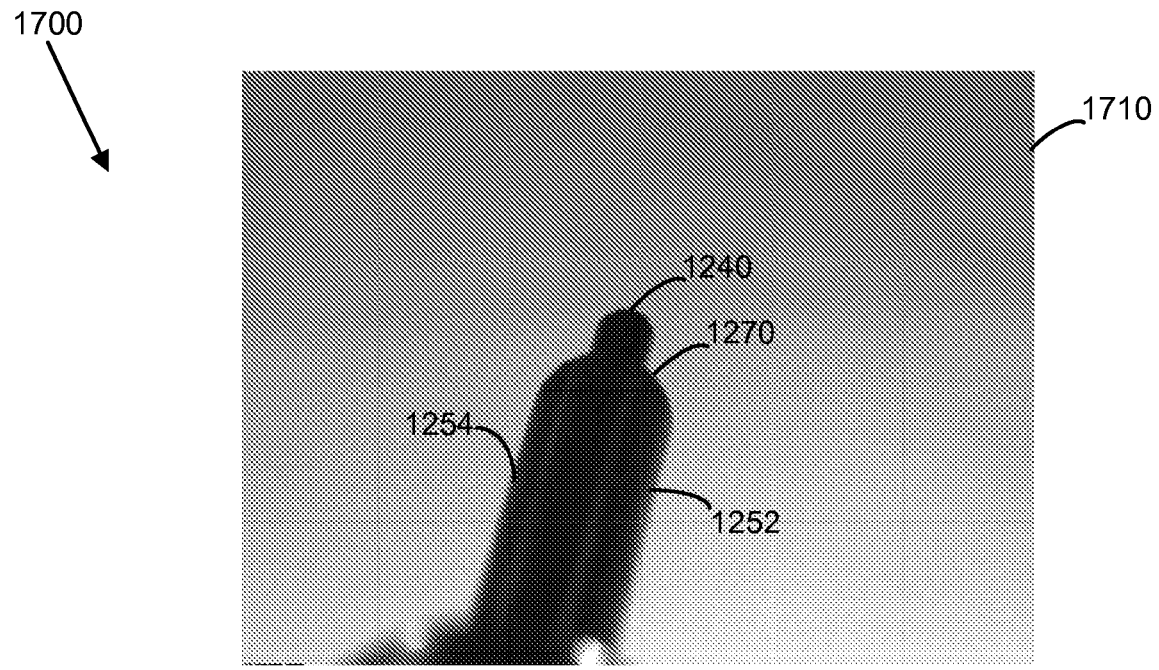
FIGS. 17A and 17B are respective unprocessed and binarized images of an extended end-effector tool.

According to one embodiment shown in FIG. 17A, the data transitions may be identified as transitions from light colors to dark colors along pixel-rows of a digital image 1700. The digital image 1700 may be represented as a matrix of pixel intensities, in which case the data transitions may be identified by variances of data values along rows of the matrix. The method 1600 and its steps may be implemented using various structures. For example, the steps 1622 and 1623 may be performed using one or more processors, such as the processor 425 or the image processor 426. The steps 1622 and 1623 may be performed in any order or in parallel (e.g., at the same time).

To locate data transitions, a row of pixels in the image 1700 may be traversed to locate a first and second detected transition corresponding to opposing sides of a tool. The first and second transitions may be recorded in respective first and second sets of transitions. Depending on the resolution of the image data, every row for the entire image may be traversed; however, skipping some rows may increase the accuracy of the method in some embodiments. For example, data transitions representing the curved shoulder 1270 would not be substantially parallel with the sides 1252 and 1254, and therefore recording these data transitions potentially increases the error in determining the location of the tool tip 1240 along the computed centerline 1290. Consequently, a sub-set of the rows may be traversed by skipping intermediate rows, or a sub-region of the image known to have transitions representing the sides 1252 and 1254 (or sides 1222 and 1224) may be traversed, e.g., the bottom half of the image 1700.

Figure 17B:
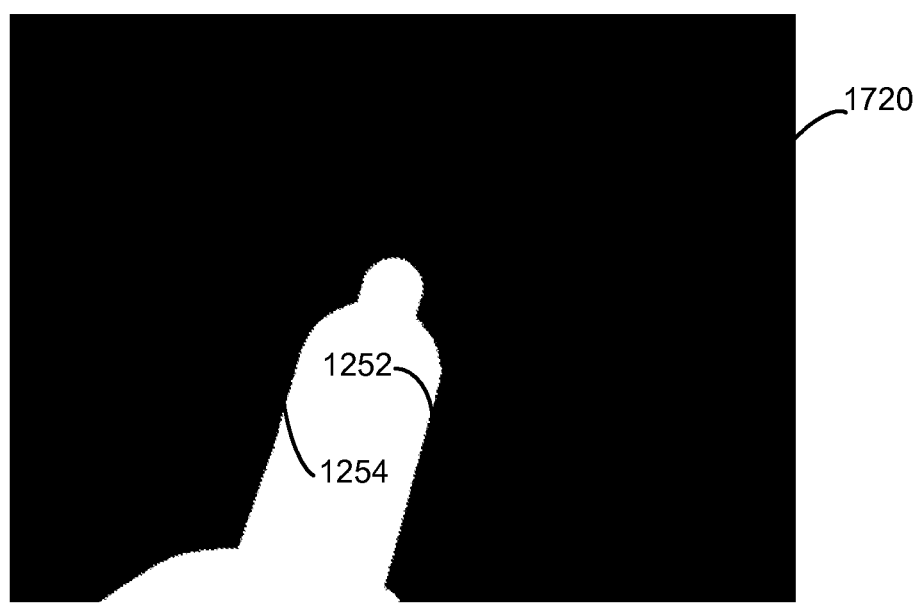

As shown in the example of FIG. 17B, the data transitions may be made more distinct by preprocessing the image data. In one example, an image of a tool may be binarized, e.g., converted to black and white, or converted into two colors, with a first color representing all pixel values below (or equal to) a threshold and another color value representing all pixels values exceeding the threshold. Determining a suitable threshold depends on the amount of shadow effects, lighting, reflectivity, and perspective distortion (discussed below with respect to FIGS. 18A and 18B). Consequently, image preprocessing is optional and grayscale edge detection may be used to locate the data transitions. In another example, data transition positions are initially determined by segmentation, and then edge detection techniques may be employed. A search can be performed around the initial segmented data transition position for each row, for example, in a small range, to locate the position where an edge is found. Subsequently, an edge detection operator can be applied such as a gradient-based detector, Sobel operator, etc.

A step 1623 includes calculating the first and second peripheral sidewall edge segments by performing a first regression from the first set of data transitions and a second regression from the second set of data transitions. Various estimation methods may be used for calculating the regression, such as, for example, ordinary least squares.

Figure 18A:
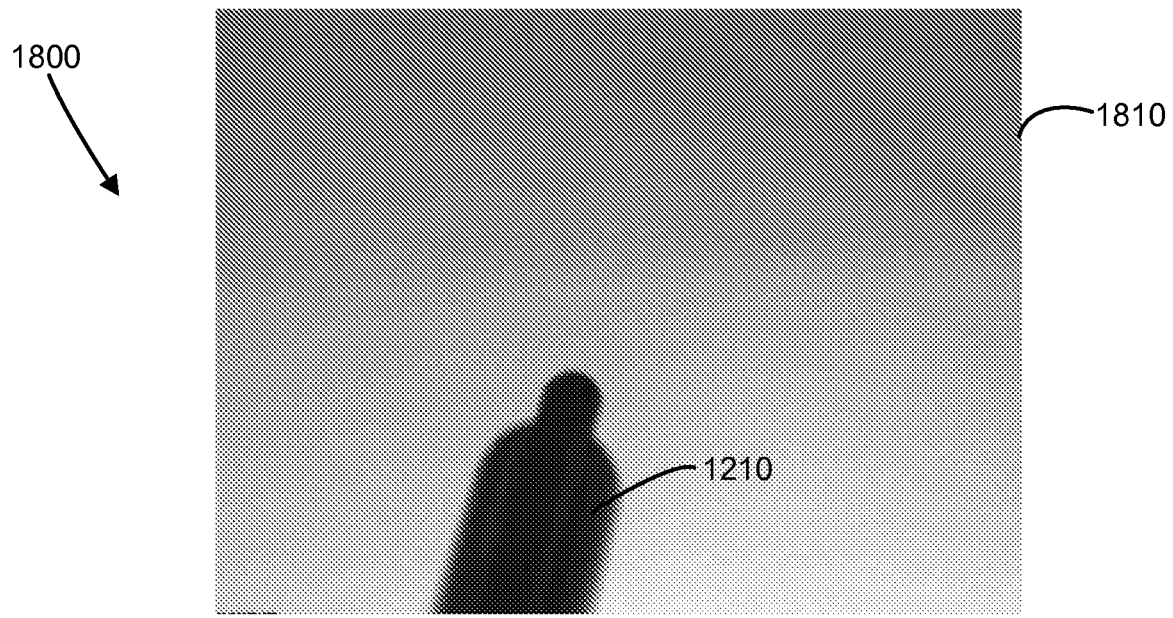
FIGS. 18A and 18B are respective unprocessed and binarized images of a retracted end-effector tool.
Figure 18B:
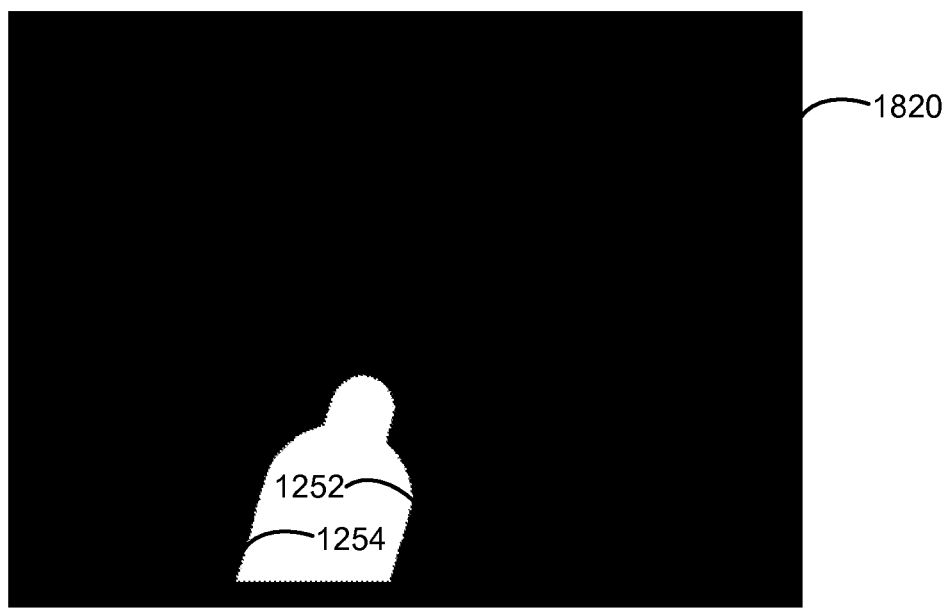

A regression calculation helps provide a fitted line segment based on the individual detected data transitions that, for various reasons, may not precisely align with one another, or align with the actual peripheral sidewalls. For example, when the camera 470 is fixed to the end-effector tool assembly 410, the optical path of the camera may not be exactly co-linear with the translational axis of motion of the needle assembly 1200. Consequently, there may be a significant amount of perspective distortion, or blurring, of the needle assembly 1200 in the field of view of the camera 470. In other words, the centerline 1290 of the needle assembly 1200 may not be exactly parallel to the camera's optical path resulting in the tip of the tool (e.g., punch 1240) being farther away in the camera's z-axis than the opposing end of the needle assembly 1200. In fact, the z-axis distance of the tips 1240 or 1280 may exceed the focus depth of some high magnification camera lenses. Thus, only a relatively small portion of, for example, the main cylindrical portion 1250 may be in crisp focus at any given moment. That may result a blurred, more difficult to detect, light-to-dark transition as shown in FIG. 18A. Additionally, the punch 1210 is not a flat surface with sharp detectable corners. As shown in FIG. 17B, for example, visible parts of the end-effector tooling or any data transitions representing the curved shoulder 1270 are not substantially parallel with a longitudinal axis and may potentially introduce error in calculating the or centerline 1290 for locating the tool tip 1240. Therefore, the regression calculations may be used to approximate the edges 1252 and 1254 (or 1222 and 1224) of the punch 1210.

In some embodiments, the tool, such as punch 1210, may be askew from the camera axis, resulting in a perspective distortion of the main cylindrical portion 1250 that is not uniform along the length of the punch 1210. For example, in FIGS. 18A and 18B, due to perspective distortion, the observable diameter of the punch near the bottom of an image 1810, and a corresponding preprocessed image 1820, is several pixels wider than the observable diameter by the curved shoulder 1270. Consequently, the detected sidewall edge segments from the step 1521 of the method 1500 (FIG. 15) may converge and eventually intersect due to the non-uniform distortion or lack of sharp focus. Therefore, the step 1526 of computing the centerline may include, in some embodiments, identifying a bisector of an angle formed by the two converging sidewall line segments.

Figure 19:
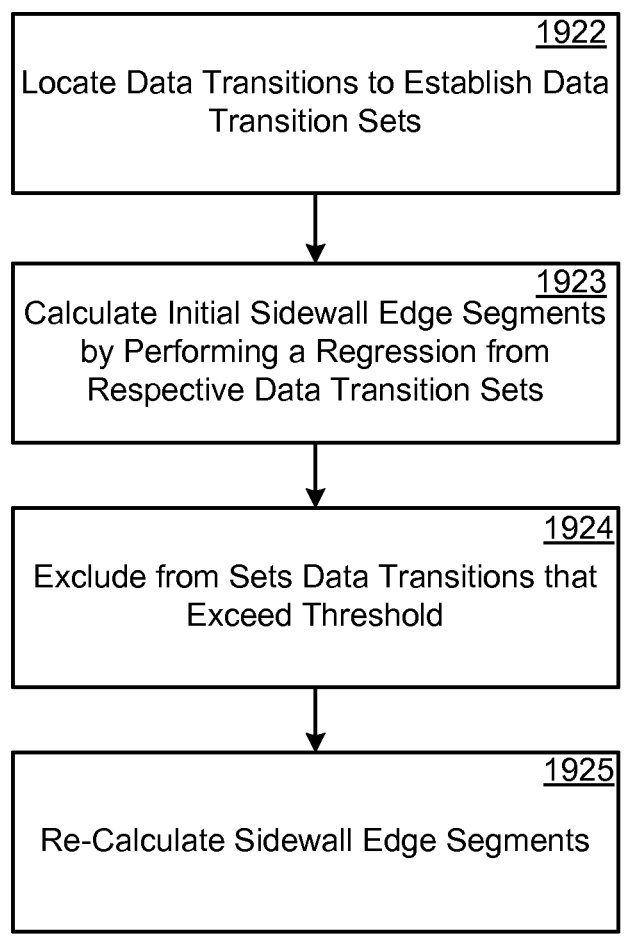
FIG. 19 is a flow diagram of another method for detecting sidewall edge segments of an end-effector tool.

FIG. 19 shows a flow diagram depicting another example method 1900 for carrying out the step 1521 of the method 1500 (FIG. 15). In general, the method 1900 uses a two-step process to identify and then filter out outlier data transitions. A step 1922 and a step 1923 correspond, respectively, to the steps 1622 and 1623 of the method 1600 (FIG. 16), with the calculated regressions serving as an initial approximation of the sidewalls 1222, 1224, or 1252, 1254.

Using the initial regression calculations for the sidewall edge segments, a step 1924 excludes from the first and second sets of data transitions, a first or second data transition having a distance from the respective first and second initial peripheral sidewall edge segments that exceeds a predetermined threshold, e.g., identifying and filtering the outliers from the data transition sets. A step 1925 includes re-calculating the first and second peripheral sidewall edge segments by performing a regression from the respective first and second sets of data transitions. The re-calculation may improve the accuracy of tool-location calibration since the re-calculated regression excludes outlier data transitions that potentially skew the calculation of the centerline 1290 and a data transition point along the calculated centerline 1290 representing to the tool tip 1280. The method 1900 and its steps may be implemented using various structures. For example, the steps 1922, 1923, 1924, and 1925 may be performed using one or more processors, such as the processor 425 or the image processor 426. The steps 1922, 1923, 1924, and 1925 may be performed in any order or in parallel (e.g., at the same time).

Figure 20:
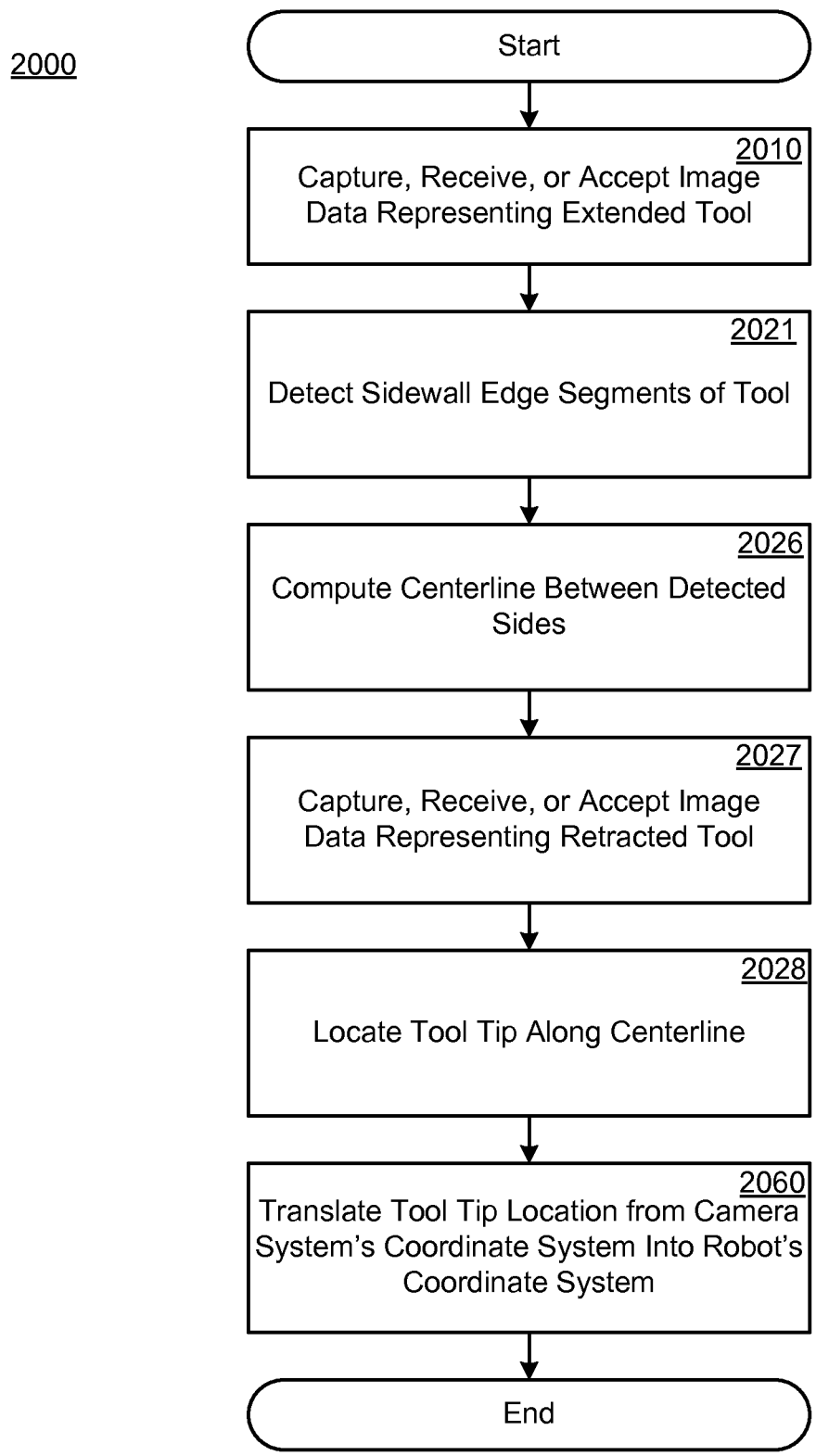
FIG. 20 is a flow diagram of a method for locating a distal end of an end-effector tool by using image data of the tool in extended and retracted conditions, according to one embodiment.

By extending the needle assembly along its axis of motion, a greater number of in-focus data transitions may be obtained along the sides 1252 and 1254 of the main cylinder 1250, thereby improving the approximation of the peripheral sidewall edge segments. The needle assembly may then be retracted and brought within sharp focus to determine the location of the tip 1240. In another embodiment, the focus of the camera may be changed so that the tool remains extended, but the focus on the tip of the tool is improved. FIG. 20 shows an example method 2000 for locating a distal end of an end-effector tool using image data of the tool in extended and retracted conditions. As in reference to previous examples, at an optional step 2010, the method 2000 may capture image data representing an extended tool, for example, the harvesting punch extended two millimeters beyond a skin plane, e.g., a plane formed by a patient's skin during a harvesting or implantation procedure. In certain embodiments, the image data may be received, accessed, or accepted. A step 2021 includes detecting sidewall edge segments, similar to the step 1521 of the method 1500 (FIG. 15). Likewise, a step 2026 corresponds to the step 1526. A step 2027 includes capturing image data representing the tool in a retracted condition, for example, the harvesting punch 1210 extended to a point above or on a skin plane. A step 2028 includes locating the tool tip and corresponds to the step 1528. A step 2060 includes translating the tool tip location, as described previously with respect to the step 1460.

The method 2000 and its steps may be implemented using various structures. For example, image capture step 2010 can be performed using a camera system, such as the camera system 415, and steps 2021, 2026, 2027, 2028, and 2060 may be performed using one or more processors, such as the processor 425 or the image processor 426. The steps 2010, 2021, 2026, 2027, 2028, and 2060 may be performed in any order or in parallel (e.g., at the same time).

Any of the aforementioned tool-location calibration methods 1400, 1500, 1600, 1900, or 2000 may take advantage of the optional binarization or other suitable preprocessing techniques, the optional locating of an angle bisector, the optional techniques for limiting the number of data transitions e.g., reducing the search space by skipping pixel rows or regions of the image, or optional multiple-image capture at various focus depths.

Figure 21A:
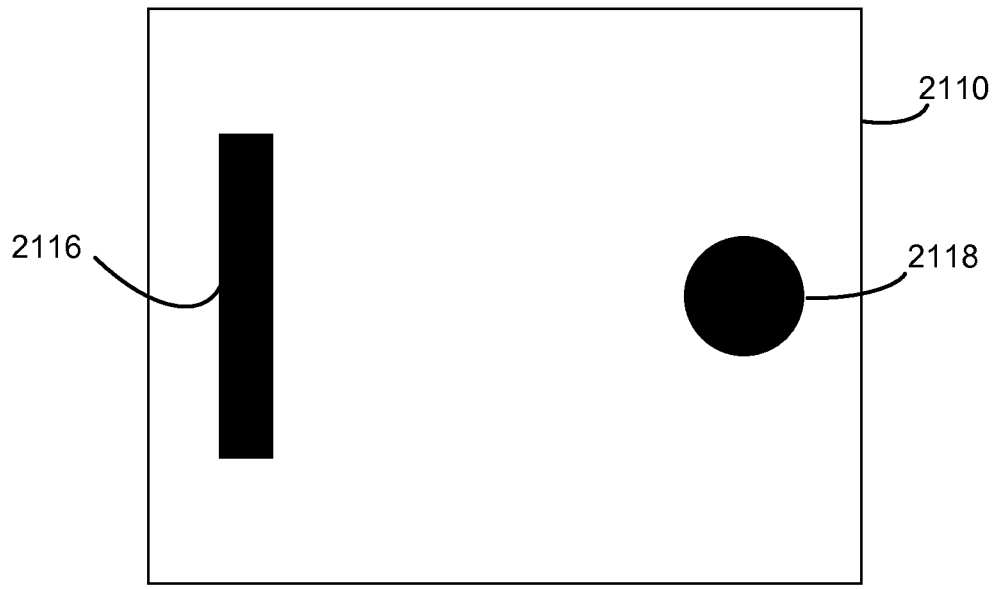
FIGS. 21A and 21B are depictions of placards bearing features for identifying relative positions and magnification of multiple cameras.
Figure 21B:
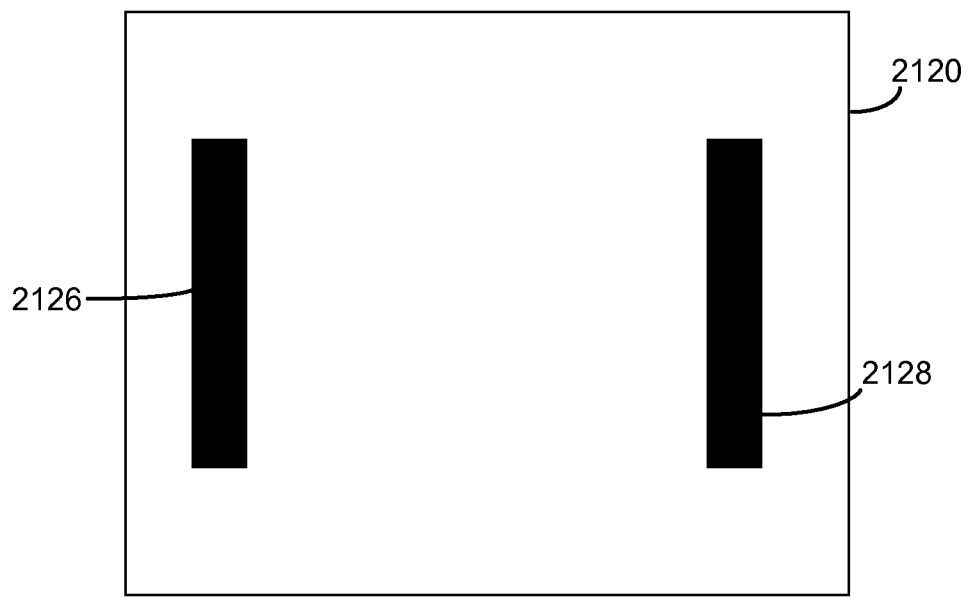

FIGS. 21A and 21B are depictions of placards 2110 and 2120 bearing features for identifying relative positions and magnification of multiple cameras. Users may place a placard in a camera system's field of view, observe image data from individual cameras representing the placards, and associate the individual cameras with physical configurations of the system based on the observed image data. The placards and obtained image data facilitate a method of configuring a camera control system that may be performed as an alternative to manually recording serial numbers (or other identifying indicia) from the individual cameras and entering the information into configuration software of a robot control system. Manually obtaining camera serial numbers from the cameras can be difficult due to the location and the size of serial number labels. Furthermore, some camera blocks do not have labels indicating which cameras are high magnification or low magnification, or which cameras are on the left side or the right side. Moreover, the definition of left and right side of a camera system can be confusing as the definitions depend on a person's position, relative to the camera system.

As shown in FIGS. 21A and 21B, the placards 2110 and 2120 may be printed with two fiducials—one on each side of the card, according to one embodiment. The placard 2110 includes a rectangular fiducial 2116 on the left and a circular fiducial 2118 on the right. The placard 2120 includes two rectangular fiducials 2126 and 2128 on opposing sides. The number and shape of the fiducials are somewhat arbitrary, provided that the orientation and general shape of the individual fiducials are discernable by machine vision operations. As discussed below, pairs of the fiducials 2116, 2118 or 2126, 2128 may be identified based on various optical properties so that a configuration system can differentiate between low and high magnification cameras, as well as between left and right side cameras. The checkerboard calibration target 700 (FIG. 7A) or the dot-centroid calibration targets 720 and 740 (FIGS. 7B and 7C) may be used for the camera identification. In another embodiment, the fiducials 2116, 2118 or 2126, 2128 may be printed with the targets 700, 720, 740 as part of a single calibration unit or cart (not shown).

Figure 22:
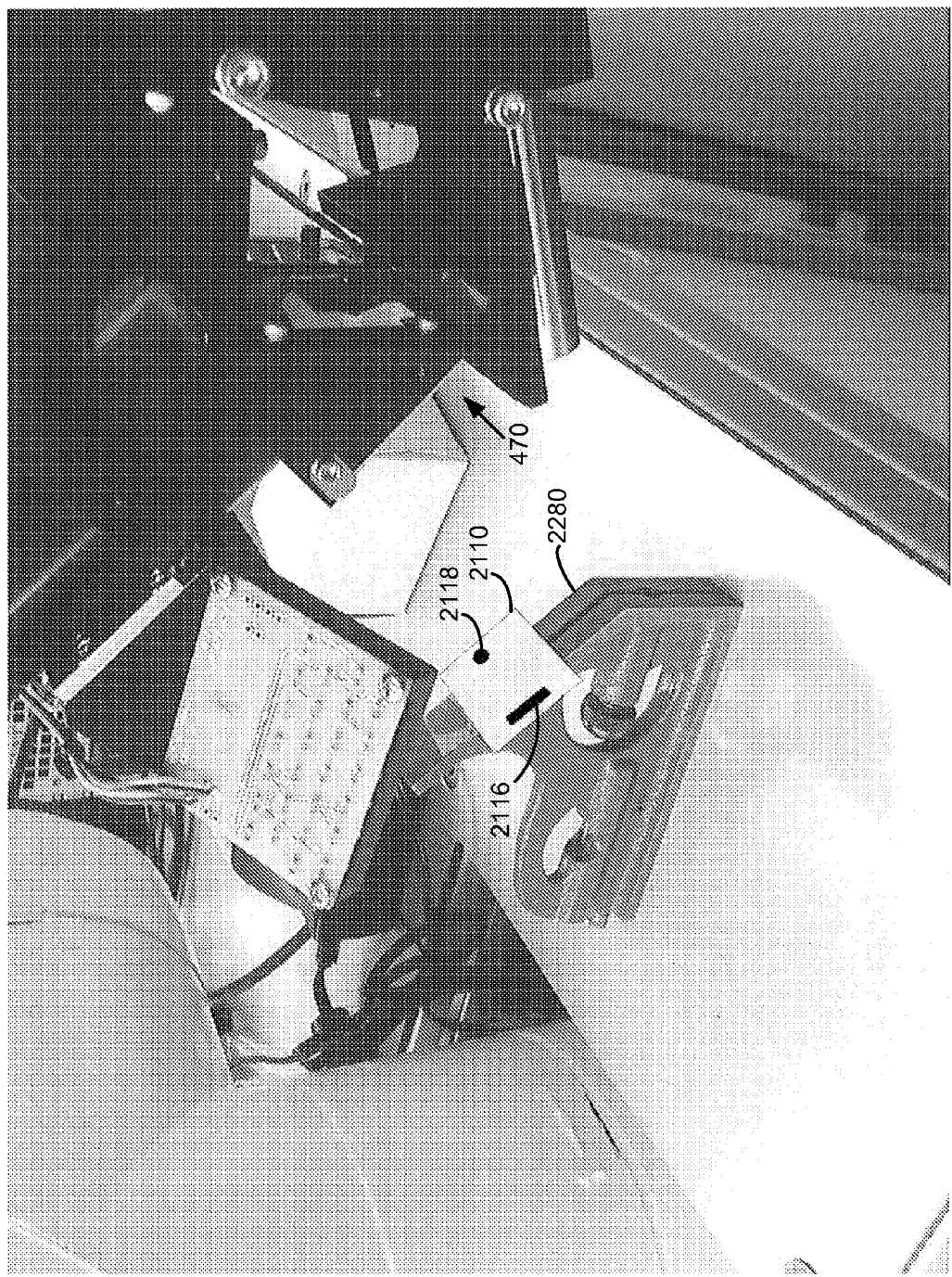
FIG. 22 is a perspective view of a placard positioned in a field of view of a camera system for identifying relative positions and magnification of multiple cameras.

FIG. 22 is a perspective view of the placard 2110 as shown in FIG. 21A, positioned in a field of view of a camera system, such as the camera system 470 described with respect to FIG. 4A, for identifying relative positions and magnification of multiple cameras. The placard 2110 is positioned such that the fiducials 2116 and 2118 appear laterally in the field of view of the camera system 470, according to one embodiment. As stand-alone processes, the camera identification routines discussed below do not depend on motion of a robotic arm, although automatic motion may also be used. During manufacture, with an end-effector on the assembly mount, the placard 2110 is placed on a suitable stand 2280 and moved into position. The stand 2280 may be positioned free-form, or the stand 2280 can be attached to the tool's assembly mount (not shown) to help provide more consistent images of the placard 2110. When the placard is positioned, appropriate lighting is applied. The lighting can be achieved either using the built in LED lights on the tool or the fiducials can be printed on a clear substrate and back-lit. A user or processor triggers an image capture of the placard 2110 and software executing on a processor, or dedicated machine vision hardware identifies positions and magnifications of cameras according to techniques described below.

Figure 23:
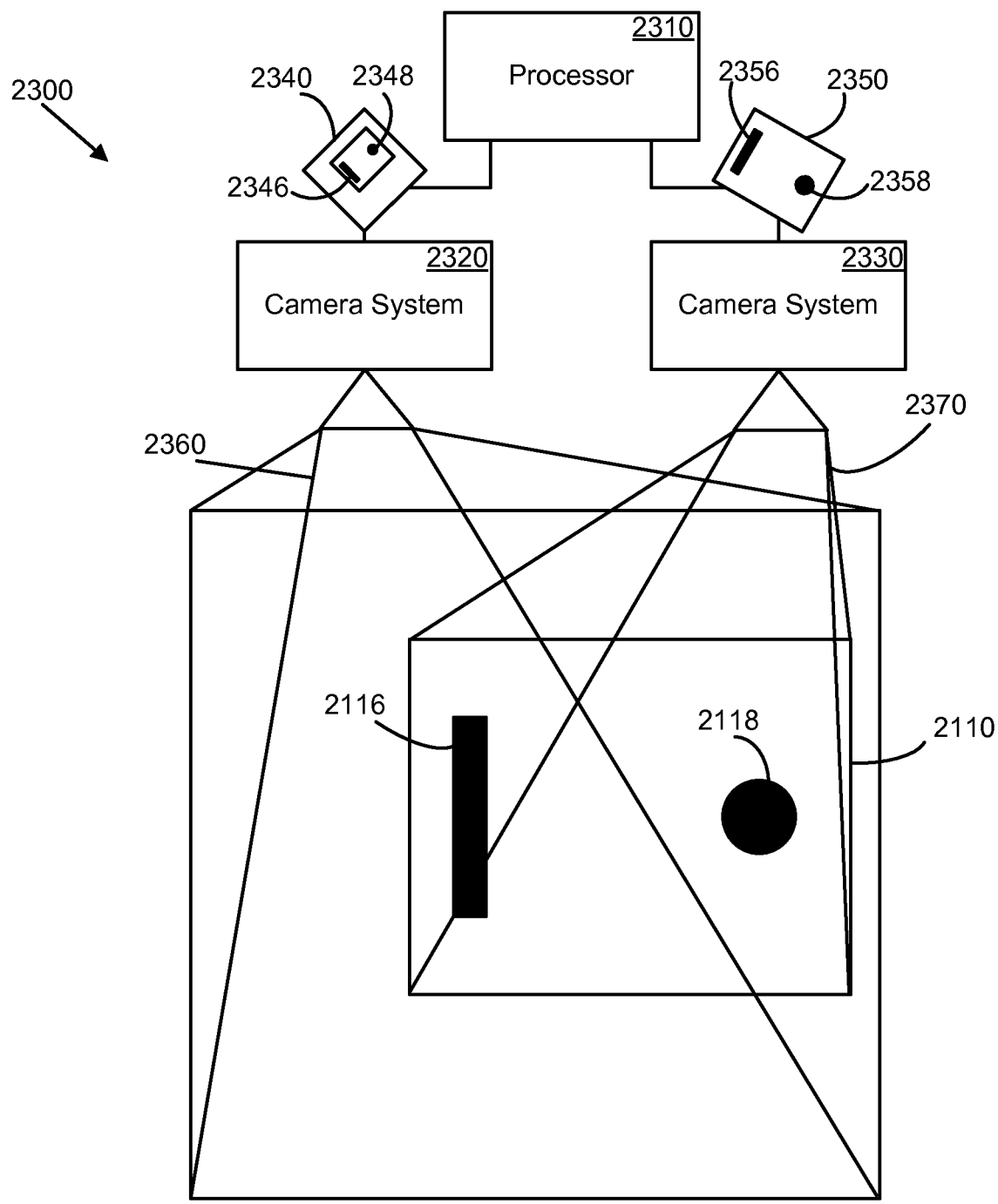
FIG. 23 is a diagram of a system for identifying a camera's magnification, according to one embodiment.

FIG. 23 shows an example system 2300 for identifying the magnification of individual cameras in a camera system. The example system 2300 includes a processor 2310 and at least two camera systems 2320 and 2330. In the example system 2300, the left camera system 2320 corresponds to a low-magnification camera system and the right camera system 2330 corresponds to a high-magnification camera system. The camera systems 2320 and 2330 may have a single camera each, or each may include a stereo camera system. The camera systems 2320 and 2330 are configured to obtain respective images 2340 and 2350 representing the placard 2110 when the placard 2110 is placed in fields of view 2360 and 2370 of the camera systems 2320 and 2330. In one embodiment, the fiducials 2116 and 2118 are entirely within the fields of view 2360 and 2370, with the size and spacing of the placard 2110, and the area of each fiducial 2116 and 2118 being predetermined. Because the area of each fiducial 2116 and 2118 on the placard 2110 is predetermined, if an area of a fiducial 2346, 2348 or 2356, 2358 in the obtained image 2340 or 2350 is above a threshold, the corresponding camera system 2320 or 2330 is determined to be a high magnification camera. In another embodiment, the images 2340 and 2350 may be compared to each other. For example, an area of the fiducials 2346 in the image 2340 is greater than an area of the fiducial 2356 in the image 2350. Thus, because the camera 2330 produced the fiducial 2356 having a greater area, the processor 2310 may properly identify the camera system 2330 as a high magnification camera.

Figure 24:
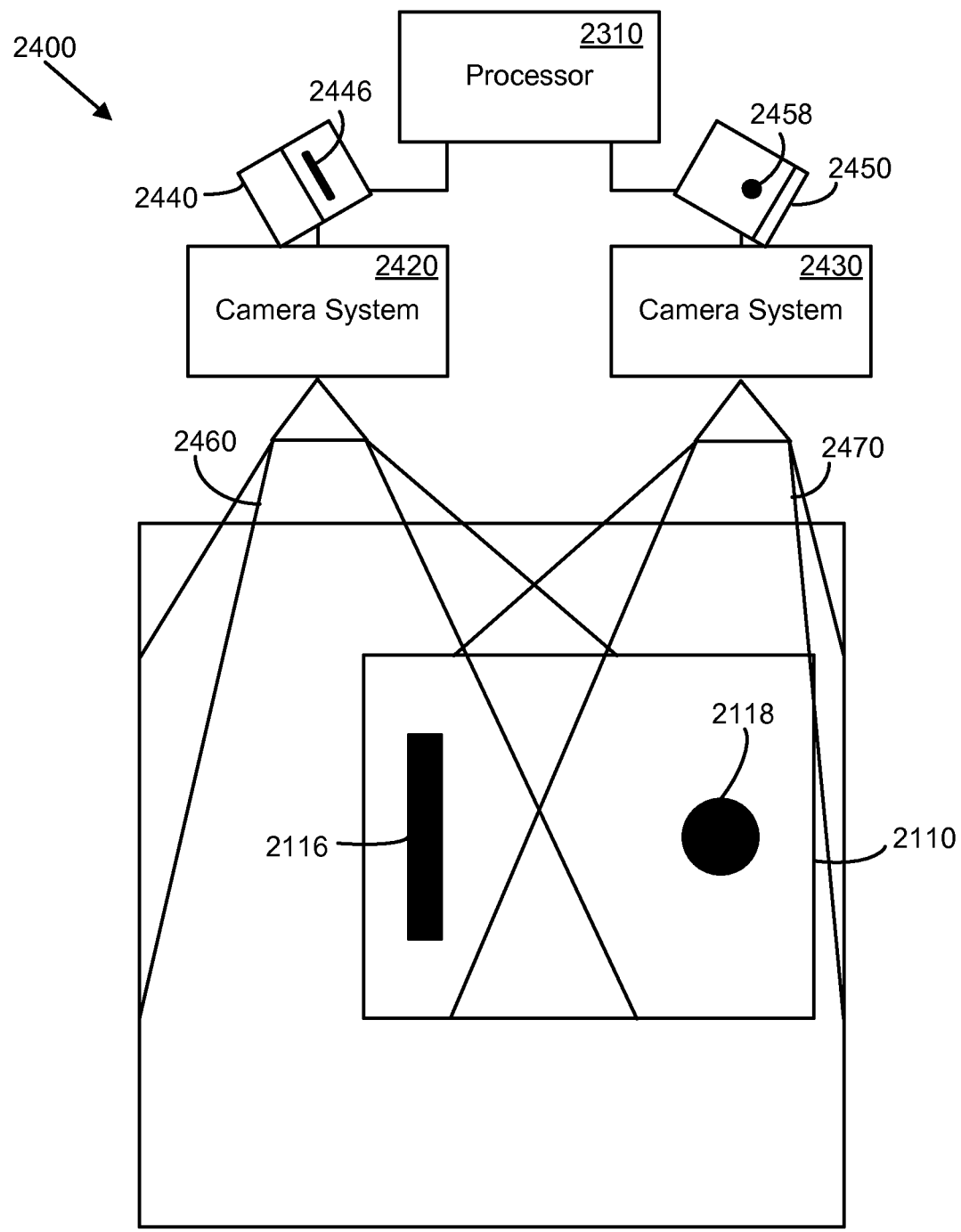
FIG. 24 is a diagram of a system for identifying a camera's relative position, according to one embodiment.
Figure 25:
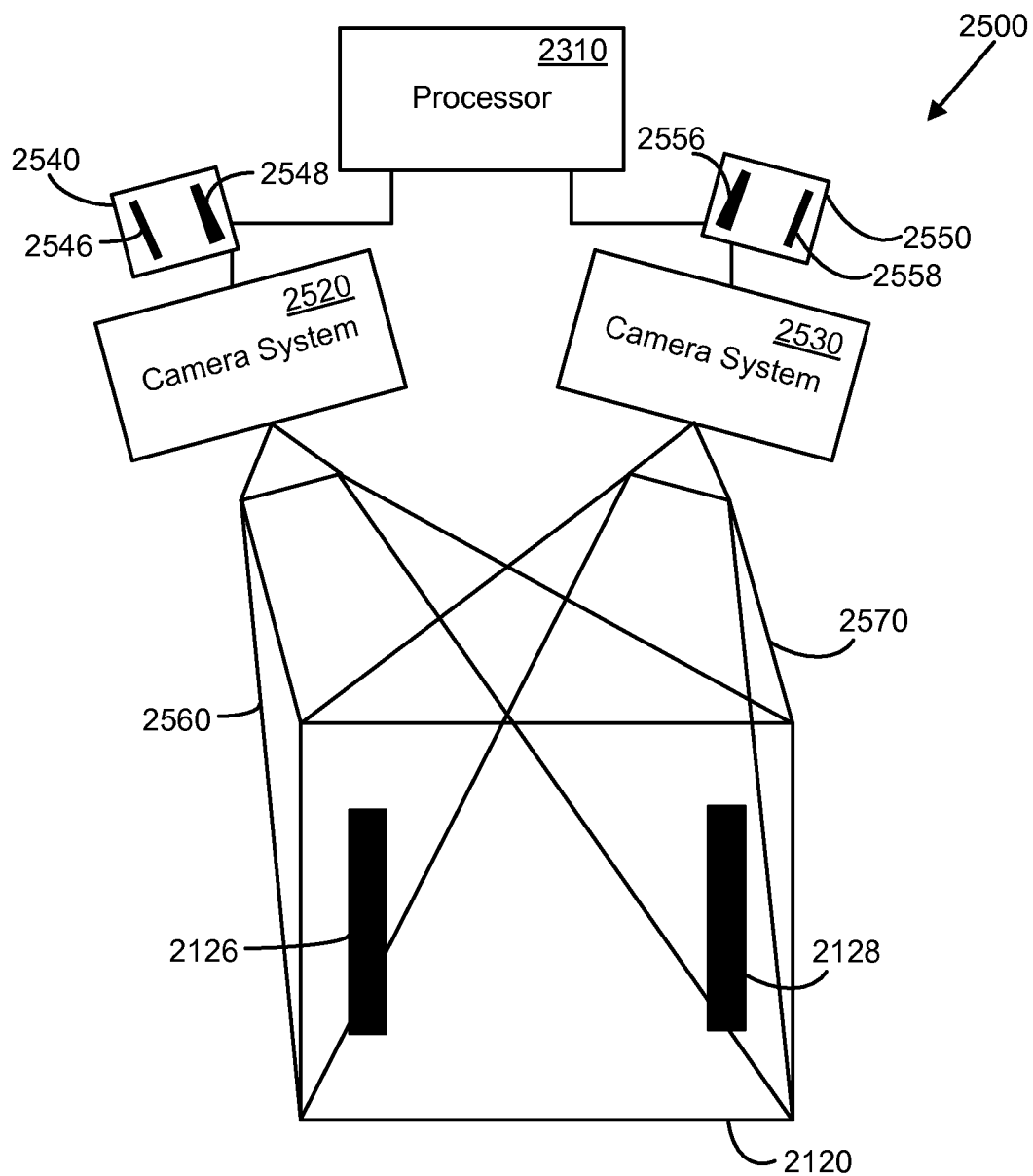
FIG. 25 is a diagram of a system for identifying camera's relative position, according to another embodiment.

FIGS. 24 and 25 show systems for identifying cameras on each side of an end-effector using, respectively, differences in fields of view and perspective distortions. In an example system 2400 shown in FIG. 24, camera systems 2420 and 2430 are high-magnification cameras for producing, respective images 2440 and 2450. The placard 2110 is placed in front of the camera systems 2420 and 2430 so that the fiducial 2116 is visible in the field of view 2460, while the fiducial 2116 is not. Conversely, the fiducial 2118 is visible in the field of view 2470, while the fiducial 2118 is not. Accordingly, when the fiducials 2116 and 2118 are shaped so to have distinctive properties such as moments of inertia, circularity, perimeter length, or other properties, the images 2440 and 2450 are not entirely overlapping and are sufficiently different such that the processor 2310 may determine the physical arrangement of the camera systems 2420 and 2430. For example, the image 2440 contains a rectangular fiducial 2446 representing the fiducial 2116 and the image 2450 contains a circular fiducial 2458 representing the fiducial 2118. In other words, the left high-magnification camera 2420, canted inwards, can only see the right fiducial 2116, while the right high-magnification camera 2430, canted inwards, can only see the left fiducial 2118.

In another example system 2500 shown in FIG. 25, camera systems 2520 and 2530 are not parallel to each other, but canted slightly inwards, such that perspective distortions affect the geometry of the fiducial shapes. The placard 2120, as described with respect to FIG. 21B, contains on each side, the rectangular shaped fiducials 2126 and 2128. Because the focal plane of the camera systems 2520 and 2530 are not perpendicular to the placard 2120, one fiducial in each of images 2540 and 2550 is slightly nearer to the focus point than the other fiducial, causing a difference in area between fiducials in the images 2540 and 2550. The pin-hole camera distortion of the shapes of the fiducials may be different as well, changing the shape profiles of the two sides. For example, a fiducial 2546 appears slightly smaller than a fiducial 2548, while a fiducial 2556 appears slightly larger than a fiducial 2558. Additionally, the fiducials 2546 and 2548 skew to the left, while the fiducials 2556 and 2558 skew to the right due to the pin-hold distortion. The perspective distortion may also be used to determine lens focus for individual cameras, by characterizing the amount of distortion on a fiducial of a predetermined shape. Furthermore, the locations of the fiducials 2546 and 2548 in the image 2540 may be shifted (not shown) when compared to the other image 2550 as a result of differences in fields of view 2560 and 2570, as described with respect to the system 2400.

Figure 26:
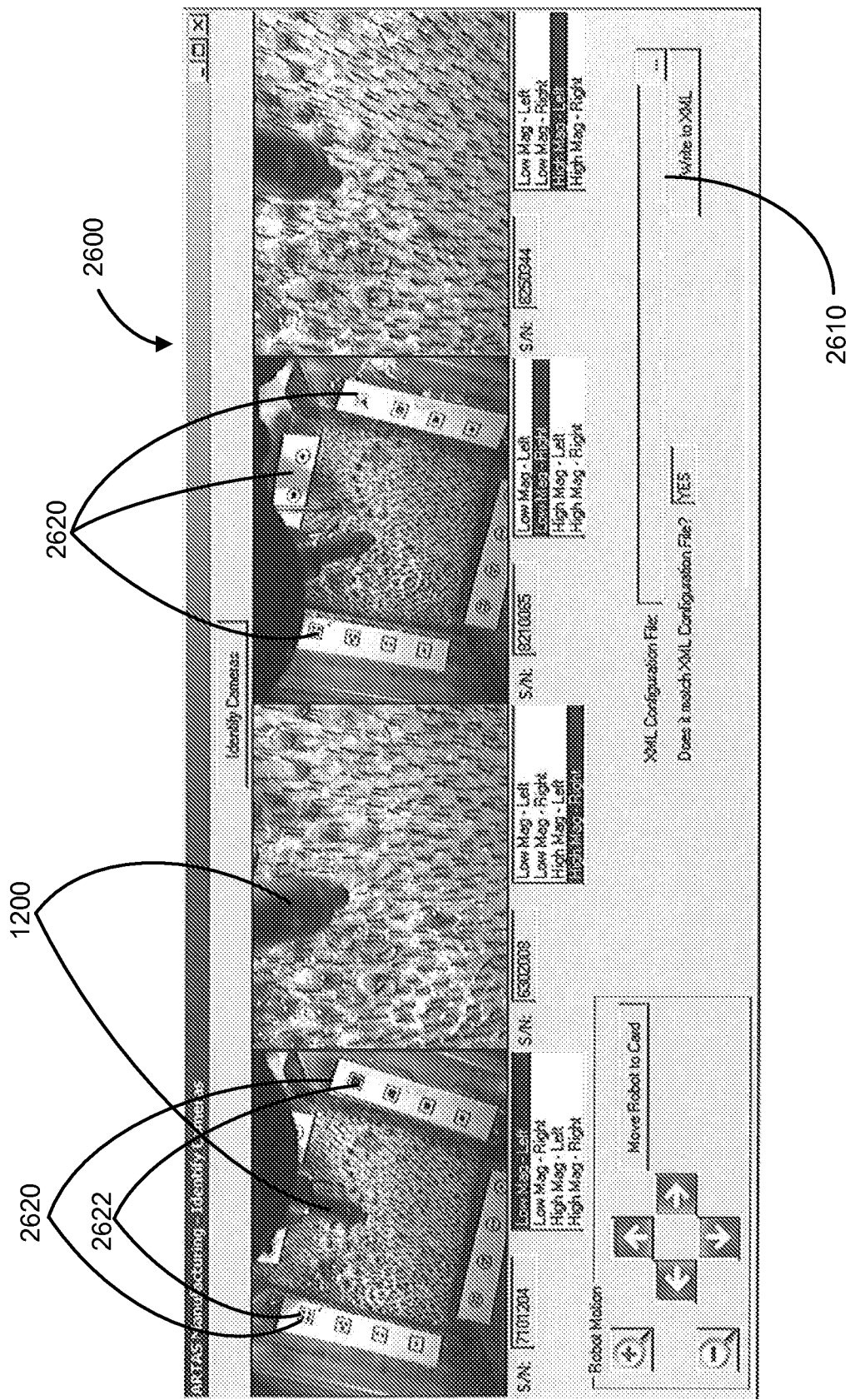
FIG. 26 is a screenshot of a software system for identifying and configuring relative positions and magnification of multiple cameras in a camera system, according to one embodiment.

FIG. 26 shows screenshot 2600 of a software application for validating the camera identification routines described above, and writing identification information to a system configuration XML file 2610. The XML file 2610 may include the positions, magnifications, lens focus, or other configuration parameters that allow the technician to track various aspects of the cameras. The identification data can be written initially during a system initialization, or overwritten during a camera reconfiguration. Verification of the automated identification routines may be performed as shown in FIG. 26. Strips 2620 containing fiducials 2622 (described with reference to FIG. 4B) are visible with low-magnification cameras, but not visible with high-magnification cameras due to the narrower fields of view, and the angle of the needle assembly 1200 is skewed in different directions for left and right cameras.

Embodiments may be implemented using computer software developed in various programming languages. Embodiments may be provided as a computer program product including a nontransitory machine-readable storage medium having stored thereon instructions (in compressed or uncompressed form) that may be used to program a computer (or other electronic device) to perform processes or methods described herein. The machine-readable storage medium may include, but is not limited to, hard drives, floppy diskettes, optical disks, CD-ROMs, DVDs, read-only memories (ROMs), random access memories (RAMs), EPROMs, EEPROMs, flash memory, magnetic or optical cards, solidstate memory devices, or other types of media/machine-readable medium suitable for storing electronic instructions. Further, embodiments may also be provided as a computer program product including a transitory machine-readable signal (in compressed or uncompressed form). Examples of machine-readable signals, whether modulated using a carrier or not, include, but are not limited to, signals that a computer system or machine hosting or running a computer program can be configured to access, including signals downloaded through the Internet or other networks. For example, distribution of software may be via CD-ROM or via Internet download.

Software programs that execute the methods and systems described herein may include a separate program code including a set of instructions for performing a desired operation or may include a plurality of modules that perform such sub-operations of an operation, or may be part of a single module of a larger program providing the operation. The modular construction facilitates adding, deleting, updating and/or amending the modules therein and/or features within the modules. The program may receive unique identifier information and/or additional information and may access, for example, a storage device having data associated with the unique identifier information and/or additional information.

The terms and descriptions used above are set forth by way of illustration only and are not meant as limitations. Skilled persons will recognize that many variations can be made to the details of the above-described embodiments without departing from the underlying principles of the disclosure. The scope of the invention should therefore be determined only by the following claims and their equivalents.

The invention claimed is:

1. A method for determining a transformation between a robot's coordinate system and a camera system's coordinate system, wherein the robot includes a movable arm having the camera system mounted thereto, the robot's coordinate system defines a position of the movable arm, and the camera system's coordinate system defines a position of a target within a field of view of the camera system, the method comprising:

positioning the movable arm about the target to three or more image-capture locations such that the target is within the field of view of the camera system at individual image-capture locations and the movable arm is rotated about and translated relative to the target from one image-capture location to another image-capture location;

at the individual image-capture locations, capturing a set of images of the target using the camera system and recording, in the robot's coordinate system, a position of the movable arm;

determining, in the camera system's coordinate system, coordinates of a set of two or more calibration features of the target identified in the set of images; and determining, based on the position of the movable arm and the coordinates of the set of two or more calibration features at the individual image-capture locations, the transformation between the robot's coordinate system and the camera system's coordinate system, wherein a position of the target is fixed and the step of determining the transformation between the robot's coordinate system and the camera system's coordinate system comprises iteratively selecting a value for the transformation between the robot's coordinate system and the camera system's coordinate system and comparing (A) a product of the selected value for the transformation, a position of the movable arm, and coordinates of a calibration feature at one image-capture location and (B) a product of the selected value for the transformation, a position of the movable arm, and coordinates of the corresponding calibration feature at another image-capture location to determine a value for the transformation that minimizes a difference between (A) and (B).

2. A method according to claim 1, wherein the steps of positioning the movable arm about the target, capturing the set of images of the target, recording the position of the movable arm, determining the coordinates of the set of two or more calibration features, and determining the transformation between the robot's coordinate system and the camera system's coordinate system are performed automatically.

3. A method according to claim 1, wherein the movable arm has mounted thereto a follicular unit harvesting tool, a follicular unit implantation tool, or both, and the robot is configured to harvest follicular units, implant follicular units, or both, and further comprising:

identifying, in the camera system's coordinate system, a location of a follicular unit in an image of the body surface;

determining, in the robot's coordinate system, a location of the follicular unit based on the location of the follicular unit in the camera system's coordinate system and the transformation between the robot's coordinate system and the camera system's coordinate system; and positioning the movable arm adjacent the follicular unit based on the location of the follicular unit in the robot's coordinate system so that the follicular unit can be harvested or implanted using the follicular unit harvesting or implantation tool.

4. A method according to claim 1, wherein the transformation between the robot's coordinate system and the camera system's coordinate system comprises a transformation matrix T and the step of determining the transformation comprises finding a transformation matrix T that at least approximately minimizes the quantity $\Sigma_{i=2}^{m}\Sigma_{j=1}^{(i-1)}\Sigma_{k=1}^{n}\|R_i T v_{ik} - R_j T v_{jk}\|$, wherein i and j correspond to different instances of individual image-capture locations, i has a value ranging from 2 to m, j has a value ranging from 1 to (i−1), k corresponds to an individual calibration feature in the set of two or more calibration features and has a value ranging from 1 to n, $R_i$ is the position of the movable arm at an individual image-capture location i, $v_{ik}$ are the coordinates, determined in the camera system's coordinate system, of the $k^{th}$ calibration feature at the $i^{th}$ image-capture location, $R_j$ is the position of the movable arm at an individual image-capture location j, and $v_{jk}$ are the coordinates, determined in the camera system's coordinate system, of the $k^{th}$ calibration feature at the $j^{th}$ image-capture location.

5. A method according to claim 4, wherein the position of the movable arm comprises a robot-position transformation matrix R of the form $$R = \begin{bmatrix} r_{00} & r_{01} & r_{02} & x \\ r_{10} & r_{11} & r_{12} & y \\ r_{20} & r_{21} & r_{22} & z \\ 0 & 0 & 0 & 1 \end{bmatrix},$$

the sub-matrix $$\begin{bmatrix} r_{00} & r_{01} & r_{02} \\ r_{10} & r_{11} & r_{12} \\ r_{20} & r_{21} & r_{22} \end{bmatrix}$$

represents an orthonormal rotation relating an orientation of the movable arm to a reference orientation, and the sub-matrix $$\begin{bmatrix} x \\ y \\ z \end{bmatrix}$$

represents an offset between the position of the movable arm and a reference position,
the coordinates of an individual calibration feature comprise an array of the form $$v = \begin{bmatrix} x \\ y \\ z \\ 1 \end{bmatrix},$$

and
the transformation matrix T comprises a matrix of the form $$T = \begin{bmatrix} r_{00} & r_{01} & r_{02} & x \\ r_{10} & r_{11} & r_{12} & y \\ r_{20} & r_{21} & r_{22} & z \\ 0 & 0 & 0 & 1 \end{bmatrix},$$

the sub-matrix $$\begin{bmatrix} r_{00} & r_{01} & r_{02} \\ r_{10} & r_{11} & r_{12} \\ r_{20} & r_{21} & r_{22} \end{bmatrix}$$

represents a rotational relationship between the robot's coordinate system and the camera system's coordinate system and is derived from three rotational offsets $\alpha$, $\beta$, and $\gamma$, and the sub-matrix $$\begin{bmatrix} x \\ y \\ z \end{bmatrix}$$

represents translation offsets x, y, and z between the robot's coordinate system and the camera system's coordinate system.

6. A method according to claim 1, wherein the transformation between the robot's coordinate system and the camera system's coordinate system is determined using an optimization algorithm including one or more of a steepest descent optimization algorithm, a simulated annealing algorithm, or a best fit algorithm.

7. A method according to claim 1, wherein the individual image-capture locations lie approximately on a surface of a sphere having a center point approximately coincident with the target.

8. A method according to claim 1, wherein the movable arm is moved radially with respect to the target from one image-capture location to another image-capture location.

9. A method according to claim 1, wherein the camera system comprises respective first and second stereo camera pairs mounted to the movable arm, the first stereo camera pair is focused and configured to acquire images of a first field of view, the second stereo camera pair is focused and configured to acquired images of a second field of view that is substantially narrower than the first field of view, the first and second fields of view at least partially overlap, and the step of determining the transformation between the robot's coordinate system and the camera system's coordinate system comprises determining a first transformation for the first stereo camera pair using an optimization algorithm and determining a second transformation for the second stereo camera pair using an optimization algorithm, and further comprising:
determining a transformation matrix Q that maps coordinates in the first stereo camera pair's coordinate system to the second stereo camera pair's coordinate system.

10. A method according to claim 1, further comprising locating, in the robot's coordinate system, a tool extending from the movable arm of the robot, wherein locating comprises:
determining from image data a location in a camera system's coordinate system of the tool; and
translating the location of the tool from the camera system's coordinate system into the robot's coordinate system using a predetermined transformation.

11. A method according to claim 10, further comprising:
capturing image data, wherein the image data comprises a pair of images, and wherein the determining step comprises detecting from the image data first and second peripheral sidewall edge segments corresponding to sides of the tool within a field of view of the camera system, computing a centerline based on an average between the detected first and second peripheral sidewall edge segments, and locating in the camera system's coordinate system a position of a distal end of the tool along the centerline.

12. A method according to claim 11, wherein the centerline bisects an angle formed between the first and second peripheral sidewall edge segments.

13. A method according to claim 11, wherein the detecting step comprises locating first and second data transitions in individual rows of the image data to establish a first and second set of data transitions, calculating the first and second peripheral sidewall edge segments by performing a regression from the respective first and second sets of data transitions, and wherein the locating step comprises locating a distal-end data transition in the image data along the centerline such that the location of the distal-end data transition represents the spatial position of the distal end in the camera system's coordinate system.

14. A method according to claim 13, wherein the first and second data transitions comprise one or more of contrast, intensity, color, or brightness transitions of the image data.

15. A method according to claim 13, wherein the detecting step further comprises processing the image data such that the distal end is represented as a unique value within the image data.

16. A method according to claim 13, wherein the detecting step further comprises binarizing the image data such that the distal end is represented by a first unique color and background features are represented by a second unique color.

17. A method according to claim 13, wherein the data transitions comprise grayscale edge points.

18. A method according to claim 13, wherein the regression comprises a best-fit algorithm that approximately connects respective first and second sets of data transitions and/or a least-squares fit that approximately connects respective first and second sets of data transitions.

19. A method according to claim 10, further comprising:
capturing image data, wherein the image data comprises two-dimensional data from a first and a second camera system which capture the image data at substantially the same time, and calculating a three-dimensional location from the two-dimensional image data.

20. A method according to claim 10, further comprising:
determining an offset between a flange of the tool and a tip of the tool to automatically compute the tool tip location in three-dimensions.

21. A method of claim 10, wherein the method comprises positioning a tip of the tool on a body surface during a hair extraction or a hair implantation procedure.

22. A method of claim 10, further comprising:
capturing an image of a feature of interest relative to the tool and generating instructions that cause a controller to move the arm of the robot to a desired position and orientation.

23. A method of claim 21, further comprising rotating the tool and/or aligning the tool with the feature of interest.

24. A method according to claim 1, wherein the set of two or more calibration features is based on features selected from checkerboard corners, dot centroids, or both.

25. A method according to claim 9, further comprising identifying relative positions and magnification of the first and second stereo cameras, and wherein the set of two or more calibration features are used for the camera identification.

26. A method according to claim 25, wherein identifying the magnification comprises differentiating between left and right side cameras.

* * * * *